(12) United States Patent
Choi et al.

(10) Patent No.: US 10,494,333 B2
(45) Date of Patent: Dec. 3, 2019

(54) COMPOUND HAVING BLT INHIBITORY ACTIVITY AND COMPOSITION, FOR PREVENTING OR TREATING INFLAMMATORY DISEASES, COMPRISING SAME AS ACTIVE INGREDIENT

(71) Applicants: DONGGUK UNIVERSITY INDUSTRY-ACADEMIC COOPERATION FOUNDATION, Seoul (KR); KOREA UNIVERSITY RESEARCH AND BUSINESS FOUNDATION, Seoul (KR)

(72) Inventors: Yongseok Choi, Goyang-si (KR); Jae-Hong Kim, Seongnam-si (KR); Kyeong Lee, Goyang-si (KR); Hyo-Kyung Han, Seoul (KR); Jun Dong Wei, Seoul (KR); Jinsun Kwon, Yongin-si (KR); Ja-Il Goo, Seoul (KR)

(73) Assignees: DONGGUK UNIVERSITY INDUSTRY-ACADEMIC COOPERATION FOUNDATION, Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 15/745,348

(22) PCT Filed: Jul. 23, 2016

(86) PCT No.: PCT/KR2016/008070
§ 371 (c)(1),
(2) Date: Mar. 30, 2018

(87) PCT Pub. No.: WO2017/018751
PCT Pub. Date: Feb. 2, 2017

(65) Prior Publication Data
US 2018/0215706 A1 Aug. 2, 2018

(30) Foreign Application Priority Data

Jul. 24, 2015 (KR) .................. 10-2015-0105097
Jul. 22, 2016 (KR) .................. 10-2016-0093760

(51) Int. Cl.
| | |
|---|---|
| C07D 295/205 | (2006.01) |
| C07C 311/21 | (2006.01) |
| C07C 233/07 | (2006.01) |
| C07C 233/88 | (2006.01) |
| C07C 235/34 | (2006.01) |
| C07C 237/42 | (2006.01) |
| C07C 311/16 | (2006.01) |
| C07D 295/192 | (2006.01) |
| A61P 11/06 | (2006.01) |
| A61P 35/00 | (2006.01) |
| C07C 275/32 | (2006.01) |
| C07D 257/04 | (2006.01) |
| C07D 295/185 | (2006.01) |
| C07C 233/51 | (2006.01) |
| C07D 213/56 | (2006.01) |
| C07D 211/06 | (2006.01) |
| C07D 241/04 | (2006.01) |
| C07D 265/30 | (2006.01) |

(52) U.S. Cl.
CPC ............ *C07C 311/21* (2013.01); *A61P 11/06* (2018.01); *A61P 35/00* (2018.01); *C07C 233/07* (2013.01); *C07C 233/51* (2013.01); *C07C 233/88* (2013.01); *C07C 235/34* (2013.01); *C07C 237/42* (2013.01); *C07C 275/32* (2013.01); *C07C 311/16* (2013.01); *C07D 211/06* (2013.01); *C07D 213/56* (2013.01); *C07D 241/04* (2013.01); *C07D 257/04* (2013.01); *C07D 265/30* (2013.01); *C07D 295/185* (2013.01); *C07D 295/192* (2013.01); *C07D 295/205* (2013.01)

(58) Field of Classification Search
CPC ....................................................... C07C 311/21
See application file for complete search history.

(56) References Cited

U.S. PATENT DOCUMENTS 9,522,873 B2 * 12/2016 Lee .................... C07C 233/47
2008/0132574 A1 6/2008 Nakade et al.

FOREIGN PATENT DOCUMENTS

| KR | 20090125837 A | 12/2009 |
| KR | 10-20130017073 | * 2/2013 |

(Continued)

OTHER PUBLICATIONS

McMahon et al. (2000).*

(Continued)

*Primary Examiner* — Paul V Ward
(74) *Attorney, Agent, or Firm* — Lucas & Mercanti, LLP

(57) ABSTRACT

The present invention relates to a novel compound showing leukotriene B4 receptor 2 (BLT2) inhibitory activity and a pharmaceutical composition, for preventing or treating inflammatory diseases, having same as an active ingredient. The inventors identified a novel compound containing BTL2 inhibitory activity, and experimentally confirmed that the present novel compound had an excellent effect on the enhancement of the cancer cell death, on the inhibition of the metastasis and chemotactic mobility, and on the anti-asthma activity. Therefore, the present novel compound can be used as a very effective pharmaceutical component for treating the inflammatory-related diseases.

9 Claims, 18 Drawing Sheets

(56) References Cited

FOREIGN PATENT DOCUMENTS

| KR | 20130017073 A | 2/2013 |
|----|---------------|--------|
| WO | 2006083477 A2 | 8/2006 |
| WO | 2008073929 A1 | 6/2008 |

OTHER PUBLICATIONS

Pinedo et al. (2000).*
International Search Report for international Application No. PCT/KR2016/008070( 3 Pages) ( dated Nov. 8, 2016).

* cited by examiner

… (1)

COMPOUND HAVING BLT INHIBITORY ACTIVITY AND COMPOSITION, FOR PREVENTING OR TREATING INFLAMMATORY DISEASES, COMPRISING SAME AS ACTIVE INGREDIENT

CROSS-REFERENCE TO RELATED APPLICATIONS

This application is a 371 of PCT/KR2016/008070, filed Jul. 23, 2016, which claims the benefit of priority from Korean Patent Application No. 10-2015-0105097, filed Jul. 24, 2015 and Korean Patent Application No. 10-2016-0093760, filed Jul. 22, 2016, the contents of each of which are incorporated herein by reference.

TECHNICAL FIELD

The present invention relates to a novel compound and a use thereof, and more particularly, to a novel compound exhibiting a leukotriene B4 receptor 2 (BLT2) inhibitory activity and a pharmaceutical composition for preventing or treating an inflammatory disease, which includes the novel compound as an active ingredient.

BACKGROUND ART

An inflammatory response is one of the human immune systems activated by various action mechanisms to defend against physical actions, chemicals, bacterial infections, or immunological stimuli, which are applied to living organisms or tissue. However, when such inflammatory response persists, rather, damage to a mucous membrane is promoted, and therefore it has been noted that inflammatory diseases including rheumatoid arthritis, atherosclerosis, gastritis, asthma, etc. are caused by erythema, a fever, swelling, pain, or dysfunction. Such an inflammatory response is classified into acute inflammation and chronic inflammation as time passes. The acute inflammation is an inflammatory response lasting several days to several weeks, and causes a symptom such as erythema, a fever, pain, or swelling, whereas the chronic inflammation is a long-term inflammatory state for several years to decades, and involves a histological change such as fibrosis or the destruction of tissue caused by the infiltration of monocytes, proliferation of fibroblasts or capillaries, or an increase in connective tissue.

Specifically, when inflammatory stimuli are applied to the living organism, locally, histamine, bradykinin, prostaglandins, nitric oxide (NO), all types of pro-inflammatory cytokines, etc. are synthesized and secreted, and cause erythema, a fever, pain, or swelling as well as vasodilation. Particularly, in inflammation in the body, in addition to common immune factors, for example, cytokines such as interferon-γ (INF-γ), tumor necrosis factor-α (TNF-α), interleukin-1 (IL-1), and interleukin-6 (IL-6), nitric oxide (NO) and prostaglandin E2 (PGE2) are well known as major proinflammatory materials.

Conventionally, the termination of an inflammation response is known as a phenomenon naturally and passively occurring due to a decrease in levels of materials initiating inflammation, but it was found that the termination of inflammation is actively promoted by lipoxins, resolvins, or protectins, which were discovered by Serhan et al., like prostaglandins, which are involved in the initiation of inflammation. For example, it has been reported that resolvin E1 is effective for pain, and RvE1 induces the termination of inflammation and is effective in treating an allergic inflammatory disease. In addition, it has been reported that low levels of factors actively promoting the termination of inflammation in a chronic inflammatory disease, such as lipoxin A4 and lipixin that are induced by aspirin, are shown in asthmatic patients and atherosclerotic patients.

Accordingly, while various attempts to find novel materials for inducing the termination of inflammation and thus to treat diseases associated with abnormal inflammation termination have been made (Korean Unexamined Patent Application No. 10-2015-0011875), the compound known to be included in lipoxins, resolvins, etc. is metabolically unstable and thus rapidly degraded in the body due to several double bonds in its structure, and is somewhat difficult to be developed as a drug by mass production of a material, thereby having a great problem in drugability.

Meanwhile, leukotriene B4 ($LTB_4$) is a group of inflammatory lipid mediators synthesized from arachidonic acid (AA) via the 5-lipoxygenase pathway mediating both acute and chronic inflammation. $LTB_4$ is known to exert its biological activity by binding to the two types of receptors, BLT1 and BLT2. Leukotriene B4 receptor 2 (BLT2), a member of the G protein-coupled receptor (GPCR) family, has a low affinity to $LTB_4$ that is a lipid mediator of arachidonic acid (AA) induced via a 5-lipoxygenase-dependent pathway.

Accordingly, in order to solve the conventional problems as mentioned above, the inventors identified a novel compound exhibiting a BLT2 inhibitory activity. On the other hand, the inventors have been conducting a research to develop compounds to induce the effective termination of inflammation, and have primarily identified a therapeutic agent for an inflammatory disease, which includes the above-mentioned compound.

DISCLOSURE

Technical Problem

The present invention is aimed to solve the above-mentioned problems, and the inventors confirmed a therapeutic effect of a novel compound exhibiting a BLT2 inhibitory activity on an inflammatory disease, and based on this, the present invention was completed.

Therefore, an object of the present invention is to provide a novel compound exhibiting a BLT2 inhibitory activity or a pharmaceutically acceptable salt thereof.

Another object of the present invention is to provide a pharmaceutical composition for preventing or treating an inflammatory disease, which includes the novel compound or pharmaceutically acceptable salt thereof as an active ingredient.

However, technical problems to be solved in the present invention are not limited to the above-described problems, and other problems which are not described herein will be fully understood by those of ordinary skill in the art from the following description.

Technical Solution

To achieve these objects as mentioned above, the present invention provides a novel compound exhibiting a BLT2 inhibitory activity or a pharmaceutically acceptable salt thereof.

According to an exemplary embodiment of the present invention, the compound may be selected from the group consisting of N-((3'-(4-methylphenylsulfonamido)biphenyl- 4-yl)methyl)-N-phenylpentaneamide; N-(4'-((N-phenylpentaneamido)methyl)biphenyl-3-yl)-4-(trifluoromethyl)benzamide; N-(3-fluorophenyl)-N-((3'-(4-methylphenylsulfonamido)biphenyl-4-yl)methyl)pentaneamide; N-(4'-((N-3-fluorophenyl)pentaneamido)methyl)biphenyl-3-yl)-4-(trifluoromethyl)benzamide; 1-(3-fluorophenyl)-1-((4'-methoxybiphenyl-4-yl)methyl)-3-(3-(trifluoromethyl)phenyl)urea; N-(3-fluorophenyl)-N-((4'-methoxybiphenyl-4-yl)methyl)-1-(4-methoxyphenylsulfonyl)methaneamide; 1-(3-fluorophenyl)-1-((4'-hydroxybiphenyl-4-yl)methyl)-3-(3-(trifluoromethyl)phenyl)urea; 2-(4'-((1-(3-fluorophenyl)-3-(3-(trifluoromethyl)phenyl)ureido)methyl)biphenyl-4-yloxy)acetic acid; 4-(4'-((N-(3-fluorophenyl)pentaneamido)methyl)biphenyl-4-yloxy)butanoic acid; 2-(4'-((N-(3-fluorophenyl)pentaneamido)methyl)biphenyl-4-yloxy)-2-methylpropanoic acid; (E)-3-(4'-((N-(3-fluorophenyl)pentaneamido)methyl)biphenyl-4-yloxy)acrylic acid; 3-(4'-((N-(3-fluorophenyl)pentaneamido)methyl)biphenyl-4-yloxy)propanoic acid; N-(3-fluorophenyl)-N-((4'-(2-(4-methylpiperazine-1-yl)-2-oxoethoxy)biphenyl-4-yl)methyl)pentaneamide; prop-2-ynyl 2-(4'-((N-(3-fluorophenyl)pentaneamido)methyl)biphenyl-4-yloxy)acetate; N-(3-fluorophenyl)-N-((4'-(prop-2-ynyloxy)biphenyl-4-yl)methyl)pentaneamide; 4'-((N-(2-fluorophenyl)pentaneamido)methyl)biphenyl-4-carboxylic acid; 4'-((N-(4-fluorophenyl)pentaneamido)methyl)biphenyl-4-carboxylic acid; 4'-((N-(2-methoxyphenyl)pentaneamido)methyl)biphenyl-3-carboxylic acid; 4'-((N-(3-methoxyphenyl)pentaneamido)methyl)biphenyl-3-carboxylic acid; 4'-((N-(4-methoxyphenyl)pentaneamido)methyl)biphenyl-3-carboxylic acid; N-((2'-(4-methoxypiperazine-1-carbonyl)biphenyl-4-yl)methyl)-N-phenylpentaneamide; N-((3'-(4-methylpiperazine-1-carbonyl)biphenyl-4-yl)methyl)-N-phenylpentaneamide; 4'-((N-(3-fluorophenyl)pentaneamido)methyl)biphenyl-2-carboxylic acid; 4'-((N-(3-fluorophenyl)pentaneamido)methyl)biphenyl-4-carboxylic acid; N-(3-fluorophenyl)-N-((4'-(morpholine-4-carbonyl)-[1,1'-biphenyl]-4-yl)methyl)pentaneamide; N-(3-fluorophenyl)-N-((4'-(4-methylpiperazine-1-carbonyl)biphenyl-4-yl)methyl)pentaneamide; N-((2'-(1H-tetrazol-5-yl)biphenyl-4-yl)methyl)-N-phenylpentaneamide; N-((4'-methoxybiphenyl-4-yl)methyl)-N-phenylpentaneamide; N-((4'-hydroxybiphenyl-4-yl)methyl)-N-phenylpentaneamide; 2-(4'-((N-phenylpentaneamido)methyl)biphenyl-4-yloxy)acetic acid; N-(3-fluorophenyl)-N-((4'-methoxybiphenyl-4-yl)methyl)pentaneamide; N-(3-fluorophenyl)-N-((4'-hydroxy-[1,1'-biphenyl]-4-yl)methyl)acetamide; 2-((4'-((N-(3-fluorophenyl)acetamido)methyl)-[1,1'-biphenyl]-4-yl)oxy)acetic acid; N-(3-chlorophenyl)-N-((4'-methoxybiphenyl-4-yl)methyl)pentaneamide; N-(3-chlorophenyl)-N-((4'-hydroxybiphenyl-4-yl)methyl)pentaneamide; 2-(4'-((N-(3-chlorophenyl)pentaneamido)methyl)biphenyl-4-yloxy)acetic acid; N-(3-bromophenyl)-N-((4'-methoxybiphenyl-4-yl)methyl)pentaneamide; N-((4'-(hydroxybiphenyl-4-yl)methyl)-N-(3-(trifluoromethyl)phenyl)pentaneamide; 2-(4'-((N-(3-bromophenyl)pentaneamido)methyl)biphenyl-4-yloxy)acetic acid; N-((4'-methoxybiphenyl-4-yl)methyl)-N-(3-(trifluoromethyl)phenyl)pentaneamide; N-((4'-hydroxybiphenyl-4-yl)methyl)-N-(3-nitrophenyl)pentaneamide; 2-(4'-((N-(3-(trifluoromethyl)phenyl)pentaneamido)methyl)biphenyl-4-yloxy)acetic acid; N-((4'methoxybiphenyl-4-yl)methyl)-N-m-tolylpentaneamide; N-((4'-hydroxybiphenyl-4-yl)methyl)-N-m-tolylpentaneamide; 2-(4'-((N-m-tolylpentaneamido)methyl)biphenyl-4-yloxy)acetic acid; N-((4'-hydroxyphenyl-4-yl)methyl)-N-(3-nitrophenyl)pentaneamide; 2-(4'-((N-(3-nitrophenyl)pentaneamido)methyl)biphenyl-4-yloxy)acetic acid; N-(3-iodophenyl)-N-((4'-methoxybiphenyl-4-yl)methyl)pentaneamide; N-((4'-hydroxybiphenyl-4-yl)methyl)-N-(3-iodophenyl)pentaneamide; 2-(4'-((N-(3-iodophenyl)pentaneamido)methyl)biphenyl-4-yloxy)acetic acid; N-(3-fluorophenyl)-N-((4'-hydroxybiphenyl-4-yl)methyl)acetamide; N-(3-fluorophenyl)-N-((4'-hydroxybiphenyl-4-yl)methyl)pentaneamide; 2-(4'-((N-(3-fluorophenyl)pentaneamido)methyl)biphenyl-4-yloxy)acetic acid; N-((4'-(4-isopropylpiperazine-1-carbonyl)biphenyl-4-yl)methyl)-N-phenylpentaneamide; N-(4-fluorophenyl)-N-((4'-(4-isopropylpiperazine-1-carbonyl)-[1,1'-biphenyl]-4-yl)methyl)pentaneamide; N-((3'-(4-isopropylpiperazine-1-carbonyl)biphenyl-4-yl)methyl)-N-phenylpentaneamide; and N-(4-fluorophenyl)-N-((3'-(4-isopropylpiperazine-1-carbonyl)biphenyl-4-yl)methyl)pentaneamide.

The present invention provides a pharmaceutical composition for preventing or treating an inflammatory disease, and the invention includes the novel compound or a pharmaceutically acceptable salt thereof as an active ingredient.

According to an exemplary embodiment of the present invention, the inflammatory disease may be selected from the group consisting of asthma, atherosclerosis, cancer, pruritus, rheumatoid arthritis and inflammatory enteropathy.

According to another exemplary embodiment of the present invention, the composition may inhibit BLT2 activity.

The present invention provides a method for treating an inflammatory disease, which includes administering the pharmaceutical composition to a subject.

The present invention provides a use of the composition including the novel compound or a pharmaceutically acceptable salt thereof to treat an inflammatory disease.

Advantageous Effects

The present invention relates to a new compound exhibiting BLT2 inhibitory activity and a pharmaceutical composition for preventing or treating an inflammatory disease, which includes the compound. The inventors identified a novel compound exhibiting BTL2 inhibitory activity to solve the problems of conventional compounds for treating an inflammatory disease, for example, instability in the living organism and difficulty in mass production, and experimentally confirmed that the compound has excellent effects of improving the death of cancer cells and inhibiting cancer cell metastasis, a chemotactic motility inhibitory effect, and an antiasthma effect, and therefore the compound is expected to be effectively used as a pharmaceutical composition for treating an inflammatory disease.

MODES OF THE INVENTION

Figure 1A:
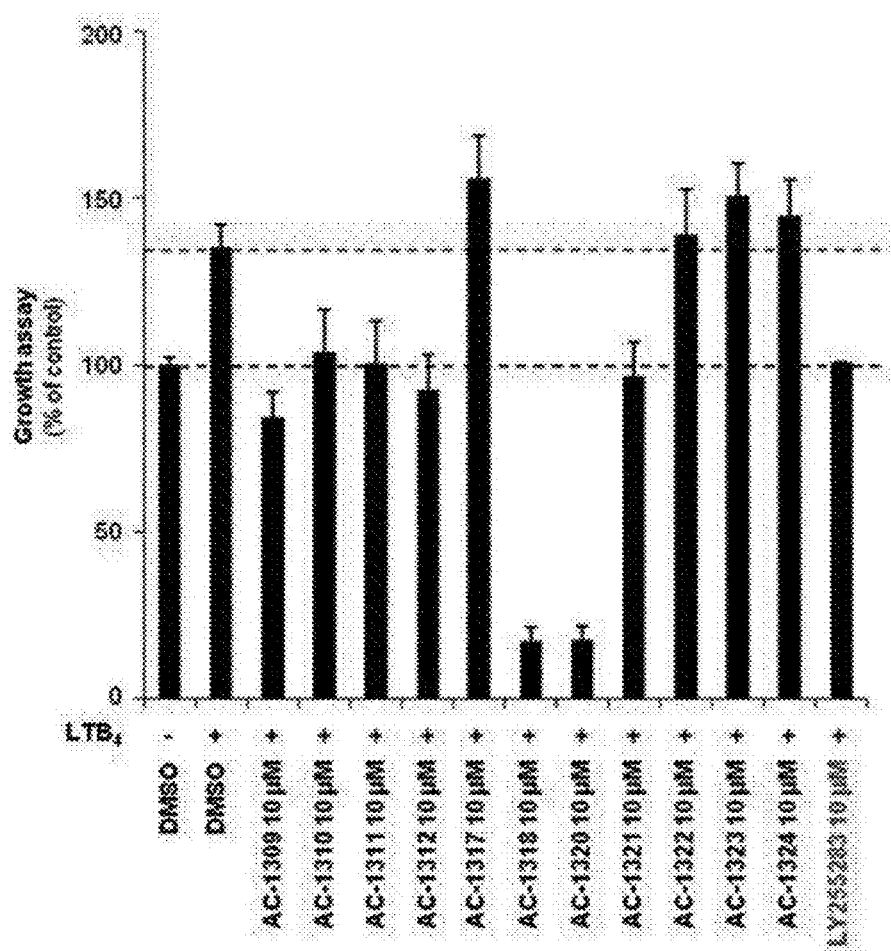
FIGS. 1A to 1D show the confirming results of the growth inhibitory effect of the present novel compound in the BLT2-expressing cells (CHO-BLT2 cells).
Figure 1B:
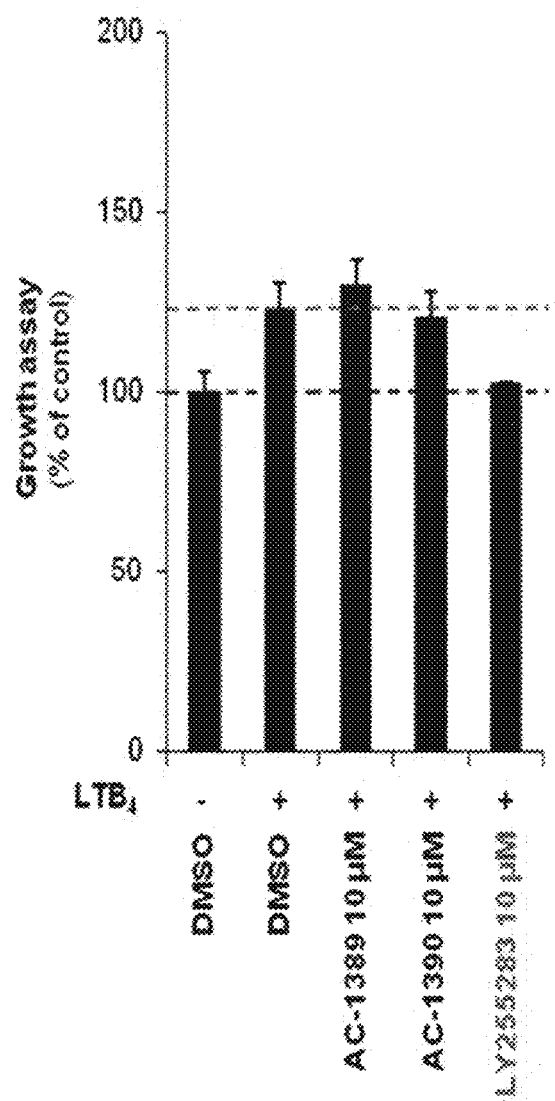
Figure 1C:
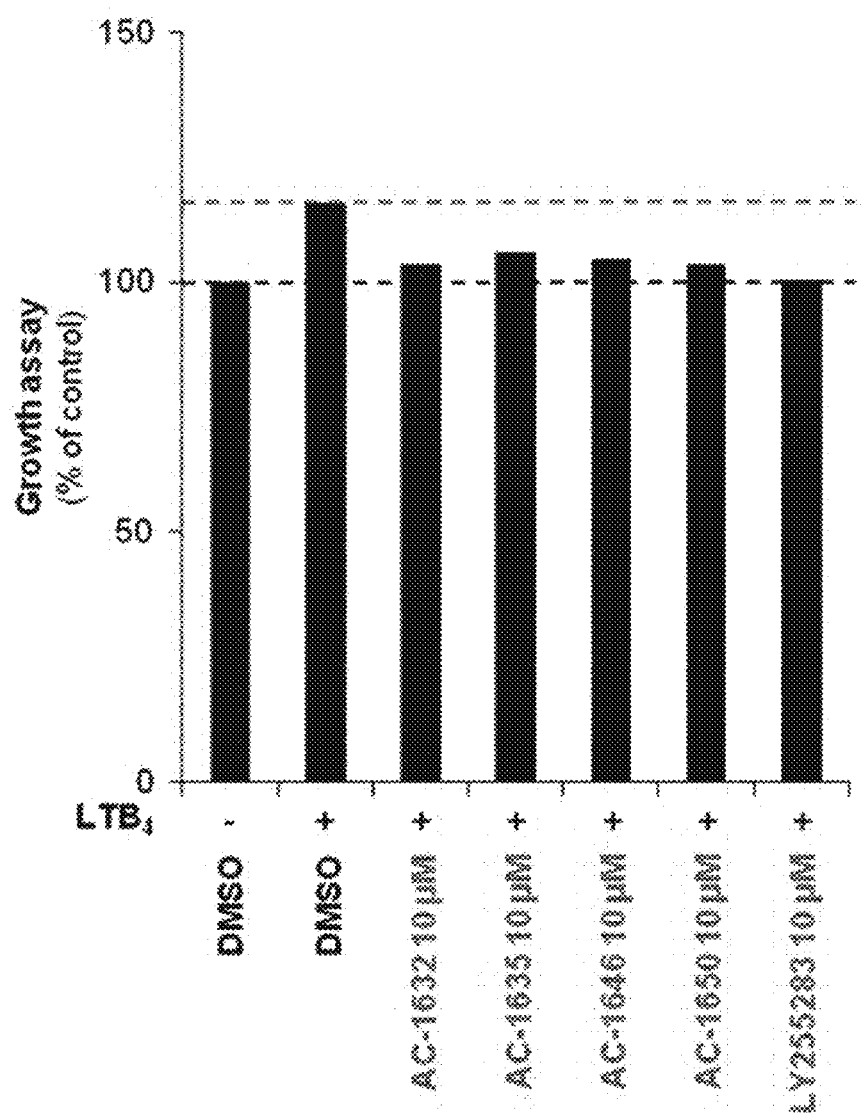
Figure 1D:
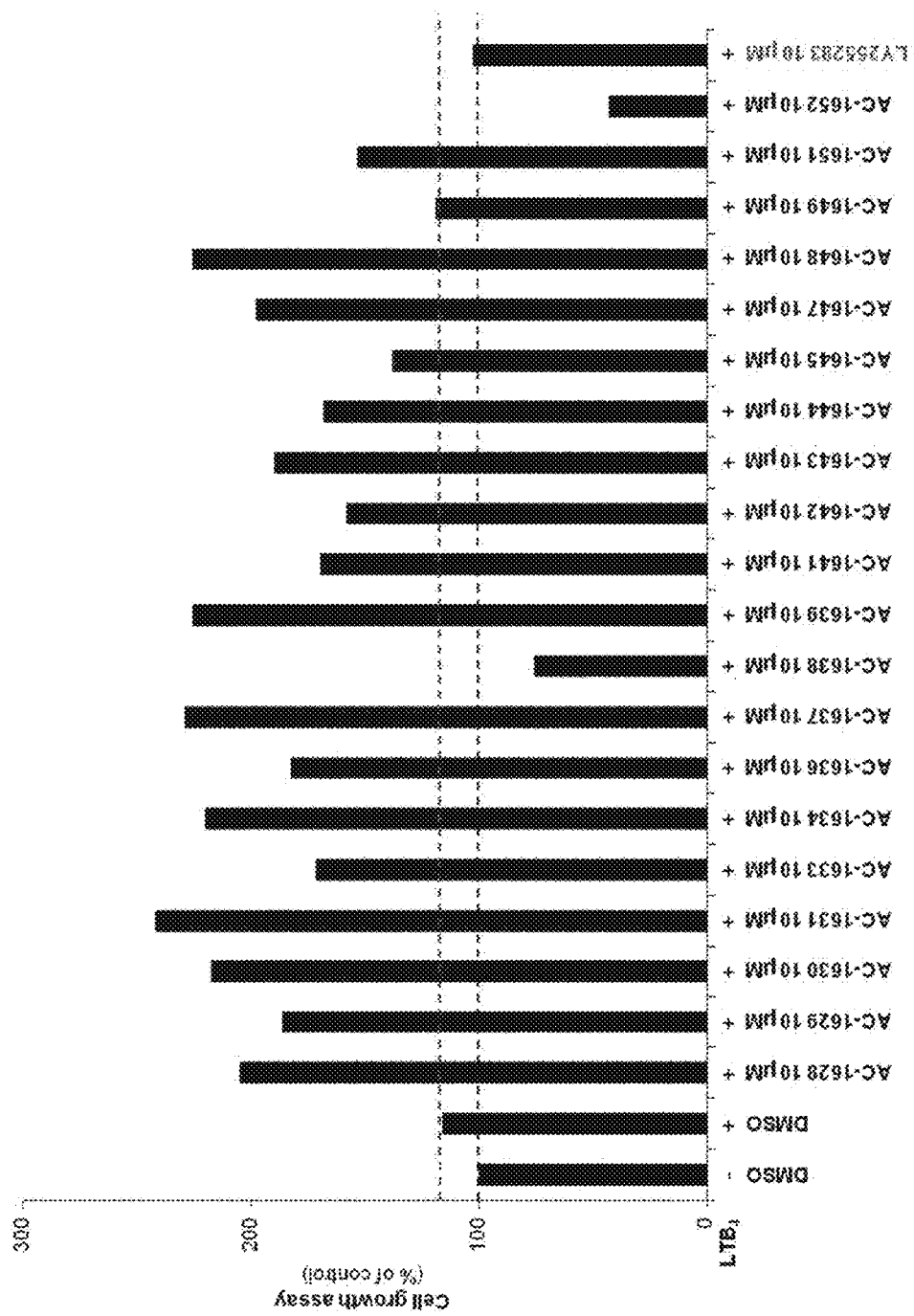

The inventors specifically identified effects of increasing the death of cancer cells, inhibiting cancer cell metastasis and inhibiting BLT2-dependent chemotactic motility, and an antiasthma effect based on the fact that the growth of BLT2-expressing cells can be considerably inhibited when a novel compound prepared in an example is treated, and therefore, the present invention was completed.

Hereinafter, the present invention will be described in detail.

The present invention provides a compound represented by Formula 1 below or a pharmaceutically acceptable salt thereof.

[Formula 1]

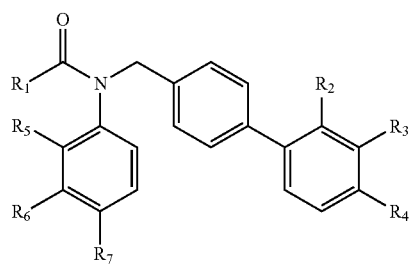

In Formula 1,
R$_1$ is C$_1$ to C$_{10}$ alkyl, or

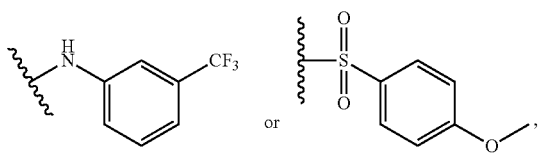 [SMILES: *Nc1cccc(C(F)(F)F)c1 ; *S(=O)(=O)c1ccc(OC)cc1]

R$_2$ is hydrogen,

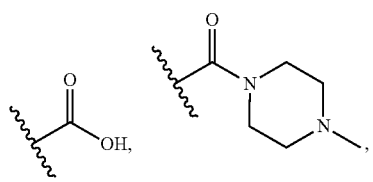

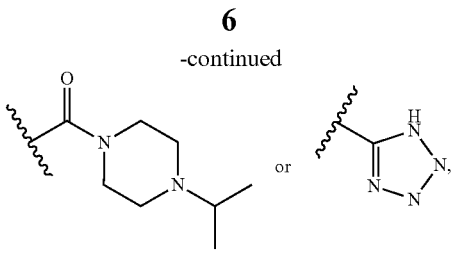

R$_3$ is hydrogen,

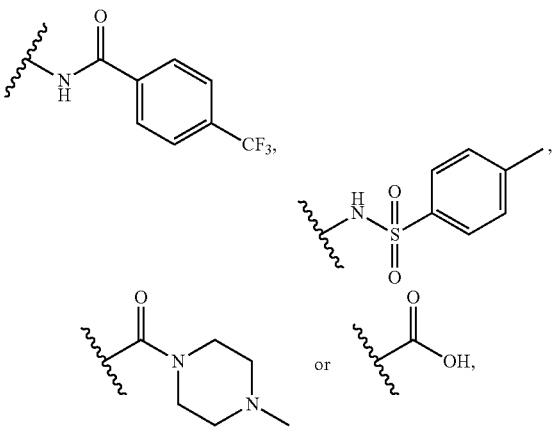

R$_4$ is hydrogen,

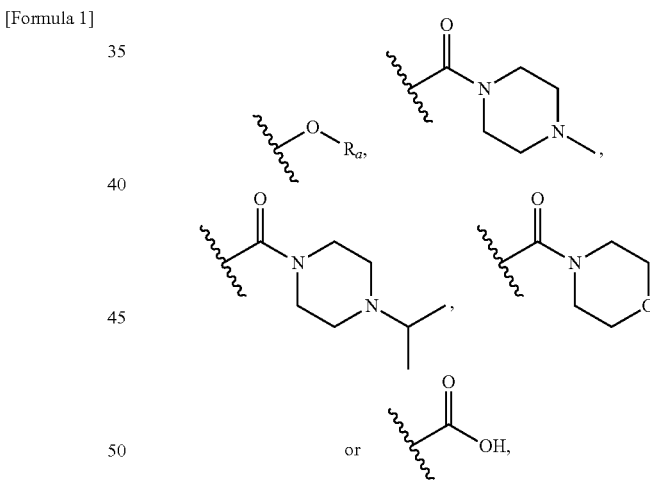

where R$_a$ is hydrogen, C$_1$ to C$_{10}$ alkyl, C$_1$ to C$_5$ carboxyl,

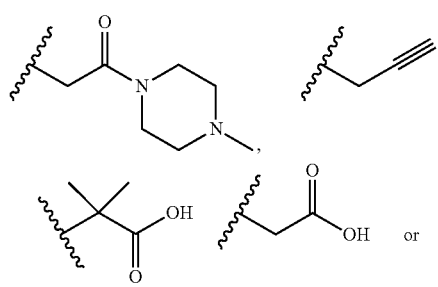

-continued

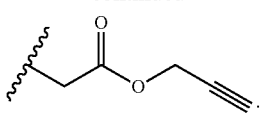

and

R$_5$, R$_6$, and R$_7$ are each independently hydrogen, halogen, nitro, methyl, trifluoromethyl or methoxy.

However, the cases when R$_1$ is butyl, R$_2$ is

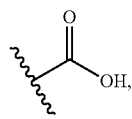

and each of R$_3$, R$_4$, R$_5$, R$_6$, and R$_7$ is hydrogen;
R$_1$ is butyl, R$_3$ is

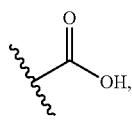

and each of R$_2$, R$_4$, R$_5$, R$_6$, and R$_7$ is hydrogen;
R$_1$ is butyl, R$_4$ is

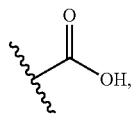 [SMILES: *C(=O)O]

and each of R$_2$, R$_3$, R$_5$, R$_6$, and R$_7$ is hydrogen;
R$_1$ is butyl, R$_4$ is

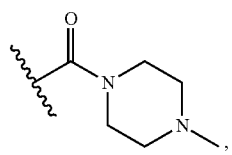 [SMILES: *C(=O)N1CCN(C)CC1]

and each of R$_2$, R$_3$, R$_5$, R$_6$, and R$_7$ is hydrogen;
R$_1$ is butyl, R$_4$ is

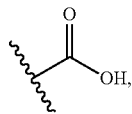

R$_6$ is fluorine, and each of R$_2$, R$_3$, R$_5$, and R$_7$ is hydrogen;

R$_1$ is pentyl, R$_4$ is

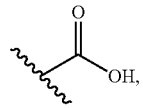 [SMILES: *C(=O)O]

R$_6$ is fluorine, and each of R$_2$, R$_3$, R$_5$, and R$_7$ is hydrogen; and

R$_1$ is pentyl, R$_4$ is

R$_6$ is fluorine, and each of R$_2$, R$_3$, R$_5$, and R$_7$ is hydrogen are excluded.

An exemplary example of the compound represented by Formula 1 according to the present invention is as follows: N-((3'-(4-methylphenylsulfonamido)biphenyl-4-yl) methyl)-N-phenylpentaneamide; N-(4'-((N-phenylpentaneamido)methyl)biphenyl-3-yl)-4-(trifluoromethyl)benzamide; N-(3-fluorophenyl)-N-((3'-(4-methylphenylsulfonamido)biphenyl-4-yl)methyl) pentaneamide; N-(4'-((N-3-fluorophenyl)pentaneamido) methyl)biphenyl-3-yl)-4-(trifluoromethyl)benzamide; 1-(3-fluorophenyl)-1-((4'-methoxybiphenyl-4-yl)methyl)-3-(3-(trifluoromethyl)phenyl)urea; N-(3-fluorophenyl)-N-((4'-methoxybiphenyl-4-yl)methyl)-1-(4-methoxyphenylsulfonyl)methaneamide; 1-(3-fluorophenyl)-1-((4'-hydroxybiphenyl-4-yl)methyl)-3-(3-(trifluoromethyl) phenyl)urea; 2-(4'-((1-(3-fluorophenyl)-3-(3-(trifluoromethyl)phenyl)ureido)methyl)biphenyl-4-yloxy) acetic acid; 4-(4'-((N-(3-fluorophenyl)pentaneamido) methyl)biphenyl-4-yloxy)butanoic acid; 2-(4'-((N-(3-fluorophenyl)pentaneamido)methyl)biphenyl-4-yloxy)-2-methylpropanoic acid; (E)-3-(4'-((N-(3-fluorophenyl) pentaneamido)methyl)biphenyl-4-yloxy)acrylic acid; 3-(4'-((N-(3-fluorophenyl)pentaneamido)methyl)biphenyl-4-yloxy)propanoic acid; N-(3-fluorophenyl)-N-((4'-(2-(4-methylpiperazine-1-yl)-2-oxoethoxy)biphenyl-4-yl)methyl) pentaneamide; prop-2-ynyl 2-(4'-((N-(3-fluorophenyl) pentaneamido)methyl)biphenyl-4-yloxy)acetate; N-(3-fluorophenyl)-N-((4'-(prop-2-ynyloxy)biphenyl-4-yl) methyl)pentaneamide; 4'-((N-(2-fluorophenyl) pentaneamido)methyl)biphenyl-4-carboxylic acid; 4'-((N-(4-fluorophenyl)pentaneamido)methyl)biphenyl-4-carboxylic acid; 4'-((N-(2-methoxyphenyl)pentaneamido) methyl)biphenyl-3-carboxylic acid; 4'-((N-(3-methoxyphenyl)pentaneamido)methyl)biphenyl-3-carboxylic acid; 4'-((N-(4-methoxyphenyl)pentaneamido) methyl)biphenyl-3-carboxylic acid; N-((2'-(4-methoxypiperazine-1-carbonyl)biphenyl-4-yl)methyl)-N-phenylpentaneamide; N-((3'-(4-methylpiperazine-1-carbonyl)biphenyl-4-yl)methyl)-N-phenylpentaneamide; 4'-((N-(3-fluorophenyl)pentaneamido)methyl)biphenyl-2-carboxylic acid; 4'-((N-(3-fluorophenyl)pentaneamido) methyl)biphenyl-4-carboxylic acid; N-(3-fluorophenyl)-N-((4'-(morpholine-4-carbonyl)-[1,1'-biphenyl]-4-yl)methyl) pentaneamide; N-(3-fluorophenyl)-N-((4'-(4-methylpiperazine-1-carbonyl)biphenyl-4-yl)methyl) pentaneamide; N-((2'-(1H-tetrazol-5-yl)biphenyl-4-yl) methyl)-N-phenylpentaneamide; N-((4'-methoxybiphenyl- 4-yl)methyl)-N-phenylpentaneamide; N-((4'-hydroxybiphenyl-4-yl)methyl)-N-phenylpentaneamide; 2-(4'-((N-phenylpentaneamido)methyl)biphenyl-4-yloxy) acetic acid; N-(3-fluorophenyl)-N-((4'-methoxybiphenyl-4-yl)methyl)pentaneamide; N-(3-fluorophenyl)-N-((4'-hydroxy-[1,1'-biphenyl]-4-yl)methyl)acetamide; 2-((4'-((N-(3-fluorophenyl)acetamido)methyl)-[1,1'-biphenyl]-4-yl)oxy) acetic acid; N-(3-chlorophenyl)-N-((4'-methoxybiphenyl-4-yl)methyl)pentaneamide; N-(3-chlorophenyl)-N-((4'-hydroxybiphenyl-4-yl)methyl)pentaneamide; 2-(4'-((N-(3-chlorophenyl)pentaneamido)methyl)biphenyl-4-yloxy) acetic acid; N-(3-bromophenyl)-N-((4'-methoxybiphenyl-4-yl)methyl)pentaneamide; N-((4'-(hydroxybiphenyl-4-yl)methyl)-N-(3-(trifluoromethyl)phenyl)pentaneamide; 2-(4'-((N-(3-bromophenyl)pentaneamido)methyl)biphenyl-4-yloxy)acetic acid; N-((4'-methoxybiphenyl-4-yl)methyl)-N-(3-(trifluoromethyl)phenyl)pentaneamide; N-((4'-hydroxybiphenyl-4-yl)methyl)-N-(3-nitrophenyl) pentaneamide; 2-(4'-((N-(3-(trifluoromethyl)phenyl) pentaneamido)methyl)biphenyl-4-yloxy)acetic acid; N-((4'methoxybiphenyl-4-yl)methyl)-N-m-tolylpentaneamide; N-((4'-hydroxyphenyl-4-yl)methyl)-N-m-tolylpentaneamide; 2-(4'-((N-m-tolylpentaneamido)methyl)biphenyl-4-yloxy)acetic acid; N-((4'-hydroxybiphenyl-4-yl)methyl)-N-(3-nitrophenyl)pentaneamide; 2-(4'-((N-(3-nitrophenyl) pentaneamido)methyl)biphenyl-4-yloxy)acetic acid; N-(3-iodophenyl)-N-((4'-methoxybiphenyl-4-yl)methyl) pentaneamide; N-((4'-hydroxybiphenyl-4-yl)methyl)-N-(3-iodophenyl)pentaneamide; 2-(4'-((N-(3-iodophenyl) pentaneamido)methyl)biphenyl-4-yloxy)acetic acid; N-(3-fluorophenyl)-N-((4'-hydroxybiphenyl-4-yl)methyl) acetamide; N-(3-fluorophenyl)-N-((4'-hydroxybiphenyl-4-yl)methyl)pentaneamide; 2-(4'-((N-(3-fluorophenyl) pentaneamido)methyl)biphenyl-4-yloxy)acetic acid; N-((4'-(4-isopropylpiperazine-1-carbonyl)biphenyl-4-yl)methyl)-N-phenylpentaneamide; N-(4-fluorophenyl)-N-((4'-(4-isopropylpiperazine-1-carbonyl)-[1,1'-biphenyl]-4-yl) methyl)pentaneamide; N-((3'-(4-isopropylpiperazine-1-carbonyl)biphenyl-4-yl)methyl)-N-phenylpentaneamide; and N-(4-fluorophenyl)-N-((3'-(4-isopropylpiperazine-1-carbonyl)biphenyl-4-yl)methyl)pentaneamide.

The term "pharmaceutically acceptable" used herein refers to a compound or composition that is suitable to be used in contact with a subject's (e.g., a human) tissue due to a reasonable benefit/risk ratio without excessive toxicity, irritation, allergic reactions, or other problems or complications, and included within the scope of sound medical judgment.

The term "salt" used herein is an acid addition salt formed by a pharmaceutically acceptable free acid. The acid addition salt is obtained from inorganic acids such as hydrochloric acid, nitric acid, phosphoric acid, sulfuric acid, hydrogen bromide, hydrogen iodide, nitride and phosphorous acid, and non-toxic organic acids such as aliphatic mono and dicarboxylates, phenyl-substituted alkanoates, hydroxyl alkanoates and alkandioates, aromatic acids, aliphatic and aromatic sulfonic acids. Such pharmaceutically non-toxic salts include sulfates, pyrosulfates, bisulfates, sulfites, bisulfites, nitrates, phosphates, monohydrogen phosphates, dihydrogen phosphates, metaphosphates, pyrophosphate chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methylbenzoates, dinitrobenzoates, hydroxylbenzoates, methoxybenzoates, phthalates, terephthalates, benzenesulfonates, toluenesulfonates, chlorobenzenesulfonates, xylenesulfonates, phenylacetates, phenylpropionates, phenylburyrates, citrates, lactates, β-hydroxylbutyrates, glycolates, malates, tartrates, methanesulfonates, propanesulfonates, naphthalene-1-sulfonates, naphthalene-2-sulfonates, and mandelates.

The acid addition salt according to the present invention may be prepared by a conventional method, for example, dissolving the compound represented by Formula 1 in an excessive acid aqueous solution, and precipitating the resulting salt using a water-miscible organic solvent, for example, methanol, ethanol, acetone or acetonitrile. In addition, the acid addition salt according to the present invention may be prepared by evaporating a solvent or an excessive acid from this mixture, and then dehydrating the resulting mixture or suction-filtrating a precipitated salt.

In addition, the pharmaceutically acceptable metal salt may be prepared using a base. An alkali metal or alkali earth metal salt may be obtained by, for example, dissolving a compound in an excessive amount of an alkali metal hydroxide or alkali earth metal hydroxide solution, filtering an insoluble compound salt, and dehydrating the remaining solution through evaporation. Here, a sodium, potassium or calcium salt is pharmaceutically appropriate for the metal salt. Also, a silver salt corresponding to the metal salt is obtained by a reaction between an alkali metal or alkali earth metal salt and a suitable silver salt (e.g., silver nitrate).

In an exemplary embodiment of the present invention, novel compounds exhibiting a BLT2 inhibitory activity were prepared (see Examples 1 to 57), and it was confirmed that the growth of BLT2-expressing cells were inhibited by the treatment of the novel compound (see Experimental Example 2). In addition, it was confirmed that the present compounds can enhance the cancer cell death by co-treating with an anti-cancer agent, cisplatin, and the compounds inhibit the chemotactic motility of the BLT2-expressing cells (see Experimental Examples 3 and 4). It was also confirmed that the present compounds have an inhibitory property on the binding affinity between LTB4 and BLT2. (see Experimental Example 5). An experiment carried out by inventors specifically showed that the present compounds contain the reducing property on the airway hyperresponsiveness (AHR) and the inhibitory property on IL-4 production in asthma-induced mice (see Experimental Example 6). All the results mentioned above strongly suggest that the present compounds can be used effectively as a pharmaceutical composition for the inflammatory-related diseases.

Therefore, the present invention provides a pharmaceutical composition for preventing or treating an inflammatory disease, which includes the compound or a pharmaceutically acceptable salt thereof.

The term "prevention" used herein refers to all actions of inhibiting an inflammatory disease or delaying the onset thereof by administration of the pharmaceutical composition according to the present invention.

The term "treatment" used herein refers to all actions involved in alleviating or beneficially changing symptoms of an inflammatory disease by administration of the pharmaceutical composition according to the present invention.

In the present invention, the inflammatory disease is a disease caused by the overexpression of BLT2, and may be one or more selected from asthma, atherosclerosis, cancer, pruritus, rheumatoid arthritis and inflammatory enteropathy, but the present invention is not limited thereto. Other than the diseases presented in the specification, all BLT2-associated inflammatory diseases known in the art are included as inflammatory diseases which can be prevented or treated with a compound having the structure of Formula 1 of the present invention. In a particular example, the cancer may be any cancer caused by the overexpression of BLT2 or Ras, which is a tumor gene. The cancer may be, but is not limited to, selected from the group consisting of kidney cancer, prostatic cancer, pancreatic cancer, breast cancer, brain tumors, skin cancer and liver cancer.

In the present invention, BLT2, a member of the G protein-coupled receptor (GPCR) family, is a receptor having low affinity to $LTB_4$, and therefore the composition of the present invention inhibits cell growth caused by BLT2 to prevent or treat an inflammatory disease. More specifically, $LTB_4$-induced chemotactic motility may be inhibited by inhibiting the production of ROS induced by BLT2 activity.

The term "inhibition" used herein refers to inhibition of a certain step among gene transcription, mRNA processing, translation, translocation and maturation, or inhibition of binding between proteins, activation of a protein or signal transduction there through.

The pharmaceutical composition of the present invention may include a pharmaceutically acceptable carrier in addition to an active ingredient. Here, the pharmaceutically acceptable carrier is conventionally used in formulation, and includes, but is not limited to, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil. In addition, other than the components, a lubricant, a wetting agent, a sweetening agent, a flavoring agent, an emulsifier, a suspending agent or a preservative may be further included.

The pharmaceutical composition of the present invention may be administered orally or parenterally (e.g., intravenously, subcutaneously, intraperitoneally or locally) depending on a desired method, and a dosage of the pharmaceutical composition may vary depending on the condition and body weight of a patient, the severity of a disease, a drug type, an administration route and time, and may be suitably selected by one of ordinary skill in the art.

The pharmaceutical composition of the present invention is administered at a pharmaceutically effective amount. The "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered alone or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

Specifically, the effective amount of the pharmaceutical composition of the present invention may be dependent on a patient's age, sex, condition and body weight, an absorption rate of the active ingredient in the body, an inactivation rate, an excretion rate, a type of disease, or a drug used in combination, and may be generally administered at 0.001 to 150 mg, and preferably 0.01 to 100 mg per kg of body weight daily or every other day, or divided into one or three daily administrations. However, the effective amount may vary depending on an administration route, the severity of obesity, sex, body weight or age, and therefore, the scope of the present invention is not limited by the dose in any way.

In addition, the present invention provides a method for treating an inflammatory disease, which includes administering the pharmaceutical composition to a subject. The term "subject" refers to a target disease to be treated, and more specifically, a mammal such as a human, or a non-human primate, a mouse, a rat, a dog, a cat, a horse and a cow.

Hereinafter, in order to help understanding the present invention, the exemplary embodiments will be disclosed. Although the following examples are made merely to provide for easier understanding of the present invention, the scope of the present invention is not limited to the examples.

EXAMPLES

Example 1. Preparation of N-((3'-(4-methylphenyl-sulfonamido)biphenyl-4-yl)methyl)-N-phenylpenta-neamide (AC-1079)

Step 1: Preparation of 3'-nitrobiphenyl-4-carbaldehyde

3-Bromonitrobenzene (1.0 equiv) and 4-formylphenylboronic acid (1.1 equiv) were thoroughly mixed with RBF, and dissolved in a 1,4-dioxane:$H_2O$ (10:1) mixed solution. Degassing was performed for 20 minutes by adding Pd(dppf)$Cl_2$.DCM (0.01 equiv) to the mixed solution, and performed again for 20 minutes by adding $Na_2CO_3$. After degassing again for 15 minutes, the resulting solution was refluxed for 3 hours. After the reaction, the mixture was filtered with ethyl acetate (EA), extracted, dehydrated with anhydrous $MgSO_4$, concentrated by evaporation, and purified by medium pressure liquid chromatography (MPLC), thereby obtaining 3'-nitrobiphenyl-4-carbaldehyde (91% yield).

Step 2: Preparation of N-((3'-nitrobiphenyl-4-yl)methyl)aniline

The 3'-nitrobiphenyl-4-carbaldehyde (1.0 equiv) obtained in Step 1 and aniline (3.0 equiv) were dissolved in methanol, and then stirred at room temperature for 4 hours. A reaction performed until an imine was formed, and then it was observed by thin layer chromatography (TLC), and after the imine was formed, a methanol solution in which 1M NaCNBH$_3$ (1.0 equiv) and 0.5M ZnCl$_2$ (1.0 equiv) were mixed was added to the solution, followed by stirring at room temperature overnight. After the reaction, the methanol was removed under a vacuum, and the remaining solution was diluted with ethyl acetate (EA), and the organic solvent layer was washed with brine, dehydrated with anhydrous magnesium sulfate (MgSO$_4$) and concentrated by evaporation. The concentrate was purified by MPLC, thereby obtaining N-((3'-nitrobiphenyl-4-yl)methyl)aniline (79% yield).

Step 3: Preparation of N-((3'-nitrobiphenyl-4-yl)methyl)-N-phenylpentaneamide

The N-((3'-nitrobiphenyl-4-yl)methyl)aniline obtained in Step 2 was dissolved in dichloromethane (DCM), mixed with triethanolamine (TEA), and cooled on ice. Valeroyl chloride (3.0 equiv) was added to the mixed solution, and stirred at room temperature for 4 hours. After the reaction, RBF was added, and the organic solvent layer was washed with brine and separated. Afterward, the organic solvent layer was collected and dehydrated with anhydrous magnesium sulfate ($MgSO_4$), filtered, and concentrated by evaporation. The concentrate was purified by MPLC, thereby obtaining N-((3'-nitrobiphenyl-4-yl)methyl)-N-phenylpentanamide (88% yield).

Step 4: Preparation of N-((3'-aminobiphenyl-4-yl) methyl)-N-phenylpentaneamide

The N-((3'-nitrobiphenyl-4-yl)methyl)-N-phenylpentaneamide (1.0 equiv) obtained in Step 3 was thoroughly mixed with RBF, and methanol was added. After RBF was cooled, 10% Pd/C (20 wt %) was added, and the mixed solution was stirred at room temperature under an $H_2$-supplying condition for overnight. After the reaction, the resulting solution was filtered using a silica pad, and concentrated by evaporation. The concentrate was purified by MPLC, thereby obtaining N-((3'-aminobiphenyl-4-yl)methyl)-N-phenylpentaneamide (92% yield).

Step 5: Preparation of N-((3'-(4-methylphenylsulfonamido)biphenyl-4-yl)methyl)-N-phenylpentaneamide The N-((3'-aminobiphenyl-4-yl)methyl)-N-phenylpentaneamide (1.0 equiv) obtained in Step 4 and triethylamine (2.0 equiv) were dissolved in a dichloromethane (DCM) solution, and cooled on ice. Afterward, 4-methoxybenzene sulfonyl chloride (1.5 equiv) was added, and then stirred at room temperature overnight. After the reaction, the resulting solution was concentrated by evaporating DCM. The concentrate was purified by column chromatography, thereby obtaining the final product, N-((3'-(4-methylphenylsulfonamido)biphenyl-4-yl)methyl)-N-phenylpentanamide (25% yield).

$^1$H-NMR ($CDCl_3$, 400 MHz) δ 7.67 (2H, d, J=8.0 Hz); 7.39-7.31 (7H, m); 7.23 (3H, d, J=8.4 Hz); 7.01 (3H, d, J=8.4 Hz); 6.54 (1H, s); 4.90 (2H, s); 2.38 (3H, s); 2.09 (2H, t); 1.61-1.56 (2H, m); 1.26-1.20 (2H, m); 0.82 (3H, t).

Example 2. Preparation of N-(4'-((N-phenylpentaneamido)methyl)biphenyl-3-yl)-4-(trifluoromethyl) benzamide (AC-1310)

The N-((3'-aminobiphenyl-4-yl)methyl)-N-phenylpentaneamide obtained in Step 4 of Example 1, trifluoromethyl-p-toluic acid (1.2 equiv), EDC (1.2 equiv), HOBt (1.2 equiv), and N,N-diisopropylethylamine (DIPEA) (1.2 equiv) were dissolved in a dichloromethane (DCM) solution, and stirred at room temperature overnight. At the end of the reaction, water was added. A water-soluble layer was extracted with ethyl acetate (EA), and an organic solvent layer was filtered and concentrated by evaporation. The concentrate was purified by column chromatography, thereby obtaining a final product, N-(4'-((N-phenylpentaneamido)methyl)biphenyl-3-yl)-4-(trifluoromethyl)benzamide (25% yield).

$^1$H-NMR ($CDCl_3$, 400 MHz) δ 8.45 (1H, s); 8.03 (2H, d, J=8.0 Hz); 7.89 (1H, s); 7.73 (2H, d, J=8.4 Hz); 7.67 (1H, d, J=7.6 Hz); 7.49 (2H, d, J=8.0 Hz); 7.44-7.38 (2H, m); 7.36-7.31 (3H, m); 7.238 (2H, d, J=8.4 Hz); 7.00-6.98 (2H, m); 4.89 (2H, s); 2.06 (2H, t); 1.58-1.54 (2H, m); 1.23-1.169 (2H, m); 0.78 (3H, t).

Example 3. Preparation of N-(3-fluorophenyl)-N-((3'-(4-methylphenylsulfonamido)biphenyl-4-yl) methyl)pentaneamide (AC-1080)

Step 1: Preparation of 3-fluoro-N-((3'-nitrobiphenyl-4-yl)methyl)aniline

The 3'-nitrobiphenyl-4-carbaldehyde (1.0 equiv) obtained in Step 1 of Example 1 and 3-fluoroaniline (3-fluoroaniline) (3.0 equiv) were dissolved in methanol, stirred at room temperature for 4 hours. The reaction performed until an imine was formed was observed by thin layer chromatography (TLC), and after the imine was formed, a methanol solution in which 1M $NaCNBH_3$ (1.0 equiv) and 0.5M $ZnCl_2$ (1.0 equiv) were mixed was added to the solution, followed by stirring at room temperature overnight. After the reaction, the methanol was removed under a vacuum, a remaining solution was diluted with ethyl acetate (EA), and an organic solvent layer was washed with brine, dehydrated with anhydrous magnesium sulfate ($MgSO_4$) and concentrated by evaporation. The concentrate was purified by MPLC, thereby obtaining 3-fluoro-N-((3'-nitrobiphenyl-4-yl)methyl)aniline (81% yield).

Step 2: Preparation of N-(3-fluorophenyl)-N-((3'-nitrobiphenyl-4-yl)methyl)pentaneamide The 3-fluoro-((3'-nitrobiphenyl-4-yl)methyl)aniline obtained in Step 1 was dissolved in dichloromethane (DCM), mixed with triethanolamine (TEA), and cooled on ice. Valeroyl chloride (3.0 equiv) was added to the mixed solution, and stirred at room temperature for 4 hours. After the reaction, RBF was added, and the organic solvent layer was washed with brine and the separated. Afterward, the organic solvent layer was collected, dehydrated with anhydrous magnesium sulfate ($MgSO_4$), filtered, and concentrated by evaporation. The concentrate was purified by MPLC, thereby obtaining N-(3-fluorophenyl)-N-((3'-nitrobiphenyl-4-yl)methyl)pentaneamide (87% yield).

Step 3: Preparation of N-((3'-aminobiphenyl-4-yl) methyl)-N-(3-fluorophenyl)pentaneamide The N-(3-fluorophenyl)-N-((3'-nitrobiphenyl-4-yl) methyl)pentaneamide (1.0 equiv) obtained in Step 2 was thoroughly mixed with RBF, and mixed with methanol. After RBF was cooled, 10% Pd/C (20 wt %) was added, and the mixed solution was stirred at room temperature under an $H_2$-supplying condition overnight. After the reaction, the resulting solution was filtered using a silica pad, and concentrated by evaporation. The concentrate was purified by MPLC, thereby obtaining N-((3'-aminobiphenyl-4-yl) methyl)-N-(3-fluorophenyl)pentanamide (89% yield).

Step 4: Preparation of N-(3-fluorophenyl)-N-((3'-(4-methylphenylsulfonamido)biphenyl-4-yl)methyl) pentaneamide The N-((3'-aminobiphenyl-4-yl)methyl)-N-(3-fluorophenyl)pentaneamide (1.0 equiv) obtained in Step 3 and triethylamine (2.0 equiv) were dissolved in a dichloromethane (DCM) solution, and cooled on ice. Afterward, 4-methoxybenzene sulfonyl chloride (1.5 equiv) was added, and then stirred at room temperature overnight. After the reaction, the resulting solution was concentrated by evaporating DCM. The concentrate was purified by column chromatography, thereby obtaining a final product, N-(3-fluorophenyl)-N-((3'-(4-methylphenylsulfonamido)biphenyl-4-yl)methyl)pentanamide (25% yield).

$^1$H-NMR (CDCl$_3$, 400 MHz) δ 7.67 (2H, d, J=8.0 Hz); 7.39-7.31 (7H, m); 7.23 (3H, d, J=8.4 Hz); 7.01 (3H, d, J=8.4 Hz); 6.54 (1H, s); 4.90 (2H, s); 2.38 (3H, s); 2.09 (2H, t); 1.61-1.56 (2H, m); 1.26-1.20 (2H, m); 0.82 (3H, t).

Example 4. Preparation of N-(4'-((N-(3-fluorophenyl)pentaneamido)methyl)biphenyl-3-yl)-4-(trifluoromethyl)benzamide (AC-1311)

The N-((3'-aminobiphenyl-4-yl)methyl)-N-(3-fluorophenyl)pentaneamide obtained in Step 3 of Example 3, trifluromethyl-p-toluic acid (1.2 equiv), EDC (1.2 equiv), HOBt (1.2 equiv), and N,N-diisopropylethylamine (DIPEA) (1.2 equiv) were dissolved in a dichloromethane (DCM) solution, and stirred at room temperature overnight. At the end of the reaction, water was added. A water-soluble layer was extracted with ethyl acetate (EA), and an organic solvent layer was filtered and concentrated by evaporation. The concentrate was purified by column chromatography, thereby obtaining a final product, N-(4'-((N-3-fluorophenyl)pentaneamido)methyl)biphenyl-3-yl)-4-(trifluoromethyl)benzamide (25% yield).

$^1$H-NMR (CDCl$_3$, 400 MHz) δ 8.20 (1H, br, s); 8.03 (2H, d, J=8.4 Hz); 7.89 (1H, m); 7.76 (2H. d. J=8.0 Hz); 7.65 (1H, d, J=8.0 Hz); 7.51 (2H, d, J=8.0 Hz); 7.46-738 (2H, m); 7.34-7.28 (1H, m); 7.25 (2H, d, J=8.4 Hz); 7.06-7.02 (1H, m); 6.81-6.74 (2H, m); 4.90 (2H, s); 2.08 (2H. t); 1.64-1.55 (2H, m); 1.33-1.19 (2H, m); 0.84 (3H, t).

Example 5. Preparation of 1-(3-fluorophenyl)-1-((4'-methoxybiphenyl-4-yl)methyl)-3-(3-(trifluoromethyl)phenyl)urea (AC-1317)

Step 1: Preparation of 4'-methoxybiphenyl-4-carbaldehyde

4-Bromoanisole (1.0 equiv) and 4-formylphenylboronic acid (1.1 equiv) were thoroughly mixed with RBF, and dissolved in a 1,4-dioxane:H$_2$O (10:1) mixed solution. Degassing was performed for 20 minutes by adding Pd(dppf)Cl$_2$.DCM (0.01 equiv) to the mixed solution, and performed again for 20 minutes by adding Na$_2$CO$_3$. After degassing again for 15 minutes, the resulting solution was refluxed for 3 hours. After the reaction, the mixture was filtered with ethyl acetate (EA), extracted, dehydrated with anhydrous MgSO$_4$, concentrated by evaporation, and purified by MPLC, thereby obtaining 4'-methoxybiphenyl-4-carbaldehyde (63% yield).

Step 2: Preparation of 3-fluoro-N-((4'-methoxybiphenyl-4-yl)methyl)aniline

The 4-methoxybiphenyl-4-carbaldehyde (1.0 equiv) obtained in Step 1 and 3-fluoroaniline (3.0 equiv) were dissolved in methanol, and stirred at room temperature for 4 hours. A reaction performed until an imine was formed was observed by TLC, and after the imine was formed, a methanol solution in which 1M NaCNBH$_3$ (1.0 equiv) and 0.5M ZnCl$_2$ (1.0 equiv) were mixed was added to the solution, followed by stirring at room temperature overnight. After the reaction, the methanol was removed under a vacuum, a remaining solution was diluted with ethyl acetate (EA), and an organic solvent layer was washed with brine, dehydrated with anhydrous magnesium sulfate (MgSO$_4$) and concentrated by evaporation. The concentrate was purified by MPLC, thereby obtaining 3-fluoro-N-((4'-methoxybiphenyl-4-yl)methyl)aniline (63% yield).

Step 3: Preparation of 1-(3-fluorophenyl)-1-((4'-methoxybiphenyl-4-yl)methyl)-3-(3-(trifluoromethyl)phenyl)urea The 3-fluoro-N-((4-methoxybiphenyl-4-yl)methyl)aniline obtained in Step 2 was dissolved in a tetrahydrofuran (THF) solution and mixed with trifluoromethylphenyl isocyanate (1.0 equiv), and the mixed solution was stirred overnight. After the reaction, silica was added to adsorb RBF and a crude product, and the resulting mixture was purified by MPLC, thereby obtaining a final product, 1-(3-fluorophenyl)-1-((4'-methoxybiphenyl-4-yl)methyl)-3-(3-(trifluoromethyl)phenyl)urea (23.4% yield).

$^1$H-NMR (CDCl$_3$, 400 MHz) δ 7.61 (1H, s); 7.53-7.48 (5H, m); 7.45-7.35 (2H, m); 7.32-7.29 (3H, m); 7.14-7.09 (1H, m); 7.02 (1H, d, J=8.4 Hz); 6.96 (3H, d, J=8.8 Hz); 6.32 (1H, s, br); 4.96 (2H, s); 3.85 (3H, s).

Example 6. Preparation of N-(3-fluorophenyl)-N-((4'-methoxybiphenyl-4-yl)methyl)-1-(4-methoxyphenylsulfonyl)methaneamide (AC-1312)

The 3-fluoro-N-((4-methoxybiphenyl-4-yl)methyl)aniline obtained in Step 2 of Example 5 and triethanolamine (TEA) (2.0 equiv) were dissolved in RBF, and mixed with DCM. The mixed solution was stirred at 0° C. and cooled. Afterward, 4-methoxybenzen-1-sulfonyl chloride (1.5 equiv) was added, and stirred at room temperature overnight. The mixed solution was concentrated by evaporating DCM under a vacuum. The concentrate was purified by MPLC, thereby obtaining a final product, N-(3-fluorophenyl)-N-((4'-methoxybiphenyl-4-yl)methyl)-1-(4-methoxyphenylsulfonyl)methaneamide (61% yield).

$^1$H-NMR (CDCl$_3$, 400 MHz) δ 7.62-7.59 (2H, m); 7.48-7.45 (2H, m); 7.43 (2H, d, J=8.0 Hz); 7.26 (2H, d, J=0.8 Hz); 7.21-7.15 (1H, m); 6.99-6.89 (5H, m); 6.85-6.83 (1H, m); 6.79-6.76 (1H, m); 4.72 (2H, s); 3.91 (3H, s); 3.83 (3H, s).

Example 7. Preparation of 1-(3-fluorophenyl)-1-((4'-hydroxybiphenyl-4-yl)methyl)-3-(3-(trifluoromethyl)phenyl)urea (AC-1318)

The 1-(3-fluorophenyl)-1-((4'-methoxybiphenyl-4-yl)methyl)-3-(3-(trifluoromethyl)phenyl)urea (1.0 equiv) obtained in Example 5 was dissolved in a dichloromethane (DCM) solution, and cooled on ice. At 0° C., BBr$_3$ was slowly added, and the mixed solution was stirred at room temperature for 3 hours. The reaction was observed by TLC. After the reaction, ice was added to RBF, and extraction was performed with DCM. An organic solvent layer was separated, dehydrated with anhydrous magnesium sulfate (MgSO$_4$), filtered and then concentrated by evaporation. The concentrate was purified by MPLC, thereby obtaining a final product, 1-(3-fluorophenyl)-1-((4'-hydroxybiphenyl-4-yl)methyl)-3-(3-(trifluoromethyl)phenyl)urea (55% yield).

$^1$H-NMR (CDCl$_3$, 400 MHz) δ 7.60 (1H, s); 7.53 (1H, d, J=7.4 Hz); 7.48-7.45 (4H, m); 7.43-7.35 (2H, m); 7.31 (3H, d, J=8.0 Hz); 7.14-7.09 (1H, m); 7.02 (1H, d, J=8.0 Hz); 6.98-6.95 (1H, m); 6.91-6.88 (2H, m); 6.33 (1H, s); 4.96 (2H, s); 4.85 (1H, s).

Example 8. Preparation of 2-(4'-((1-(3-fluorophenyl)-3-(3-(trifluoromethyl)phenyl)ureido)methyl) biphenyl-4-yloxy)acetic acid (AC-1320)

Step 1: Preparation of ethyl-2-(4'-((1-(3-fluorophenyl)-3-(3-(trifluoromethyl)phenyl)ureido)methyl) biphenyl-4-yloxy)acetate The 1-(3-fluorophenyl)-1-((4'-hydroxybiphenyl-4-yl) methyl)-3-(3-(trifluoromethyl)phenyl)urea (1.0 equiv) obtained in Example 7 and $K_2CO_3$ (3.0 equiv) were dissolved in an N,N-dimethylformamide (DMF) solution, and cooled on ice. After ethyl chloroacetate (3.0 equiv) was added, a mixed solution was stirred at room temperature under an $N_2$-supplying condition overnight. After the reaction, water was added, and a water-soluble layer was extracted with ethyl acetate (EA). An organic solvent layer was washed with brine, dehydrated with anhydrous magnesium sulfate ($MgSO_4$) and concentrated by evaporation. The concentrate was purified by MPLC, thereby obtaining ethyl-2-(4'-((1-(3-fluorophenyl)-3-(3-(trifluoromethyl)phenyl) ureido)methyl)biphenyl-4-yloxy)acetate (96% yield).

Step 2: Preparation of 2-(4'-((1-(3-fluorophenyl)-3-(3-(trifluoromethyl)phenyl)ureido)methyl)biphenyl-4-yloxy)acetic acid The ethyl-2-(4'-((1-(3-fluorophenyl)-3-(3-(trifluoromethyl)phenyl)ureido)methyl)biphenyl-4-yloxy)acetate (1.0 equiv) obtained in Step 1 was thoroughly mixed with tetrahydrofuran (THF), mixed with a LiOH solution, and stirred for 4 hours. After the reaction, a mixed solution was concentrated, mixed with 2N HCl until becoming an acidic state, and extracted with ethyl acetate (EA). Under a vacuum, an organic solvent layer was removed, thereby obtaining a final product, 2-(4'-((1-(3-fluorophenyl)-3-(3-(trifluoromethyl)phenyl)ureido)methyl)biphenyl-4-yloxy) acetic acid (96% yield).

$^1$H-NMR (CDCl$_3$, 400 MHz) δ 7.61 (1H, s); 7.52-7.47 (5H, m); 7.45-7.35 (2H, m); 7.32-7.26 (3H, m); 7.09-7.15 (1H, m); 7.02-7.00 (1H, d, J=8.4 Hz); 6.98-6.96 (3H, d, J=8.4 Hz); 6.32 (1H, s); 4.96 (2H, s); 4.66 (2H, s); 4.31-4.26 (2H, q); 1.26 (3H, t).

Example 9. Preparation of 4-(4'-((N-(3-fluorophenyl)pentaneamido)methyl)biphenyl-4-yloxy)butanoic acid (AC-1322)

Step 1: Preparation of N-(3-fluorophenyl)-N-((4'-methoxybiphenyl-4-yl)methyl)pentaneamide The 3-fluoro-N-((4'-methoxybiphenyl-4-yl)methyl)aniline obtained in Step 2 of Example 5 was dissolved in dichloromethane (DCM), mixed with triethanolamine (TEA), and cooled on ice. Valeroyl chloride (3.0 equiv) was added to the mixed solution, and stirred at room temperature for 4 hours. After the reaction, RBF was added, and an organic solvent layer was washed with brine and separated. Afterward, the organic solvent layer was collected and dehydrated with anhydrous magnesium sulfate ($MgSO_4$), filtered, and concentrated by evaporation. The concentrate was purified by MPLC, thereby obtaining N-(3-fluorophenyl)-N-((4'-methoxybiphenyl-4-yl)methyl)pentaneamide (100% yield).

Step 2: Preparation of N-(3-fluorophenyl)-N-((4'-hydroxybiphenyl-4-yl)methyl)pentaneamide The N-(3-fluorophenyl)-N-((4'-methoxybiphenyl-4-yl) methyl)pentaneamide (1.0 equiv) obtained in Step 1 was dissolved in a dichloromethane (DCM) solution, and cooled on ice. At 0° C., BBr$_3$ was slowly added, and the mixed solution was stirred at room temperature for 3 hours. The reaction was observed by TLC. After the reaction, ice was added to RBF, and extraction was performed with DCM. An organic solvent layer was separated, dehydrated with anhydrous magnesium sulfate ($MgSO_4$), filtered and then concentrated by evaporation. The concentrate was purified by MPLC, thereby obtaining N-(3-fluorophenyl)-N-((4'-hydroxybiphenyl-4-yl)methyl)pentaneamide (85% yield).

Step 3: Preparation of ethyl 4-(4'-((N-(3-fluorophenyl)pentaneamido)methyl)biphenyl-4-yloxy)butanoate The N-(3-fluorophenyl)-N-((4'-hydroxybiphenyl-4-yl) methyl)pentaneamide (1.0 equiv) obtained in Step 2 and $K_2CO_3$ (3.0 equiv) were dissolved in an N,N-dimethylformamide (DMF) solution, and cooled on ice. After ethyl chloroacetate (3.0 equiv) was added, a mixed solution was stirred at room temperature under an $N_2$-supplying condition overnight. After the reaction, water was added, and a water-soluble layer was extracted with ethyl acetate (EA). An organic solvent layer was washed with brine, dehydrated with anhydrous magnesium sulfate ($MgSO_4$) and concentrated by evaporation. The concentrate was purified by MPLC, thereby obtaining ethyl 4-(4'-((N-(3-fluorophenyl) pentaneamido)methyl)biphenyl-4-yloxy)butanoate (92% yield).

Step 4: Preparation of 4-(4'-((N-(3-fluorophenyl) pentaneamido)methyl)biphenyl-4-yloxy)butanoic acid The ethyl 4-(4'-((N-(3-fluorophenyl)pentaneamido) methyl)biphenyl-4-yloxy)butanoate obtained in Step 3 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, an organic solvent layer was removed, thereby obtaining a final product, 4-(4'-((N-(3-fluorophenyl)pentanamido)methyl)biphenyl-4-yloxy)butanoic acid (100% yield)

$^1$H-NMR (DMSO-d6, 400 MHz) δ 12.2 (1H, br, s); 7.58-7.53 (4H, m); 7.43-7.41 (1H, m); 7.23 (2H, d, J=8.0 Hz); 7.20-7.17 (2H, m); 7.05 (1H, d, J=8.4 Hz); 7.00 (2H, d, J=8.8 Hz); 4.91 (2H, s); 4.02 (2H, t); 2.51 (2H, t); 2.40 (2H, t); 1.98-1.94 (2H, m); 1.52-1.48 (2H, m); 1.24-1.18 (2H, m); 0.79 (3H, t).

Example 10. Preparation of 2-(4'-((N-(3-fluorophenyl)pentaneamido)methyl)biphenyl-4-yloxy)-2-methylpropanoic acid (AC-1321)

Ethyl 4-(4'-((N-(3-fluorophenyl)pentaneamido)methyl) biphenyl-4-yloxy)butanoate was prepared (yield 92%) using ethyl 2-chloro-2-methylpropanoate (3.0 equiv), instead of ethyl 4-chlorobutanoate, in Step 3 of Example 9, and a final product, 2-(4'-((N-(3-fluorophenyl)pentaneamido)methyl) biphenyl-4-yloxy)-2-methylpropanoic acid was obtained by the same method as used in Step 4 of Example 9 (100% yield).

$^1$H-NMR (DMSO-d6, 400 MHz) δ 7.54-7.51 (4H, m); 7.40-7.39 (1H, m); 7.21 (2H, d, J=8.0 Hz); 7.16 (2H, d, J=10.0 Hz); 7.02 (1H, d, J=7.6 Hz); 6.87 (2H, d, J=9.2 Hz);

4.88 (2H, s); 2.49 (2H, t); 1.52 (6H, s); 1.49-1.45 (2H, m); 1.22-1.15 (2H, m); 0.77 (3H, t).

Example 11. Preparation of (E)-3-(4'-((N-(3-fluorophenyl)pentaneamido)methyl)biphenyl-4-yloxy) acrylic acid (AC-1323)

(E)-methyl 3-(4'-((N-(3-fluorophenyl)pentaneamido) methyl)biphenyl-4-yloxy)acrylate was prepared (yield 100%) using methyl (2E)-3-chloroacrylate (3.0 equiv), instead of ethyl 4-chlorobutanoate in Step 3 of Example 9, and a final product, (E)-3-(4'-((N-(3-fluorophenyl)pentaneamido)methyl)biphenyl-4-yloxy)acrylic acid was obtained by the same method as used in Step 4 of Example 9 (29% yield)
$^1$H-NMR (DMSO-d6, 400 MHz) δ 12.1 (1H, s, br); 7.80 (1H, d, J=12.0 Hz); 7.68 (2H, d, J=8.4 Hz); 7.58 (2H, d, J=8.0 Hz); 7.41-7.26 (1H, m); 7.24-7.19 (4H, m); 7.18-7.16 (2H, m); 7.04 (1H, d, J=8.0 Hz); 5.52 (1H, d, J=11.2 Hz); 4.90 (2H, s); 2.49 (2H, t); 1.50-1.44 (2H, m); 1.21-1.14 (2H, m); 0.77 (3H, t).

Example 12. Preparation of 3-(4'-((N-(3-fluorophenyl)pentaneamido)methyl)biphenyl-4-yloxy)propanoic acid (AC-1324)

Methyl 3-(4'-((N-(3-fluorophenyl)pentanamido)methyl) biphenyl-4-yloxy)propanoate was prepared (yield 26.2%) using methyl 3-chloroacetate (3.0 equiv), instead of ethyl 4-chlorobutanoate, in Step 3 of Example 9, and a final product, 3-(4'-((N-(3-fluorophenyl)pentaneamido)methyl) biphenyl-4-yloxy)propanoic acid was obtained (45% yield) by the same method as used in Step 4 of Example 9.
$^1$H-NMR (CDCl$_3$, 400 MHz) δ 7.57-7.51 (4H, m); 7.43-7.38 (1H, m); 7.21 (2H, d, J=8.0 Hz); 7.16 (2H, d, J=10.0 Hz); 7.03 (2H, d, J=8.0 Hz); 6.98 (2H, d, J=8.4 Hz); 4.88 (2H, s); 4.18 (2H, t); 2.68 (2H, t); 2.12 (2H, t); 1.51-1.44 (2H, m); 1.24-1.15 (2H, m); 0.77 (3H, t).

Example 13. Preparation of N-(3-fluorophenyl)-N-((4'-(2-(4-methylpiperazin-1-yl)-2-oxoethoxy)biphenyl-4-yl)methyl)pentaneamide (AC-1309)

Step 1: Preparation of methyl 2-(4'-((N-(3-fluorophenyl)pentaneamido)methyl)biphenyl-4-yloxy) acetate The N-(3-fluorophenyl)-N-((4'-hydroxybiphenyl-4-yl) methyl)pentaneamide obtained in Step 2 of Example 9 and K$_2$CO$_3$ (3.0 equiv) were dissolved in an N,N-dimethylformamide (DMF) solution, and cooled on ice. After methyl bromoacetate (3.0 equiv) was added, a mixed solution was stirred at room temperature under an N$_2$-supplying condition overnight. After the reaction, water was added, and a water-soluble layer was extracted with ethyl acetate (EA). An organic solvent layer was washed with brine, dehydrated with anhydrous magnesium sulfate (MgSO$_4$) and concentrated by evaporation. The concentrate was purified by MPLC, thereby obtaining methyl 2-(4'-((N-(3-fluorophenyl) pentaneamido)methyl)biphenyl-4-yloxy)acetate.

Step 2: Preparation of 2-(4'-((N-(3-fluorophenyl) pentaneamido)methyl)biphenyl-4-yloxy)acetic acid The methyl 2-(4'-((N-(3-fluorophenyl)pentaneamido) methyl)biphenyl-4-yloxy)acetate obtained in Step 1 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, an organic solvent layer was removed, thereby obtaining 2-(4'-((N-(3-fluorophenyl)pentaneamido)methyl)biphenyl-4-yloxy)acetic acid (80% yield).

Step 3: Preparation of N-(3-fluorophenyl)-N-((4'-(2-(4-methylpiperazin-1-yl)-2-oxoethoxy)biphenyl-4-yl)methyl)pentaneamide The 2-(4'-((N-(3-fluorophenyl)pentaneamido)methyl)biphenyl-4-yloxy)acetic acid (1.0 equiv) obtained in Step 2 and K$_2$CO$_3$ (3.0 equiv) were dissolved in an N,N-dimethylformamide (DMF) solution, and cooled on ice. After propargyl bromide (3.0 equiv) was added, a mixed solution was stirred at room temperature under an N$_2$-supplying condition overnight. After the reaction, water was added, and a water-soluble layer was extracted with ethyl acetate (EA). An organic solvent layer was washed with brine, dehydrated with anhydrous magnesium sulfate (MgSO$_4$) and concentrated by evaporation. The concentrate was purified by MPLC, thereby obtaining a final product, N-(3-fluorophenyl)-N-((4'-(2-(4-methylpiperazine-1-yl)-2-oxoethoxy)biphenyl-4-yl)methyl)pentaneamide (65% yield).
$^1$H-NMR (CDCl$_3$, 400 MHz) δ 7.52-7.51 (2H, m); 7.458 (2H, d, J=8.0 Hz); 7.33-7.27 (1H, m); 7.24 (2H, d, J=8.4 Hz); 7.05-6.99 (3H, m); 6.88-6.75 (2H, m); 4.89 (2H, s); 4.68 (2H, s); 3.67-3.60 (4H, m); 2.43-2.38 (4H, m); 2.30 (3H, s); 2.10 (2H, t); 1.64-1.57 (2H, m); 1.30-1.22 (2H, m); 0.83 (3H, t).

Example 14. Preparation of prop-2-ynyl 2-(4'-((N-(3-fluorophenyl)pentaneamido)methyl)biphenyl-4-yloxy)acetate (AC-1390)

The 2-(4'-((N-(3-fluorophenyl)pentaneamido)methyl)biphenyl-4-yloxy)-2-methylpropanoic acid obtained in Example 10 and K$_2$CO$_3$ (3.0 equiv) were dissolved in an N,N-dimethylformamide (DMF) solution, and cooled on ice. After methyl propiolate (3.0 equiv) was added, a mixed solution was stirred at room temperature under an N$_2$-supplying condition overnight. After the reaction, water was added, and a water-soluble layer was extracted with ethyl acetate (EA). An organic solvent layer was washed with brine, dehydrated with anhydrous magnesium sulfate (MgSO$_4$) and concentrated by evaporation. The concentrate was purified by MPLC, thereby obtaining a final product, prop-2-ynyl 2-(4'-((N-(3-fluorophenyl)pentanamido) methyl)biphenyl-4-yloxy)acetate (61.3% yield).
$^1$H-NMR (CDCl$_3$, 400 MHz) δ 7.51 (2H, d, J=8.4 Hz); 7.45 (2H, d, J=8.0 Hz); 7.33-7.28 (1H, m); 7.21 (2H, d, J=8.0 Hz); 7.05-7.01 (1H, m); 6.97 (2H, d, J=8.4 Hz); 6.82-6.75 (2H, m); 4.89 (2H, s); 4.83 (2H, d, J=1.6 Hz); 4.72 (2H, s); 2.53 (1H, s); 2.09 (2H, t); 1.64-1.58 (2H, m); 1.27-1.20 (2H, m); 0.831 (3H, t).

Example 15. Preparation of N-(3-fluorophenyl)-N-((4'-(prop-2-ynyloxy)biphenyl-4-yl)methyl)pentaneamide (AC-1389)

The N-(3-fluorophenyl)-N-((4'-hydroxybiphenyl-4-yl) methyl)pentanamide obtained in Step 2 of Example 9 and K$_2$CO$_3$ (3.0 equiv) were dissolved in an N,N-dimethylformamide (DMF) solution, and cooled on ice. After methyl propiolate (3.0 equiv) was added, the mixed solution was stirred at room temperature under an N$_2$-supplying condition overnight. After the reaction, water was added, and a water-soluble layer was extracted with ethyl acetate (EA). An organic solvent layer was washed with brine, dehydrated with anhydrous magnesium sulfate (MgSO$_4$) and concentrated by evaporation. The concentrate was purified by MPLC, thereby obtaining a final product, N-(3-fluorophenyl)-N-((4'-(prop-2-ynyloxy)biphenyl-4-yl)methyl)pentaneamide (58.2% yield).

$^1$H-NMR (CDCl$_3$, 400 MHz) δ 7.54-7.50 (2H, m); 7.46 (2H, d, J=8.4 Hz); 7.33-7.28 (1H, m); 7.23 (2H, d, J=8.4 Hz); 7.06-7.03 (3H, m); 6.82-6.75 (2H, m); 4.89 (2H, s); 4.73 (2H, d, J=2.0 Hz); 2.54 (1H, t); 2.09 (2H, t); 1.64-1.57 (2H, m); 1.29-1.20 (2H, m); 0.83 (3H, m).

Example 16. Preparation of 4'-((N-(2-fluorophenyl)pentaneamido)methyl)biphenyl-4-carboxylic acid (AC-1071)

Step 1: Preparation of methyl 4'-((2-fluorophenylamino)methyl)biphenyl-2-carboxylate Methyl 4'-formylbiphenyl-4-carboxylate (1.0 equiv) and 2-fluoroaniline (3.0 equiv) were dissolved in methanol, and stirred at room temperature for 4 hours. The reaction performed until an imine was formed was observed by TLC, and after the imine was formed, a methanol solution in which 1M NaCNBH$_3$ (1.0 equiv) and 0.5M ZnCl$_2$ (1.0 equiv) were mixed was added to the solution, followed by stirring at room temperature overnight. After the reaction, under a vacuum, methanol was removed, the remaining solution was diluted with ethyl acetate (EA), and an organic solvent layer was washed with brine, dehydrated with anhydrous magnesium sulfate (MgSO$_4$) and concentrated by evaporation. The concentrate was purified by MPLC, thereby obtaining methyl 4'-((2-fluorophenylamino)methyl)biphenyl-4-carboxylate (95% yield).

Step 2: Preparation of methyl 4'-((N-(2-fluorophenyl)pentaneamido)methyl)biphenyl-4-carboxylate The methyl 4'-((2-fluorophenylamino)methyl)biphenyl-4-carboxylate obtained in Step 1 was dissolved in dichloromethane (DCM), mixed with triethanolamine (TEA), and cooled on ice. Valeroyl chloride (3.0 equiv) was added to the mixed solution, and stirred at room temperature for 4 hours. After the reaction, RBF was added, and an organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining methyl 4'-((N-(2-fluorophenyl)pentaneamido)methyl)biphenyl-4-carboxylate (95% yield).

Step 3: Preparation of 4'-((N-(2-fluorophenyl)pentaneamido)methyl)biphenyl-4-carboxylic acid The 4'-((N-(2-fluorophenyl)pentaneamido)methyl)biphenyl-4-carboxylate (1.0 equiv) obtained in Step 2 was thoroughly mixed with tetrahydrofuran (THF), mixed with an LiOH solution, and stirred for 4 hours. After the reaction, the mixed solution was concentrated, mixed with 2N HCl until the mixed solution became an acidic state, and extracted with ethyl acetate (EA). Under a vacuum, the organic solvent layer was removed, thereby obtaining a final product, 4'-((N-(2-fluorophenyl)pentaneamido)methyl)biphenyl-4-carboxylic acid (94% yield).

$^1$H-NMR (CDCl$_3$, 400 MHz) δ 8.16 (2H, d, J=8.4 Hz); 7.67 (2H, d, J=8.4 Hz); 7.54 (2H, d, J=7.6 Hz); 7.31 (2H, d, J=8.4 Hz); 7.18-7.08 (3H, m); 7.00-6.96 (1H, t); 5.28 (1H, d, J=14.4 Hz); 4.56 (1H, d, J=14.4 Hz); 2.09 (2H, t); 1.63-1.59 (2H, m); 1.27-1.22 (2H, m); 0.83 (3H, t).

Example 17. Preparation of 4'-((N-(4-fluorophenyl)pentaneamido)methyl)biphenyl-4-carboxylic acid (AC-1072)

The 4'-((4-fluorophenylamino)methyl)biphenyl-4-carboxylate was prepared by the same method as used in Step 1 of Example 16 using 4-fluoroaniline instead of 2-fluoroaniline, and methyl 4'-((N-(1-fluorophenyl)pentaneamido)methyl)biphenyl-4-carboxylate was prepared, thereby obtaining a final product, 4'-((N-(4-fluorophenyl)pentanamido)methyl)biphenyl-4-carboxylic acid (90% yield)

$^1$H-NMR (CDCl$_3$, 400 MHz) δ 8.17 (2H, d, J=8.4 Hz); 7.68 (2H, d, J=8 Hz); 7.56 (2H, d, J=8.0 Hz); 7.30 (2H, d, J=7.6 Hz); 7.04-6.98 (4H, m); 4.91 (2H, s); 2.07 (2H, t); 1.62-1.58 (2H, m); 1.25-1.23 (2H, m); 0.83 (3H, t).

Example 18. Preparation of 4'-((N-(2-methoxyphenyl)pentaneamido)methyl)biphenyl-3-carboxylic acid (AC-1076)

4'-((2-methoxyphenylamino)methyl)biphenyl-3-carboxylate was prepared by the same method as used in Step 1 of Example 16 using methyl 4'-formylbiphenyl-3-carboxylate instead of methyl 4'-formylbiphenyl-4-carboxylate and 2-methoxyaniline instead of 2-fluoroaniline, and methyl 4'-((N-(2-methoxyphenyl)pentanamido)methyl)biphenyl-3-carboxylate was prepared by the same method as used in Steps 2 and 3 of Example 16, thereby obtaining a final product, 4'-((N-(2-methoxyphenyl)pentaneamido)methyl)biphenyl-3-carboxylic acid (90% yield).

$^1$H-NMR (400 MHz, CDCl$_3$) δ 8.13 (1H, s); 7.90-7.86 (2H, m); 7.62-7.54 (3H, m); 7.26 (2H, d, J=7.6 Hz); 7.06 (2H, d, J=8.8 Hz); 6.89 (2H, d, J=8.8 Hz); 4.83 (2H, s); 3.70 (3H, s); 2.05-2.01 (2H, m); 1.46-1.41 (2H, m); 0.75 (3H, t).

Example 19. Preparation of 4'-((N-(3-methoxyphenyl)pentaneamido)methyl)biphenyl-3-carboxylic acid (AC-1077)

4'-((3-methoxyphenylamino)methyl)biphenyl-3-carboxylate was prepared by the same method as used in Step 1 of Example 16 using methyl 4'-formylbiphenyl-3-carboxylate instead of methyl 4'-formylbiphenyl-4-carboxylate and 3-methoxyaniline instead of 2-fluoroaniline, and methyl 4'-((N-(3-methoxyphenyl)pentaneamido)methyl)biphenyl-3-carboxylate was prepared by the same method as used in Steps 2 and 3 of Example 16, thereby obtaining a final product, 4'-((N-(3-methoxyphenyl)pentaneamido)methyl)biphenyl-3-carboxylic acid (92% yield).

$^1$H-NMR (400 MHz, CDCl$_3$) δ 8.24 (1H, s); 7.89 (1H, d, J=7.2 Hz); 7.84 (1H, d, J=7.2 Hz); 7.59-7.52 (3H, m); 7.29 (2H, d, J=7.6 Hz); 7.00-6.60 (4H, m); 4.89 (2H, s); 3.78 (3H. s); 2.13 (2H, t); 1.62-1.52 (2H, m); 1.19-1.16 (2H, m); 0.83 (3H, t).

Example 20. Preparation of 4'-((N-(4-methoxyphenyl)pentaneamido)methyl)biphenyl-3-carboxylic acid (AC-1078)

4'-((4-methoxyphenylamino)methyl)biphenyl-3-carboxylate was prepared by the same method as used in Step 1 of Example 16 using methyl 4'-formylbiphenyl-3-carboxylate instead of methyl 4'-formylbiphenyl-4-carboxylate and 4-methoxyaniline instead of 2-fluoroaniline, and methyl 4'-((N-(4-methoxyphenyl)pentaneamido)methyl)biphenyl-3-carboxylate was prepared by the same method as used in Steps 2 and 3 of Example 16, thereby obtaining a final product, 4'-((N-(4-methoxyphenyl)pentaneamido)methyl) biphenyl-3-carboxylic acid (92% yield).

$^1$H-NMR (400 MHz, CDCl$_3$) δ 8.32 (1H, s); 8.07 (1H, d, J=7.6 Hz); 7.82 (1H, d, J=8.0 Hz); 7.55-7.53 (3H, m); 7.30 (2H, d, J=7.6 Hz) 6.92-6.83 (4H, m); 4.90 (2H, s); 3.81 (3H, s); 2.09 (2H, t); 1.59-1.56 (2H, m); 1.25-1.20 (2H, m); 0.83 (3H, t).

Example 21. Preparation of (N-((2'-(4-methylpiperazine-1-carbonyl)biphenyl-4-yl)methyl)-N-phenyl-pentaneamide) (AC-888)

4'-((N-phenylpentanamido)methyl)biphenyl-2-carboxylic acid (1.0 equiv), 1-methyl piperazine (0.9 equiv), HATU (1.2 equiv) and N,N-diisopropylethylamine (DIPEA) (2.5 equiv) were dissolved in N,N-dimethylformamide (DMF), and the mixed solution was stirred at room temperature overnight. After the reaction, water was added, and a water-soluble layer was extracted with ethyl acetate (EA). An organic solvent layer was filtered and then concentrated by evaporation. The concentrate was purified by column chromatography, thereby obtaining a final product, (N-((2'-(4-methylpiperazine-1-carbonyl)biphenyl-4-yl)methyl)-N-phenylpentaneamide) (93% yield).

$^1$H-NMR (DMSO-d$_6$, 500 MHz) δ 7.71 (m, 1H), 7.61 (m, 3H), 7.51 (m, 1H), 7.39 (m, 2H), 7.34 (m, 2H), 7.27 (m, 2H), 7.19 (m, 2H), 4.90 (s, 2H), 3.6 (d, 4H), 2.36 (d, 4H), 2.19 (s, 3H), 2.07 (m, 2H), 1.48 (m, 2H), 1.18 (m, 2H), 0.76 (t, 3H).

Example 22. Preparation of N-((3'-(4-methylpiperazine-1-carbonyl)biphenyl-4-yl)methyl)-N-phenyl-pentaneamide (AC-889)

Step 1: Preparation of methyl 4'-formylbiphenyl-3-carboxylate

Methyl 3-bromobenzoate (1.0 equiv) and 4-formylphenylboronic acid (1.1 equiv) were thoroughly mixed with RBF, and dissolved in a 1,4-dioxane:H$_2$O (5:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing was further performed for 15 minutes, the mixed solution was heated and refluxed for 4 hours. The mixture obtained by the reaction was filtered with ethyl acetate (EA), extracted, dehydrated with anhydrous MgSO$_4$, concentrated by evaporation, and purified by column chromatography, thereby obtaining methyl 4'-formylbiphenyl-3-carboxylate (90% yield).

Step 2: Preparation of methyl 4'-((phenylamino)methyl)biphenyl-3-carboxylate The methyl 4'-formylbiphenyl-3-carboxylate (1.0 equiv) obtained in Step 1 and aniline (3.0 equiv) were dissolved in methanol, and stirred at room temperature for 4 hours. A reaction performed until an imine was formed was observed by TLC, and after the imine was formed, a methanol solution in which 1M NaCNBH$_3$ (1.0 equiv) and 0.5M ZnCl$_2$ (1.0 equiv) were mixed was added to the solution, followed by stirring at room temperature overnight. After the reaction, the methanol was removed under a vacuum, a remaining solution was diluted with ethyl acetate (EA), and an organic solvent layer was washed with brine, dehydrated with anhydrous magnesium sulfate (MgSO$_4$) and concentrated by evaporation. The concentrate was purified by column chromatography, thereby obtaining methyl 4'-((phenylamino)methyl)biphenyl-3-carboxylate (86% yield).

Step 3: Preparation of methyl 4'-((N-phenylpentaneamido)methyl)biphenyl-3-carboxylate The 4'-((phenylamino)methyl)biphenyl-3-carboxylate obtained in Step 2 was dissolved in dichloromethane (DCM), mixed with triethanolamine (TEA), and cooled on ice. Valeroyl chloride (2.0 equiv) was added to the mixed solution, and then stirred at room temperature for 4 hours. After the reaction, RBF was added, and an organic solvent layer was washed with brine and separated. Afterward, the organic solvent layer was collected, dehydrated with anhydrous magnesium sulfate (MgSO$_4$), filtered, and concentrated by evaporation. The concentrate was purified by column chromatography, thereby obtaining methyl 4'-((N-phenylpentaneamido)methyl)biphenyl-3-carboxylate (92% yield).

Step 4: Preparation of 4'-((N-phenylpentaneamido)methyl)biphenyl-3-carboxylic acid The methyl 4'-((N-phenylpentaneamido)methyl)biphenyl-3-carboxylate (1.0 equiv) obtained in Step 3 was thoroughly mixed with tetrahydrofuran (THF), mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, purified by column chromatography, thereby obtaining 4'-((N-phenylpentaneamido)methyl)biphenyl-3-carboxylic acid (94% yield).

Step 5: Preparation of N-((3'-(4-methylpiperazine-1-carbonyl)biphenyl-4-yl)methyl)-N-phenylpentaneamide The 4'-((N-phenylpentanamido)methyl)biphenyl-3-carboxylic acid (1.0 equiv) obtained in Step 4, 1-methyl piperazine (0.9 equiv), HATU (1.2 equiv) and N,N-diisopropylethylamine (DIPEA) (2.5 equiv) were dissolved in N,N-dimethylformamide (DMF), and the mixed solution was stirred at room temperature overnight. After the reaction, water was added, and a water-soluble layer was extracted with ethyl acetate (EA). An organic solvent layer was filtered and then concentrated by evaporation. The concentrate was purified by column chromatography, thereby obtaining a final product, N-((3'-(4-methylpiperazine-1-carbonyl)biphenyl-4-yl)methyl)-N-phenylpentaneamide (93% yield).

$^1$H-NMR (DMSO-d$_6$, 500 MHz) δ 7.71 (m, 1H), 7.61 (m, 3H), 7.51 (m, 1H), 7.42 (m, 2H), 7.30 (m, 2H), 7.25 (m, 2H), 7.19 (m, 2H), 4.90 (s, 2H), 3.16 (d, 4H), 2.38 (d, 4H), 2.18 (s, 3H), 2.07 (m, 2H) 1.48 (m, 2H), 1.18 (m, 2H), 0.76 (t, 3H).

Example 23. Preparation of 4'-((N-(3-fluorophenyl) pentaneamido)methyl)biphenyl-2-carboxylic acid (AC-891)

Step 1: Preparation of methyl 4'-formylbiphenyl-2-carboxylate

Methyl 3-bromobenzoate (1.0 equiv) and 4-formylphenylboronic acid (1.1 equiv) were thoroughly mixed with RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing again for 15 minutes, the resulting solution was heated and refluxed for 4 hours. After the reaction, the mixture was filtered with ethyl acetate (EA), extracted, dehydrated with anhydrous MgSO$_4$, concentrated by evaporation, and purified by column chromatography, thereby obtaining methyl 4'-formylbiphenyl-2-carboxylate (90% yield).

Step 2: Preparation of 4'-((3-fluorophenylamino) methyl)biphenyl-2-carboxylate

The methyl 4'-formylbiphenyl-2-carboxylate (1.0 equiv) obtained in Step 1 and 3-fluoroaniline (3-fluroaniline) (3.0 equiv) were dissolved in methanol, stirred at room temperature for 4 hours. The reaction performed until an imine was formed was observed by TLC, and after the imine was formed, a methanol solution in which 1M NaCNBH$_3$ (1.0 equiv) and 0.5M ZnCl$_2$ (1.0 equiv) were mixed was added to the solution and stirred at room temperature overnight. After the reaction, the methanol was removed under a vacuum, a remaining solution was diluted with ethyl acetate (EA), and the organic solvent layer was washed with brine, dehydrated with anhydrous magnesium sulfate (MgSO$_4$) and concentrated by evaporation. The concentrate was purified by column chromatography, thereby obtaining 4'-((3-fluorophenylamino)methyl)biphenyl-2-carboxylate (86% yield).

Step 3: Preparation of Methyl 4'-((N-(3-fluorophenyl)pentaneamido)methyl)biphenyl-2-carboxylate The 4'-((3-fluorophenylamino) methyl) biphenyl-2-carboxylate obtained in Step 2 was dissolved in dichloromethane (DCM), mixed with triethanolamine (TEA), and cooled on ice. Valeroyl chloride (2.0 equiv) was added to the mixed solution, and stirred at room temperature for 4 hours. After the reaction, RBF was added, and an organic solvent layer was washed with brine and separated. Afterward, the organic solvent layer was collected, dehydrated with anhydrous magnesium sulfate (MgSO$_4$), filtered, and concentrated by evaporation. The concentrate was purified by column chromatography, thereby obtaining methyl 4'-((N-(3-fluorophenyl)pentaneamido)methyl)biphenyl-2-carboxylate (92% yield).

Step 4: Preparation of 4'-((N-(3-fluorophenyl)pentaneamido)methyl)biphenyl-2-carboxylic acid The methyl 4'-((N-(3-fluorophenyl) pentaneamido) methyl) biphenyl-2-carboxylate (1.0 equiv) obtained in Step 3 was thoroughly mixed with tetrahydrofuran (THF), mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed and purified by column chromatography, thereby obtaining 4'-((N-(3-fluorophenyl)pentaneamido)methyl)biphenyl-2-carboxylic acid (94% yield).

$^1$H-NMR (DMSO-d6, 500 MHz) δ 12.8 (s, br, 1H), 7.7 (m, 1H), 7.55 (m, 1H), 7.45 (m, 2H), 7.35 (m, 2H), 7.25 (m, 2H), 7.20 (m, 3H), 7.05 (m, 1H), 4.93 (s, 2H), 2.14 (m, 2H), 1.49 (m, 2H), 1.20 (m, 2H), 0.78 (t, 3H).

Example 24. Preparation of 4'-((N-(3-fluorophenyl) pentaneamido)methyl)biphenyl-4-carboxylic acid (AC-893)

Step 1: Preparation of methyl 4'-formylbiphenyl-4-carboxylate

Methyl 4-bromobenzoate (1.0 equiv) and 4-formylphenylboronic acid (1.1 equiv) were thoroughly mixed with RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing again for 15 minutes, the resulting solution was heated and refluxed for 4 hours. After the reaction, the mixture was filtered with ethyl acetate (EA), extracted, dehydrated with anhydrous MgSO$_4$, concentrated by evaporation, and purified by column chromatography, thereby obtaining methyl 4'-formylbiphenyl-4-carboxylate (90% yield).

Step 2: Preparation of methyl 4'-((3-fluoroamino) methyl) biphenyl-4-carboxylate The methyl 4'-formylbiphenyl-4-carboxylate (1.0 equiv) obtained in Step 1 and 3-fluoroaniline (3.0 equiv) were dissolved in methanol, and stirred at room temperature for 4 hours. The reaction performed until an imine was formed was observed by TLC, and after the imine was formed, a methanol solution in which 1M NaCNBH$_3$ (1.0 equiv) and 0.5M ZnCl$_2$ (1.0 equiv) were mixed was added to the solution and stirred at room temperature overnight. After the reaction, the methanol was removed under a vacuum, the remaining solution was diluted with ethyl acetate (EA), and an organic solvent layer was washed with brine, dehydrated with anhydrous magnesium sulfate (MgSO$_4$) and concentrated by evaporation. The concentrate was purified by column chromatography, thereby obtaining methyl 4'-((3-fluoroamino) methyl) biphenyl-4-carboxylate (86% yield).

Step 3: Preparation of methyl 4'-((N-(3-fluorophenyl) pentaneamido) methyl) biphenyl-4-carboxylate The methyl 4'-((3-fluoroamino) methyl) biphenyl-4-carboxylate obtained in Step 2 was dissolved in dichloromethane (DCM), mixed with triethanolamine (TEA), and cooled on ice. Valeroyl chloride (2.0 equiv) was added to the mixed solution, stirred at room temperature for 4 hours. After the reaction, RBF was added, and an organic solvent layer was washed with brine and separated. Afterward, the organic solvent layer was collected, dehydrated with anhydrous magnesium sulfate (MgSO$_4$), filtered, and concentrated by evaporation. The concentrate was purified by column chromatography, thereby obtaining methyl 4'-((N-(3-fluorophenyl) pentaneamido) methyl) biphenyl-4-carboxylate (92% yield).

Step 4: Preparation of 4'-((N-(3-fluorophenyl)pentaneamido)methyl)biphenyl-4-carboxylic acid The methyl 4'-((N-(3-fluorophenyl) pentaneamido) methyl) biphenyl-4-carboxylate (1.0 equiv) obtained in Step 3 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, purified by column chromatography, thereby obtaining 4'-((N-(3-fluorophenyl)pentaneamido)methyl)biphenyl-4-carboxylic acid (94% yield).

$^1$H-NMR (DMSO-d6, 500 MHz) δ 13.1 (s, br, 1H), 8.12 (d, 1H), 7.85 (d, 2H), 7.66 (d, 2H), 7.56 (m, 2H), 7.20 (m, 2H), 7.20 (m, 2H) 7.05 (m, 1H), 4.91 (s, 2H), 2.08 (m, 2H), 1.48 (m, 2H), 1.18 (m, 2H), 0.76 (t, 3H).

Example 25. Preparation of N-(3-fluorophenyl)-N-((4'-(morpholine-4-carbonyl)-[1,1'-biphenyl]-4-yl)methyl)pentaneamide (AC-950)

The 4'-((N-(3-fluorophenyl)pentaneamido)methyl)biphenyl-4-carboxylic acid (1.0 equiv) obtained in Example 24, morpholine (0.9 equiv), HATU (1.2 equiv) and N,N-diisopropylethylamine (DIPEA) (2.5 equiv) were dissolved in N,N-dimethylformamide (DMF), and the mixed solution was stirred at room temperature overnight. After the reaction, water was added, and a water-soluble layer was extracted with ethyl acetate (EA). The organic solvent layer was filtered and then concentrated by evaporation. The concentrate was purified by column chromatography, thereby obtaining a final product, N-(3-fluorophenyl)-N-((4'-(morpholine-4-carbonyl)-[1,1'-biphenyl]-4-yl)methyl)pentaneamide (93% yield).

$^1$H-NMR (DMSO-d6, 500 MHz) δ 7.95 (m, 1H), 7.70 (d, 2H), 7.62 (d, 2H), 7.44 (d, 2H), 7.36 m, 2H), 7.27 (m, 2H), 7.19 (d, 2H), 4.90 (s, 2H), 3.01 (d, 4H), 2.5 (s, 3H), 2.36 (d, 4H), 2.07 (m, 2H), 1.48 (m, 2H), 1.18 (m, 2H), 0.76 (t, 3H).

Example 26. Preparation of N-(3-fluorophenyl)-N-((4'-(4-methylpiperazine-1-carbonyl)biphenyl-4-yl)methyl)pentaneamide (AC-951)

Step 1: Preparation of 4'-((N-(3-fluorophenyl)pentaneamido)methyl)biphenyl-4-carboxylic acid Methyl 4'-((3-methoxyphenylamino)methyl)biphenyl-4-carboxylate was prepared by the same method as used in Step 1 of Example 16 using 3-methoxyaniline instead of 2-fluoroaniline, and methyl 4'-((N-(3-methoxyphenyl)pentanamido)methyl)biphenyl-4-carboxylate was prepared by the same method as used in Steps 2 and 3 of Example 16, thereby obtaining 4'-((N-(3-methoxyphenyl)pentaneamido)methyl)biphenyl-4-carboxylic acid (94% yield).

Step 2: Preparation of N-(3-fluorophenyl)-N-((4'-(4-methylpiperazine-1-carbonyl)biphenyl-4-yl)methyl)pentaneamide The 4'-((N-(3-methoxyphenyl)pentaneamido)methyl)biphenyl-4-carboxylic acid (1.0 equiv) obtained in Step 1, 1-methyl piperazine (0.9 equiv), EDC (1.2 equiv), HoBt (1.2 equiv) and N,N-diisopropylethylamine (DIPEA) (2.5 equiv) were dissolved in N,N-dimethylformamide (DMF), and the mixed solution was stirred at room temperature overnight. After the reaction, water was added, and a water-soluble layer was extracted with ethyl acetate (EA). An organic solvent layer was filtered and then concentrated by evaporation. The concentrate was purified by column chromatography, thereby obtaining a final product, N-(3-fluorophenyl)-N-((4'-(4-methylpiperazine-1-carbonyl)biphenyl-4-yl)methyl)pentaneamide (93% yield).

$^1$H-NMR (DMSO-d$_6$, 500 MHz) δ 7.95 (1H, m), 7.70 (2H, d), 7.62 (2H, d), 7.44 (2H, d), 7.36 (2H, m), 7.27 (2H, m), 7.19 (2H, d), 4.90 (2H, s), 3.01 (4H, d), 2.5 (3H, s), 2.36 (4H, d), 2.07 (2H, m), 1.48 (2H, m), 1.18 (2H, m), 0.76 (3H, t).

Example 27. Preparation of N-((2'-(1H-tetrazol-5-yl)biphenyl-4-yl)methyl)-N-phenylpentaneamide (AC-952)

Step 1: Preparation of 4'-((phenylamino)methyl)biphenyl-2-carbonitrile

Aniline (1.0 equiv) and K$_2$CO$_3$ (3.0 equiv) were dissolved in a dichloromethane (DCM) solution, and cooled on ice. Afterward, 4'-(bromomethyl)-2-biphenylcarbonitrile (3.0 equiv) was added, and the mixed solution was stirred at room temperature under an N$_2$-supplying condition overnight. After the reaction, the mixture was filtered through ethyl acetate (EA) and extracted, and an organic solvent layer was filtered and concentrated by evaporation. The concentrate was purified by MPLC, thereby obtaining 4'-((phenylamino)methyl)biphenyl-2-carbonitrile (86% yield).

Step 2: Preparation of N-((2'-cyanobiphenyl-4-yl)methyl)-N-phenylpentaneamide

The 4'-((phenylamino)methyl)biphenyl-2-carbonitrile obtained in Step 1 was dissolved in dichloromethane (DCM), mixed with triethanolamine (TEA), and cooled on ice. Valeroyl chloride (3.0 equiv) was added to the mixed solution, and stirred at room temperature for 4 hours. After the reaction, RBF was added, and an organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining N-((2'-cyanobiphenyl-4-yl)methyl)-N-phenylpentaneamide (92%).

Step 3: Preparation of N-((2'-(1H-tetrazol-5-yl)biphenyl-4-yl)methyl)-N-phenylpentaneamide The N-((2'-cyanophenyl-4-yl)methyl)-N-phenylpentaneamide (1.0 equiv) obtained in Step 2, tributyltin chloride (2.0 equiv) and sodium azide (2.0 equiv) were thoroughly mixed with RBF, and dissolved in O-xylene (10 V). The mixed solution was refluxed for 12 hours, and concentrated by evaporating a solvent. The concentrate was purified by MPLC, thereby obtaining a final product, N-((2'-(1H-tetrazol-5-yl)biphenyl-4-yl)methyl)-N-phenylpentaneamide (92% yield).

$^1$H-NMR (MeOD, 500 MHz) δ 8.16 (1H, d, J=6.0 Hz); 7.60-7.52 (2H, m); 7.43-7.39 (3H, m); 7.34 (1H, t); 7.25 (2H, t); 7.15 (2H, d, J=6.4 Hz); 7.03 (2H, d, J=6.0 Hz); 4.90 (2H, s); 2.09 (2H, t); 1.57-1.50 (2H, m); 1.22-1.18 (2H, m); 0.79 (3H, t).

Example 28. Preparation of N-((4'-methoxybiphenyl-4-yl)methyl)-N-phenylpentaneamide (AC-1067)

Step 1: Preparation of 4'-methoxybiphenyl-4-carbaldehyde

4-Bromoanisole (1.0 equiv) and 4-formylphenylboronic acid (1.1 equiv) were thoroughly mixed in RBF, and dissolved in a 1,4-dioxane:H$_2$O (10:1) mixed solution. Degassing was performed for 20 minutes by adding Pd(dppf)Cl$_2$.DCM (0.01 equiv) to the mixed solution, and performed again for 20 minutes by adding Na₂CO₃. After degassing again for 15 minutes, the resulting solution was refluxed for 3 hours. After the reaction, the mixture was filtered with ethyl acetate (EA), extracted, dehydrated with anhydrous MgSO₄, concentrated by evaporation, and purified by MPLC, thereby obtaining 4'-methoxybiphenyl-4-carbaldehyde (73% yield).

Step 2: Preparation of N-((4'-methoxybiphenyl-4-yl)methyl)aniline

The 4'-methoxybiphenyl-4-carbaldehyde (1.0 equiv) obtained in Step 1 and aniline (3.0 equiv) were dissolved in methanol, and stirred at room temperature for 4 hours. The reaction performed until an imine was formed was observed by TLC, and after the imine was formed, a methanol solution in which 1M NaCNBH₃ (1.0 equiv) and 0.5M ZnCl₂ (1.0 equiv) were mixed was added to the solution and stirred at room temperature overnight. After the reaction, the methanol was removed under a vacuum, a remaining solution was diluted with ethyl acetate (EA), and an organic solvent layer was washed with brine, dehydrated with anhydrous magnesium sulfate (MgSO₄) and concentrated by evaporation. The concentrate was purified by MPLC, thereby obtaining N-((4'-methoxybiphenyl-4-yl)methyl)aniline.

Step 3: Preparation of N-((4'-methoxybiphenyl-4-yl)methyl)-N-phenylpentaneamide

The N-((4'-methoxybiphenyl-4-yl)methyl)aniline obtained in Step 2 was dissolved in dichloromethane (DCM), mixed with triethanolamine (TEA), and cooled on ice. Valeroyl chloride (3.0 equiv) was added to the mixed solution, and stirred at room temperature for 4 hours. After the reaction, RBF was added, and an organic solvent layer was washed with brine and separated. Afterward, the organic solvent layer was collected, dehydrated with anhydrous magnesium sulfate (MgSO₄), filtered, and concentrated by evaporation. The concentrate was purified by MPLC, thereby obtaining a final product, N-((4'-methoxybiphenyl-4-yl)methyl)-N-phenylpentaneamide (100% yield).

¹H NMR (400 MHz, CDCl₃) δ 7.51 (2H, d, J=8.4 Hz); 7.45 (2H, d, J=8.0 Hz); 7.34-7.30 (3H, m); 7.24 (2H, d, J=8.0 Hz); 7.01 (2H, d, J=7.2 Hz); 6.96 (2H, d, J=8.8 Hz); 4.90 (2H, s); 3.85 (3H, s); 2.08 (2H, t); 1.63-1.57 (2H, m); 1.26-1.20 (2H, m); 0.83 (3H, t).

Example 29. Preparation of N-((4'-hydroxybiphenyl-4-yl)methyl)-N-phenylpentaneamide (AC-1069)

The N-((4'-methoxybiphenyl-4-yl)methyl)-N-phenylpentaneamide (1.0 equiv) obtained in Example 28 was dissolved in a dichloromethane (DCM) solution, and cooled on ice. At 0° C., BBr₃ was slowly added, and the mixed solution was stirred at room temperature for 3 hours. The reaction was observed by thin layer chromatography (TLC). After the reaction, ice was added to RBF, and extraction was performed with DCM. An organic solvent layer was separated, dehydrated with anhydrous magnesium sulfate (MgSO₄), filtered and then concentrated by evaporation. The concentrate was purified by MPLC, thereby obtaining a final product, N-((4'-hydroxybiphenyl-4-yl)methyl)-N-phenylpentaneamide (80% yield).

¹H-NMR (CDCl₃, 400 MHz) δ 7.44-7.37 (4H, m); 7.35-7.31 (3H, m); 7.26 (2H, d, J=8.4 Hz); 7.03 (2H, d, J=6.8 Hz); 6.88 (2H, d, J=8.4 Hz); 5.37 (1H, br, s); 4.91 (2H, s); 2.10 (2H, t); 1.63-1.57 (2H, m); 1.25-1.20 (2H, m); 0.83 (3H, t).

Example 30. Preparation of 2-(4'-((N-phenylpentaneamido)methyl)biphenyl-4-yloxy)acetic acid (AC-1073)

Step 1: Preparation of ethyl (2-(4'-((N-phenylpentaneamido)methyl)biphenyl-4-yloxy)acetate The N-((4'-hydroxybiphenyl-4-yl)methyl)-N-phenylpentaneamide (1.0 equiv) obtained in Example 29 and K₂CO₃ (3.0 equiv) were dissolved in an N,N-dimethylformamide (DMF) solution, and cooled on ice. After adding ethyl bromoacetate (3.0 equiv), the mixed solution was stirred at room temperature under an N₂-supplying condition overnight. After the reaction, water was added, and a water-soluble layer was extracted with ethyl acetate (EA). An organic solvent layer was washed with brine, dehydrated with anhydrous magnesium sulfate (MgSO₄) and concentrated by evaporation. The concentrate was purified by MPLC, thereby obtaining ethyl (2-(4'-((N-phenylpentaneamido)methyl)biphenyl-4-yloxy)acetate.

Step 2: Preparation of 2-(4'-((N-phenylpentaneamido)methyl)biphenyl-4-yloxy)acetic acid The ethyl (2-(4'-((N-phenylpentaneamido)methyl)biphenyl-4-yloxy)acetate (1.0 equiv) obtained in Step 1 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, thereby obtaining a final product, 2-(4'-((N-phenylpentaneamido)methyl)biphenyl-4-yloxy)acetic acid (85% yield).

¹H-NMR (CDCl₃, 400 MHz) δ 7.49 (2H, d, J=8.0 Hz); 7.41 (2H, d, J=8.0 Hz); 7.34-7.32 (3H, m); 7.22 (2H, d, J=8.0 Hz); 7.01-6.95 (4H, m); 4.91 (2H, s); 4.97 (2H, s); 2.10 (2H, t); 1.65-1.55 (2H, m); 1.26-1.17 (2H, m); 0.80 (3H, t).

Example 31. Preparation of N-(3-fluorophenyl)-N-((4'-methoxybiphenyl-4-yl)methyl)pentaneamide (AC-1068)

3-Fluoro-N-((4'-methoxybiphenyl-4-yl)methyl)aniline was prepared using 3-fluoroaniline instead of aniline, and a final product, N-(3-fluorophenyl)-N-((4'-methoxybiphenyl-4-yl)methyl)pentaneamide was obtained (100% yield).

¹H NMR (400 MHz, CDCl₃) δ 7.52-7.45 (4H, m); 7.31-7.30 (1H, m); 7.23 (2H, d, J=8.4 Hz); 7.03-7.03 (1H, m); 6.97 (2H, d, J=8.8 Hz); 6.82-6.80 (2H, m); 4.89 (2H, s); 3.85 (3H, s); 2.10 (2H, t); 1.62-1.57 (2H, m); 1.27-1.22 (2H, m); 0.83 (3H, t).

Example 32. Preparation of N-(3-fluorophenyl)-N-((4'-hydroxybiphenyl-4-yl)methyl)pentaneamide (AC-1070)

The N-(3-fluorophenyl)-N-((4'-methoxybiphenyl-4-yl)methyl)pentaneamide (1.0 equiv) obtained in Example 31 was dissolved in a dichloromethane (DCM) solution, and cooled on ice. At 0° C., BBr₃ was slowly added, and the mixed solution was stirred at room temperature for 3 hours. The reaction was observed by TLC. After the reaction, ice was added to RBF, and extraction was performed with DCM. An organic solvent layer was separated, dehydrated with anhydrous magnesium sulfate (MgSO$_4$), filtered and then concentrated by evaporation. The concentrate was purified by MPLC, thereby obtaining a final product, N-(3-fluorophenyl)-N-((4'-hydroxybiphenyl-4-yl)methyl)pentaneamide (85% yield).

$^1$H-NMR (400 MHz, CDCl$_3$) δ 7.44-7.42 (4H, m); 7.35-7.29 (1H, m); 7.22 (2H, d, J=8.0 Hz); 7.06-7.02 (1H, m); 6.88 (2H, d, J=8.0 Hz); 6.85-6.78 (2H, m); 5.60 (1H, br, s); 4.90 (2H, s); 2.12 (2H, t); 1.65-1.57 (2H, m); 1.30-1.20 (2H, m); 0.83 (3H, t).

Example 33. Preparation of 2-(4'-((N-(3-fluorophenyl)pentaneamido)methyl)biphenyl-4-yloxy)acetic acid (AC-1074)

Ethyl (2-(4'-((N-(3-fluorophenyl)pentaneamido)methyl)biphenyl-4-yloxy)acetate) was prepared by the same method as described in Example 30 using the N-(3-fluorophenyl)-N-((4'-hydroxybiphenyl-4-yl)methyl)pentaneamide obtained in Example 32, thereby obtaining a final product, 2-(4'-((N-(3-fluorophenyl)pentaneamido)methyl)biphenyl-4-yloxy)acetic acid (80% yield).

$^1$H-NMR (CDCl$_3$, 400 MHz) δ 7.49-7.46 (4H, t); 7.39-7.37 (1H, m); 7.18-7.14 (4H, m); 7.01 (1H, d, J=8.0 Hz); 6.88 (2H, d, J=8.4 Hz); 4.86 (2H, s); 4.38 (2H, s); 2.09 (2H, m); 1.47-1.44 (2H, m); 1.19-1.13 (2H, m); 0.75 (3H, t).

Example 34. Preparation of N-(3-chlorophenyl)-N-((4'-methoxybiphenyl-4-yl)methyl)pentaneamide (AC-1628)

Step 1: Preparation of 4'-methoxybiphenyl-4-carbaldehyde

1-Bromo-4-methoxybenzene (1.0 equiv) and 4-formylphenylboronic acid (1.1 equiv) were thoroughly mixed in RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing was further performed for 15 minutes, the mixed solution was heated and refluxed for 4 hours. After the reaction, the mixture was filtered with ethyl acetate (EA), extracted, dehydrated with anhydrous MgSO$_4$, concentrated by evaporation, and purified by MPLC, thereby obtaining 4'-methoxybiphenyl-4-carbaldehyde (73% yield).

Step 2: Preparation of 3-chloro-N-((4'-methoxyphenyl-4-yl)methyl)aniline

The 4'-methoxybiphenyl-4-carbaldehyde (1.0 equiv) obtained in Step 1 and 3-chloroaniline (3-chloroaniline) (2.0 equiv) were dissolved in methanol, and stirred at room temperature for 4 hours. A reaction performed until an imine was formed was observed by TLC, and after the imine was formed, a methanol solution in which 1M NaCNBH$_3$ (1.0 equiv) and 0.5M ZnCl$_2$ (1.0 equiv) were mixed was added to the solution and stirred at room temperature overnight. After the reaction, the methanol was removed under a vacuum, a remaining solution was diluted with ethyl acetate (EA), and an organic solvent layer was washed with brine, dehydrated with anhydrous magnesium sulfate (MgSO$_4$) and concentrated by evaporation. The concentrate was purified by MPLC, thereby obtaining 3-chloro-N-((4'-methoxyphenyl-4-yl)methyl)aniline (97% yield).

Step 3: Preparation of N-(3-chlorophenyl)-N-((4'-methoxybiphenyl-4-yl)methyl)pentaneamide The 3-chloro-N-((4'-methoxyphenyl-4-yl)methyl)aniline obtained in Step 2 was dissolved in dichloromethane (DCM), mixed with triethanolamine (TEA), and cooled on ice. Valeroyl chloride (2.0 equiv) was added to the mixed solution, and then stirred at room temperature for 4 hours. After the reaction, RBF was added, and an organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining a final compound N-(3-chlorophenyl)-N-((4'-methoxybiphenyl-4-yl)methyl)pentaneamide (85% yield).

$^1$H-NMR (CDCl$_3$, 400 MHz) δ 7.52-7.49 (m, 2H); 7.46 (d, J=8.0 Hz, 2H); 7.30 (d, J=8.0 Hz, 2H) 7.22 (d, J=8.4 Hz, 2H); 7.06 (s, 1H); 6.98-6.94 (m, 2H); 6.88 (d, J=7.6 Hz, 1H); 4.88 (s, 2H); 3.84 (s, 3H); 2.08 (t, J=7.0 Hz, 2H); 1.65-1.56 (m, 2H); 1.29-1.20 (m, 2H); 0.83 (t, J=7.2 Hz, 3H).

Example 35. Preparation of N-(3-chlorophenyl)-N-((4'-hydroxybiphenyl-4-yl)methyl)pentaneamide (AC-1629)

The N-(3-chlorophenyl)-N-((4'-methoxybiphenyl-4-yl)methyl)pentaneamide (1.0 equiv) obtained in Example 34 was dissolved in a dichloromethane (DCM) solution, and cooled on ice. At 0° C., BBr$_3$ was slowly added, and the mixed solution was stirred at room temperature for 3 hours. The reaction was observed by TLC. After the reaction, ice was added to RBF, and extraction was performed with DCM. An organic solvent layer was separated, dehydrated with anhydrous magnesium sulfate (MgSO$_4$), filtered and then concentrated by evaporation. The concentrate was purified by MPLC, thereby obtaining a final product, N-(3-chlorophenyl)-N-((4'-hydroxybiphenyl-4-yl)methyl)pentaneamide (88% yield).

$^1$H NMR (400 MHz, CDCl$_3$) δ 7.43 (d, J=8.4 Hz, 4H); 7.32-7.25 (m, 2H); 7.21 (d, J=8.0 Hz, 2H); 7.08 (s, 1H); 6.91-6.85 (m, 3H); 5.49 (s, 1H); 4.88 (s, 2H); 2.10 (t, J=7.2 Hz, 2H); 1.64-1.57 (m, 2H); 1.27-1.22 (m, 2H); 0.83 (t, J=7.2 Hz, 3H).

Example 36. Preparation of 2-(4'-((N-(3-chlorophenyl)pentaneamido)methyl)biphenyl-4-yloxy)acetic acid (AC-1630)

Step 1: Preparation of ethyl 2-(4'-((N-(3-chlorophenyl)pentaneamido)methyl)biphenyl-4-yloxy)acetate The N-(3-chlorophenyl)-N-((4'-hydroxybiphenyl-4-yl)methyl)pentaneamide (1.0 equiv) obtained in Example 35 and K$_2$CO$_3$ (3.0 equiv) were dissolved in an N,N-dimethylformamide (DMF) solution, and cooled on ice. After adding ethyl chloroacetate (3.0 equiv), the mixed solution was stirred at room temperature under an N$_2$-supplying condition overnight. After the reaction, water was added, and a water-soluble layer was extracted with ethyl acetate (EA). An organic solvent layer was washed with brine, dehydrated with anhydrous magnesium sulfate (MgSO$_4$) and concentrated by evaporation. The concentrate was purified by MPLC, thereby obtaining ethyl 2-(4'-((N-(3-chlorophenyl)pentanamido)methyl)biphenyl-4-yloxy)acetate (75% yield).

Step 2: Preparation of 2-(4'-((N-(3-chlorophenyl)pentaneamido)methyl)biphenyl-4-yloxy)acetic acid The ethyl 2-(4'-((N-(3-chlorophenyl)pentaneamido)methyl)biphenyl-4-yloxy)acetate (1.0 equiv) obtained in Step 1 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, thereby obtaining a final product, 2-(4'-((N-(3-chlorophenyl)pentaneamido)methyl)biphenyl-4-yloxy)acetic acid (98% yield).
$^1$H-NMR (CDCl$_3$, 400 MHz) δ 7.40-7.37 (m, 3H); 7.23 (d, J=8.4 Hz, 2H); 7.16 (s, 1H); 6.97 (d, J=8.0 Hz, 2H); 4.89 (s, 2H); 4.70 (s, 2H); 2.11 (t, 2H); 1.52-1.45 (m, 2H); 1.23-1.16 (m, 2H); 0.78 (d, J=7.6 Hz, 3H).

Example 37. Preparation of N-(3-bromophenyl)-N-((4'-methoxybiphenyl-4-yl)methyl)pentaneamide (AC-1631)

Step 1: Preparation of 4'-methoxybiphenyl-4-carbaldehyde

1-Bromo-4-methoxybenzene (1.0 equiv) and 4-formylphenylboronic acid (1.1 equiv) were thoroughly mixed in RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing again for 15 minutes, the resulting solution was heated and refluxed for 4 hours. After the reaction, the mixture was filtered with ethyl acetate (EA), extracted, dehydrated with anhydrous MgSO$_4$, concentrated by evaporation, and purified by MPLC, thereby obtaining 4'-methoxybiphenyl-4-carbaldehyde (73% yield).

Step 2: Preparation of 3-bromo-N-((4'-methoxyphenyl-4-yl)methyl)aniline

The 4'-methoxybiphenyl-4-carbaldehyde (1.0 equiv) obtained in Step 1 and 3-bromoaniline (2.0 equiv) were dissolved in methanol, and stirred at room temperature for 4 hours. A reaction performed until an imine was formed was observed by TLC, and after the imine was formed, a methanol solution in which 1M NaCNBH$_3$ (1.0 equiv) and 0.5M ZnCl$_2$ (1.0 equiv) were mixed was added to the solution and stirred at room temperature overnight. After the reaction, the methanol was removed under a vacuum, the remaining solution was diluted with ethyl acetate (EA), and the organic solvent layer was washed with brine, dehydrated with anhydrous magnesium sulfate (MgSO$_4$) and concentrated by evaporation. The concentrate was purified by MPLC, thereby obtaining 3-bromo-N-((4'-methoxyphenyl-4-yl)methyl)aniline (97% yield).

Step 3: Preparation of N-(3-bromophenyl)-N-((4'-methoxybiphenyl-4-yl)methyl)pentanamide The 3-bromo-N-((4'-methoxyphenyl-4-yl)methyl)aniline obtained in Step 2 was dissolved in dichloromethane (DCM), mixed with triethanolamine (TEA), and cooled on ice. Valeroyl chloride (2.0 equiv) was added to the mixed solution, and then stirred at room temperature for 4 hours. After the reaction, RBF was added, and an organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining a final compound N-(3-bromophenyl)-N-((4'-methoxybiphenyl-4-yl)methyl)pentanamide (73% yield).
$^1$H-NMR (CDCl$_3$, 400 MHz) δ 7.51 (d, J=8.8 Hz, 2H); 7.46 (d, J=8.4 Hz, 3H); 7.23-7.18 (m, 4H); 6.96 (d, J=8.8 Hz, 2H); 6.91 (d, J=7.6 Hz, 1H); 4.88 (s, 2H); 3.84 (s, 3H); 2.08 (t, J=7.2 Hz, 2H); 1.61-1.55 (m, 2H); 1.27-1.21 (m, 2H); 0.83 (t, J=7.2 Hz, 3H).

Example 38. Preparation of N-(3-bromophenyl)-N-((4'-hydroxybiphenyl-4-yl)methyl)pentaneamide (AC-1632)

The N-(3-bromophenyl)-N-((4'-methoxybiphenyl-4-yl)methyl)pentaneamide (1.0 equiv) obtained in Example 37 was dissolved in a dichloromethane (DCM) solution, and cooled on ice. At 0° C., BBr$_3$ was slowly added, and the mixed solution was stirred at room temperature for 3 hours. The reaction was observed by TLC. After the reaction was completed, ice was added to RBF, and extraction was performed with DCM. The organic solvent layer was separated, dehydrated with anhydrous magnesium sulfate (MgSO$_4$), filtered and then concentrated by evaporation. The concentrate was purified by MPLC, thereby obtaining a final product, N-(3-bromophenyl)-N-((4'-hydroxybiphenyl-4-yl)methyl)pentaneamide (89% yield).
$^1$H-NMR (400 MHz, CDCl$_3$) δ 7.47-7.42 (m, 5H); 7.24-7.19 (m, 4H); 6.94 (d, J=7.6 Hz, 1H); 6.87 (d, J=8.0 Hz, 2H); 5.49 (s, 1H); 4.88 (s, 2H); 2.10 (t, J=7.2 Hz, 2H); 1.64-1.58 (m, 2H); 1.29-1.20 (m, 2H); 0.83 (t, J=7.2 Hz, 3H).

Example 39. Preparation of 2-(4'-((N-(3-bromophenyl)pentaneamido)methyl)biphenyl-4-yloxy)acetic acid (AC-1633)

Step 1: Preparation of ethyl 2-(4'-((N-(3-bromophenyl)pentaneamido)methyl)biphenyl-4-yloxy)acetate The N-(3-bromophenyl)-N-((4'-hydroxybiphenyl-4-yl)methyl)pentaneamide (1.0 equiv) obtained in Example 38 and K$_2$CO$_3$ (3.0 equiv) were dissolved in an N,N-dimethylformamide (DMF) solution, and cooled on ice. After adding ethyl chloroacetate (3.0 equiv), the mixed solution was stirred at room temperature under an N$_2$-supplying condition overnight. After the reaction, water was added, and the water-soluble layer was extracted with ethyl acetate (EA). The organic solvent layer was washed with brine, dehydrated with anhydrous magnesium sulfate (MgSO$_4$) and concentrated by evaporation. The concentrate was purified by MPLC, thereby obtaining ethyl 2-(4'-((N-(3-bromophenyl)pentaneamido)methyl)biphenyl-4-yloxy)acetate (85% yield).

Step 2: Preparation of 2-(4'-((N-(3-bromophenyl)pentaneamido)methyl)biphenyl-4-yloxy)acetic acid The ethyl 2-(4'-((N-(3-bromophenyl)pentaneamido)methyl)biphenyl-4-yloxy)acetate (1.0 equiv) obtained in Step 1 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, thereby obtaining a final product, 2-(4'-((N-(3-bromophenyl)pentaneamido)methyl)biphenyl-4-yloxy)acetic acid (87% yield).

$^1$H-NMR (CDCl$_3$, 400 MHz) δ 7.51 (d, J=8.8 Hz, 2H); 7.44 (d, J=8.8 Hz, 3H); 7.23-7.18 (m, 4H); 6.98 (d, J=8.0 Hz, 2H); 6.92 (d, J=8.0 Hz, 1H); 4.88 (s, 2H); 4.71 (s, 2H); 2.09 (t, 2H); 1.63-1.57 (m, 2H); 1.25-1.21 (m, 2H); 0.83 (t, J=7.2 Hz, 3H).

Example 40. Preparation of N-((4'-methoxybiphenyl-4-yl)methyl)-N-(3-(trifluoromethyl)phenyl)pentaneamide (AC-1634)

Step 1: Preparation of 4'-methoxybiphenyl-4-carbaldehyde

1-Bromo-4-methoxybenzene (1.0 equiv) and 4-formylphenylboronic acid (1.1 equiv) were thoroughly mixed in RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing was further performed for 15 minutes, the mixed solution was heated and refluxed for 4 hours. After the reaction, the mixture was filtered with ethyl acetate (EA), extracted, dehydrated with anhydrous MgSO$_4$, concentrated by evaporation, and purified by MPLC, thereby obtaining 4'-methoxybiphenyl-4-carbaldehyde (73% yield).

Step 2: Preparation of N-((4'-methoxybiphenyl-4-yl)methyl)-3-(trifluoromethyl)aniline The 4'-methoxybiphenyl-4-carbaldehyde (1.0 equiv) obtained in Step 1 and 3-(trifluoromethyl)aniline (3-(trifluoromethyl)aniline) (2.0 equiv) were dissolved in methanol, and stirred at room temperature for 4 hours. The reaction performed until an imine was formed was observed by TLC, and after the imine was formed, a methanol solution in which 1M NaCNBH$_3$ (1.0 equiv) and 0.5M ZnCl$_2$ (1.0 equiv) were mixed was added to the solution and stirred at room temperature overnight. After the reaction, the methanol was removed under a vacuum, the remaining solution was diluted with ethyl acetate (EA), and then the organic solvent layer was washed with brine, dehydrated with anhydrous magnesium sulfate (MgSO$_4$) and concentrated by evaporation. The concentrate was purified by MPLC, thereby obtaining N-((4'-methoxybiphenyl-4-yl)methyl)-3-(trifluoromethyl)aniline (93% yield).

Step 3: Preparation of N-((4'-methoxybiphenyl-4-yl)methyl)-N-(3-(trifluoromethyl)phenyl)pentaneamide The N-((4'-methoxybiphenyl-4-yl)methyl)-3-(trifluoromethyl)aniline obtained in Step 2 was dissolved in dichloromethane (DCM), mixed with triethanolamine (TEA), and cooled on ice. Valeroyl chloride (2.0 equiv) was added to the mixed solution, and then stirred at room temperature for 4 hours. After the reaction, RBF was added, and the organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining a final compound N-((4'-methoxybiphenyl-4-yl)methyl)-N-(3-(trifluoromethyl)phenyl)pentaneamide (75% yield).

$^1$H-NMR (CDCl$_3$, 400 MHz) δ 7.58 (d, J=7.6 Hz, 1H); 7.5 (dd, J=3.0, 11.8 Hz, 2H); 7.46 (d, J=7.6 Hz, 3H); 7.28 (s, 1H); 7.21 (d, J=8.0 Hz, 2H); 7.17 (d, J=7.2 Hz, 1H); 6.97 (dd, J=3.0, 11.8 Hz, 2H); 4.91 (s, 2H); 3.84 (s, 3H); 2.05 (s, 2H); 1.64-1.56 (m, 2H); 1.28-1.19 (m, 2H); 0.82 (t, J=7.6 Hz, 3H).

Example 41. Preparation of N-((4'-hydroxybiphenyl-4-yl)methyl)-N-(3-(trifluoromethyl)phenyl)pentaneamide (AC-1635)

The N-((4'-methoxybiphenyl-4-yl)methyl)-N-(3-(trifluoromethyl)phenyl)pentaneamide (1.0 equiv) obtained in Example 40 was dissolved in a dichloromethane (DCM) solution, and cooled on ice. At 0° C., BBr$_3$ was slowly added, and the mixed solution was stirred at room temperature for 3 hours. The reaction was observed by TLC. After the reaction, ice was added to RBF, and extraction was performed with DCM. The organic solvent layer was separated, dehydrated with anhydrous magnesium sulfate (MgSO$_4$), filtered and then concentrated by evaporation. The concentrate was purified by MPLC, thereby obtaining a final product, N-((4'-hydroxybiphenyl-4-yl)methyl)-N-(3-(trifluoromethyl)phenyl)pentaneamide (96% yield).

$^1$H-NMR (400 MHz, CDCl$_3$) δ 7.59 (d, J=7.6 Hz, 1H); 7.48 (d, J=7.6 Hz, 1H); 7.44 (d, J=8.4 Hz, 4H); 7.29 (s, 1H); 7.21 (q, 3H); 6.89 (d, J=11.6 Hz, 2H); 5.14 (s, 1H); 4.91 (s, 2H); 2.06 (t, 2H); 1.64-1.58 (m, 2H); 1.28-1.2 (m, 2H); 0.82 (t, J=7.4 Hz, 3H).

Example 42. Preparation of 2-(4'-((N-(3-(trifluoromethyl)phenyl)pentaneamido)methyl)biphenyl-4-yloxy)acetic acid (AC-1636)

Step 1: Preparation of ethyl 2-(4'-((N-(3-(trifluoromethyl)phenyl)pentaneamido)methyl)biphenyl-4-yloxy)acetate The N-((4'-hydroxybiphenyl-4-yl)methyl)-N-(3-(trifluoromethyl)phenyl)pentaneamide (1.0 equiv) obtained in Example 41 and K$_2$CO$_3$ (3.0 equiv) were dissolved in an N,N-dimethylformamide (DMF) solution, and cooled on ice. After adding ethyl bromoacetate (3.0 equiv), the mixed solution was stirred at room temperature under an N$_2$-supplying condition overnight. After the reaction, water was added, and the water-soluble layer was extracted with ethyl acetate (EA). The organic solvent layer was washed with brine, dehydrated with anhydrous magnesium sulfate (MgSO$_4$) and concentrated by evaporation. The concentrate was purified by MPLC, thereby obtaining ethyl 2-(4'-((N-(3-(trifluoromethyl)phenyl)pentaneamido)methyl)biphenyl-4-yloxy)acetate (100% yield).

Step 2: Preparation of 2-(4'-((N-(3-(trifluoromethyl)phenyl)pentaneamido)methyl)biphenyl-4-yloxy)acetic acid The 2-(4'-((N-(3-(trifluoro)phenyl)pentaneamido)methyl)biphenyl-4-yloxy)acetate (1.0 equiv) obtained in Step 1 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, thereby obtaining a final product, 2-(4'-((N-(3-(trifluoromethyl)phenyl)pentaneamido)methyl)biphenyl-4-yloxy)acetic acid (69% yield).

$^1$H-NMR (CDCl$_3$, 400 MHz) δ 7.59 (d, J=7.2 Hz, 1H); 7.52-7.43 (m, 5H); 7.28 (s, 1H); 7.21 (d, J=7.6 Hz, 3H); 6.99 (d, J=8.8 Hz, 2H); 4.93 (s, 2H); 4.77 (s, 2H); 2.08 (t, 2H); 1.62-1.54 (m, 2H); 1.23-1.19 (m, 2H); 0.82 (t, J=7.0 Hz, 3H).

Example 43. Preparation of N-((4'-methoxybiphenyl-4-yl)methyl)-N-m-tolylpentaneamide (AC-1637)

Step 1: Preparation of 4'-methoxybiphenyl-4-carbaldehyde

1-Bromo-4-methoxybenzene) (1.0 equiv) and 4-formylphenylboronic acid (1.1 equiv) were thoroughly mixed in RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing was further performed for 15 minutes, the mixed solution was heated and refluxed for 4 hours. After the reaction, the mixture was filtered with ethyl acetate (EA), extracted, dehydrated with anhydrous MgSO$_4$, concentrated by evaporation, and purified by MPLC, thereby obtaining 4'-methoxybiphenyl-4-carbaldehyde (73% yield).

Step 2: Preparation of N-((4'-methoxybiphenyl-4-yl)methyl)-3-(trifluoromethyl)aniline The 4'-methoxybiphenyl-4-carbaldehyde (1.0 equiv) obtained in Step 1 and m-toluidine (2.0 equiv) were dissolved in methanol, and stirred at room temperature for 4 hours. The reaction performed until an imine was formed was observed by TLC, and after the imine was formed, a methanol solution in which 1M NaCNBH$_3$ (1.0 equiv) and 0.5M ZnCl$_2$ (1.0 equiv) were mixed was added to the solution and stirred at room temperature overnight. After the reaction, the methanol was removed under a vacuum, a remaining solution was diluted with ethyl acetate (EA), and the organic solvent layer was washed with brine, dehydrated with anhydrous magnesium sulfate (MgSO$_4$) and concentrated by evaporation. The concentrate was purified by MPLC, thereby obtaining N-((4'-methoxybiphenyl-4-yl)methyl)-3-(trifluoromethyl)aniline (98% yield).

Step 3: Preparation of N-((4'-methoxybiphenyl-4-yl)methyl)-N-m-tolylpentaneamide The N-((4'-methoxybiphenyl-4-yl)methyl)-3-(trifluoromethyl)aniline obtained in Step 2 was dissolved in dichloromethane (DCM), mixed with triethanolamine (TEA), and cooled on ice. Valeroyl chloride (2.0 equiv) was added to the mixed solution, and then stirred at room temperature for 4 hours. After the reaction, RBF was added, and the organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining a final compound N-((4'-methoxybiphenyl-4-yl)methyl)-N-m-tolylpentaneamide (90% yield).

$^1$H-NMR (CDCl$_3$, 400 MHz) δ 7.51 (d, J=7.6 Hz, 2H); 7.45 (d, J=7.6 Hz, 2H); 7.21 (t, J=10.0 Hz, 2H); 7.11 (d, J=7.2 Hz, 1H); 6.97 (d, J=7.6 Hz, 2H); 6.84 (s, 1H); 6.78 (d, J=8.0 Hz, 1H); 4.88 (s, 2H); 3.848 (s, 3H); 2.31 (s, 3H); 2.08 (t, J=7.4 Hz, 2H); 1.63-1.55 (m, 2H); 1.26-1.20 (m, 2H); 0.82 (t, J=7.4 Hz, 3H).

Example 44. Preparation of N-((4'-hydroxybiphenyl-4-yl)methyl)-N-m-tolylpentaneamide (AC-1638)

The N-((4'-methoxybiphenyl-4-yl)methyl)-N-m-tolylpentanamide (1.0 equiv) obtained in Example 43 was dissolved in a dichloromethane (DCM) solution, and cooled on ice. At 0° C., BBr$_3$ was slowly added, the mixed solution was stirred at room temperature for 3 hours. The reaction was observed by TLC. After the reaction, ice was added to RBF, and extraction was performed with DCM. The organic solvent layer was separated, dehydrated with anhydrous magnesium sulfate (MgSO$_4$), filtered and then concentrated by evaporation. The concentrate was purified by MPLC, thereby obtaining a final product, N-((4'-hydroxybiphenyl-4-yl)methyl)-N-m-tolylpentaneamide (83% yield).

$^1$H-NMR (400 MHz, CDCl$_3$) δ 7.41-7.36 (m, 4H); 7.25-7.21 (m, 3H), 7.13 (d, J=7.6 Hz, 1H); 6.97 (s, br, 1H); 6.89 (s, 1H); 6.85 (d, J=6.8 Hz, 3H); 4.89 (s, 2H); 2.33 (s, 3H); 2.14 (t, J=7.6 Hz, 2H); 1.64-1.56 (m, 2H); 1.28-1.18 (m, 2H); 0.81 (t, J=7.2 Hz, 3H).

Example 45. Preparation of 2-(4'-((N-m-tolylpentanamido)methyl)biphenyl-4-yloxy)acetic acid (AC-1639)

Step 1: Preparation of ethyl 2-(4'-((N-m-tolylpentanamido)methyl)biphenyl-4-yloxy)acetate The N-((4'-hydroxyphenyl-4-yl)methyl)-N-m-tolylpentaneamide (1.0 equiv) obtained in Example 44 and K$_2$CO$_3$ (3.0 equiv) were dissolved in an N,N-dimethylformamide (DMF) solution, and cooled on ice. After adding ethyl chloroacetate (3.0 equiv), the mixed solution was stirred at room temperature under an N$_2$-supplying condition overnight. After the reaction, water was added, and the water-soluble layer was extracted with ethyl acetate (EA). The organic solvent layer was washed with brine, dehydrated with anhydrous magnesium sulfate (MgSO$_4$) and concentrated by evaporation. The concentrate was purified by MPLC, thereby obtaining ethyl 2-(4'-((N-m-tolylpentanamido)methyl)biphenyl-4-yloxy)acetate (100% yield).

Step 2: Preparation of 2-(4'-((N-m-tolylpentaneamido)methyl)biphenyl-4-yloxy)acetic acid The ethyl 2-(4'-((N-m-tolylpentaneamido)methyl)biphenyl-4-yloxy)acetate (1.0 equiv) obtained in Step 1 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, thereby obtaining a final product, 2-(4'-((N-m-tolylpentanamido)methyl)biphenyl-4-yloxy)acetic acid (62% yield).

$^1$H-NMR (CDCl$_3$, 400 MHz) δ 7.50 (d, J=8.8 Hz, 2H); 7.42 (s, 2H); 7.23 (t, J=7.4 Hz, 3H); 7.11 (d, J=7.2 Hz, 1H); 6.98 (d, J=8.4 Hz, 2H); 6.83 (s, 1H); 6.78 (d, J=7.6 Hz, 1H); 5.00 (s, 2H); 4.767 (s, 2H); 2.35 (s, 3H); 2.10 (t, J=7.6 Hz, 2H); 1.64-1.53 (m, 2H); 1.26-1.25 (m, 2H); 0.81 (t, J=6.0 Hz, 3H).

Example 46. Preparation of N-((4'-hydroxybiphenyl-4-yl)methyl)-N-(3-nitrophenyl)pentaneamide (AC-1641)

Step 1: Preparation of 4'-methoxybiphenyl-4-carbaldehyde

1-Bromo-4-methoxybenzene) (1.0 equiv) and 4-formylphenylboric acid (1.1 equiv) were thoroughly mixed in RBF, and dissolved in a 1,4-dioxane:$H_2O$ (10:1) mixed solution. Degassing was performed for 20 minutes by adding Pd(dppf)$Cl_2$.DCM (0.05 equiv) to the mixed solution, and performed again for 20 minutes by adding $Na_2CO_3$. After degassing was further performed for 15 minutes, the mixed solution was heated and refluxed for 4 hours. After the reaction, the mixture was filtered with ethyl acetate (EA), extracted, dehydrated with anhydrous $MgSO_4$, concentrated by evaporation, and purified by MPLC, thereby obtaining 4'-methoxybiphenyl-4-carbaldehyde (73% yield).

Step 2: Preparation of N-((4'-methoxybiphenyl-4-yl)methyl)-3-nitroaniline

The 4'-methoxybiphenyl-4-carbaldehyde (1.0 equiv) obtained in Step 1 and 3-nitroaniline (2.0 equiv) were dissolved in methanol, and stirred at room temperature for 4 hours. A reaction performed until an imine was formed was observed by TLC, and after the imine was formed, a methanol solution in which 1M NaCN$BH_3$ (1.0 equiv) and 0.5M Zn$Cl_2$ (1.0 equiv) were mixed was added to the solution and stirred at room temperature overnight. After the reaction, the methanol was removed under a vacuum, a remaining solution was diluted with ethyl acetate (EA), and the organic solvent layer was washed with brine, dehydrated with anhydrous magnesium sulfate ($MgSO_4$) and concentrated by evaporation. The concentrate was purified by MPLC, thereby obtaining a yellow solid N-((4'-methoxybiphenyl-4-yl)methyl)-3-nitroaniline (97% yield).

Step 3: Preparation of N-((4'-methoxybiphenyl-4-yl)methyl)-N-(3-nitrophenyl)pentaneamide The N-((4'-methoxybiphenyl-4-yl)methyl)-3-nitroaniline obtained in Step 2 was dissolved in dichloromethane (DCM), mixed with triethanolamine (TEA), and cooled on ice. Valeroyl chloride (2.0 equiv) was added to the mixed solution, and then stirred at room temperature for 4 hours. After the reaction, RBF was added, and the organic solvent layer was washed with brine and separated. Afterward, the organic solvent layer was collected, dehydrated with anhydrous magnesium sulfate ($MgSO_4$), filtered, and concentrated by evaporation. The concentrate was purified by MPLC, thereby obtaining N-((4'-methoxybiphenyl-4-yl)methyl)-N-(3-nitrophenyl)pentaneamide (91% yield).

Step 4: Preparation of N-((4'-hydroxyphenyl-4-yl)methyl)-N-(3-nitrophenyl)pentaneamide The N-((4'-methoxybiphenyl-4-yl)methyl)-N-(3-nitrophenyl)pentaneamide (1.0 equiv) obtained in Step 3 was dissolved in a dichloromethane (DCM) solution, and cooled on ice. At 0° C., $BBr_3$ was slowly added, and the mixed solution was stirred at room temperature for 3 hours. The reaction was observed by TLC. After the reaction, ice was added to RBF, and extraction was performed with DCM. The organic solvent layer was separated, dehydrated with anhydrous magnesium sulfate ($MgSO_4$), filtered and then concentrated by evaporation. The concentrate was purified by MPLC, thereby obtaining a final product, N-((4'-hydroxyphenyl-4-yl)methyl)-N-(3-nitrophenyl)pentaneamide (30% yield).

$^1$H NMR (400 MHz, CDCl$_3$) δ 8.18 (d, J=8.8 Hz, 1H); 7.95 (s, 1H); 7.52 (t, J=8.2 Hz, 1H); 7.44 (d, J=8.0 Hz, 4H); 7.33 (s, 1H); 7.21 (d, J=8.0 Hz, 2H); 6.97 (d, J=8.0 Hz, 2H); 4.95 (s, 2H); 4.89 (s, 1H); 2.09 (t, 2H); 1.66-1.54 (m, 2H); 1.27-1.22 (m, 2H); 0.86 (t, J=9.2 Hz, 3H).

Example 47. Preparation of 2-(4'-((N-(3-nitrophenyl)pentaneamido)methyl)biphenyl-4-yloxy)acetic acid (AC-1642)

Step 1: Preparation of ethyl 2-(4'-((N-(3-nitrophenyl)pentaneamido)methyl)biphenyl-4-yloxy)acetate The N-((4'-hydroxyphenyl-4-yl)methyl)-N-(3-nitrophenyl)pentaneamide (1.0 equiv) obtained in Example 46 and $K_2CO_3$ (3.0 equiv) were dissolved in an N,N-dimethylformamide (DMF) solution, and cooled on ice. After adding ethyl chloroacetate (3.0 equiv), the mixed solution was stirred at room temperature under an $N_2$-supplying condition overnight. After the reaction, water was added, and the water-soluble layer was extracted with ethyl acetate (EA). The organic solvent layer was washed with brine, dehydrated with anhydrous magnesium sulfate ($MgSO_4$) and concentrated by evaporation. The concentrate was purified by MPLC, thereby obtaining ethyl 2-(4'-((N-(3-nitrophenyl)pentaneamido)methyl)biphenyl-4-yloxy)acetate (91% yield).

Step 2: Preparation of 2-(4'-((N-(3-nitrophenyl)pentaneamido)methyl)biphenyl-4-yloxy)acetic acid The ethyl 2-(4'-((N-(3-nitrophenyl)pentaneamido)methyl)biphenyl-4-yloxy)acetate (1.0 equiv) obtained in Step 1 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, thereby obtaining the final product, 2-(4'-((N-(3-nitrophenyl)pentaneamido)methyl)biphenyl-4-yloxy)acetic acid (49% yield).

$^1$H-NMR (CDCl$_3$, 400 MHz) δ 8.15 (d, J=7.2 Hz, 1H); 8.10 (s, 1H); 7.69-7.63 (m, 2H); 7.55 (t, J=8.2 Hz, 4H); 7.25 (d, J=8.0 Hz, 2H); 6.97 (d, J=8.4 Hz, 2H); 4.97 (s, 2H); 4.70 (s, 2H); 2.15 (t, 2H); 1.53-1.46 (m, 2H); 1.24-1.17 (m, 2H); 0.78 (t, J=7.2 Hz, 3H).

Example 48. Preparation of N-(3-iodophenyl)-N-((4'-methoxybiphenyl-4-yl)methyl)pentaneamide (AC-1643)

Step 1: Preparation of 4'-methoxybiphenyl-4-carbaldehyde

1-Bromo-4-methoxybenzene) (1.0 equiv) and 4-formylphenylboronic acid (1.1 equiv) were thoroughly mixed in RBF, and dissolved in a 1,4-dioxane:$H_2O$ (10:1) mixed solution. Degassing was performed for 20 minutes by adding Pd(dppf)$Cl_2$.DCM (0.05 equiv) to the mixed solution, and performed again for 20 minutes by adding $Na_2CO_3$. After degassing was further performed for 15 minutes, the mixed solution was heated and refluxed for 4 hours. After the reaction was completed, the mixture was filtered with ethyl acetate (EA), extracted, dehydrated with anhydrous MgSO$_4$, concentrated by evaporation, and purified by MPLC, thereby obtaining 4'-methoxybiphenyl-4-carbaldehyde (73% yield).

Step 2: Preparation of 3-iodo-N-((4'-methoxybiphenyl-4-yl)methyl)aniline

The 4'-methoxybiphenyl-4-carbaldehyde (1.0 equiv) obtained in Step 1 and 3-iodoaniline (3-iodoaniline) (2.0 equiv) were dissolved in methanol, and stirred at room temperature for 4 hours. A reaction performed until an imine was formed was observed by TLC, and after the imine was formed, the methanol solution, in which 1M NaCNBH$_3$ (1.0 equiv) and 0.5M ZnCl$_2$ (1.0 equiv) were mixed, was added to the solution and stirred at room temperature overnight. After the reaction, the methanol was removed under a vacuum, a remaining solution was diluted with ethyl acetate (EA), and the organic solvent layer was washed with brine, dehydrated with anhydrous magnesium sulfate (MgSO$_4$) and concentrated by evaporation. The concentrate was purified by MPLC, thereby obtaining 3-iodo-N-((4'-methoxybiphenyl-4-yl)methyl)aniline (95% yield).

Step 3: Preparation of N-(3-iodophenyl)-N-((4'-methoxybiphenyl-4-yl)methyl)pentaneamide The 3-iodo-N-((4'-methoxybiphenyl-4-yl)methyl)aniline obtained in Step 2 was dissolved in dichloromethane (DCM), mixed with triethanolamine (TEA), and cooled on ice. Valeroyl chloride (2.0 equiv) was added to the mixed solution, and then stirred at room temperature for 4 hours. After the reaction, RBF was added, and the organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining a final compound, N-(3-iodophenyl)-N-((4'-methoxybiphenyl-4-yl)methyl)pentaneamide (80% yield).

$^1$H-NMR (CDCl$_3$, 400 MHz) δ 7.64 (d, J=8.0 Hz, 1H); 7.51 (d, J=8.8 Hz, 2H); 7.46 (d, J=8.4 Hz, 2H); 7.41 (s, 1H); 7.21 (d, J=8.0 Hz, 2H); 7.06 (t, J=8.0 Hz, 1H); 6.96 (d, J=8.8 Hz, 3H); 4.87 (s, 2H); 3.84 (s, 2H); 2.07 (t, J=7.0 Hz, 2H); 1.63-4.57 (m, 2H); 1.29-1.2 (m, 2H); 0.83 (t, J=7.4 Hz, 3H).

Example 49. Preparation of N-((4'-hydroxybiphenyl-4-yl)methyl)-N-(3-iodophenyl)pentaneamide (AC-1644)

The N-(3-iodophenyl)-N-((4'-methoxybiphenyl-4-yl)methyl)pentaneamide (1.0 equiv) obtained in Example 48 was dissolved in a dichloromethane (DCM) solution, and cooled on ice. At 0° C., BBr$_3$ was slowly added, and the mixed solution was stirred at room temperature for 3 hours. The reaction was observed by TLC. After the reaction, ice was added to RBF, and extraction was performed with DCM. The organic solvent layer was separated, dehydrated with anhydrous magnesium sulfate (MgSO$_4$), filtered and then concentrated by evaporation. The concentrate was purified by MPLC, thereby obtaining a final product, N-((4'-hydroxybiphenyl-4-yl)methyl)-N-(3-iodophenyl)pentanamide (90% yield).

$^1$H-NMR (CDCl$_3$, 400 MHz) δ 7.65 (d, J=8.0 Hz, 1H); 7.46-7.43 (m, 5H); 7.21 (d, J=7.6 Hz, 2H); 7.06 (t, J=8.0 Hz, 1H); 6.95 (d, J=8.8 Hz, 1H); 6.86 (d, J=8.4 Hz, 2H); 5.08 (s, 1H); 4.871 (s, 2H); 2.07 (t, 2H); 1.63-1.59 (m, 2H); 1.29-1.21 (m, 2H); 0.86 (t, 3H).

Example 50. Preparation of 2-(4'-((N-(3-iodophenyl)pentaneamido)methyl)biphenyl-4-yloxy)acetic acid (AC-1645)

Step 1: Preparation of ethyl 2-(4'-((N-(3-iodophenyl)pentaneamido)methyl)biphenyl-4-yloxy)acetate N-(3-iodophenyl)-N-((4'-hydroxybiphenyl-4-yl)methyl)pentaneamide (1.0 equiv) and K$_2$CO$_3$ (3.0 equiv) were dissolved in an N,N-dimethylformamide (DMF) solution, and cooled on ice. After adding ethyl chloroacetate (3.0 equiv), the mixed solution was stirred at room temperature under an N$_2$-supplying condition overnight. After the reaction, water was added, and the water-soluble layer was extracted with ethyl acetate (EA). The organic solvent layer was washed with brine, dehydrated with anhydrous magnesium sulfate (MgSO$_4$) and concentrated by evaporation. The concentrate was purified by MPLC, thereby obtaining ethyl 2-(4'-((N-(3-iodophenyl)pentaneamido)methyl)biphenyl-4-yloxy)acetate (89% yield).

Step 2: Preparation of 2-(4'-((N-(3-iodophenyl)pentaneamido)methyl)biphenyl-4-yloxy)acetic acid The ethyl 2-(4'-((N-(3-iodophenyl)pentaneamido)methyl)biphenyl-4-yloxy)acetate (1.0 equiv) obtained in Step 1 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, thereby obtaining a final product, 2-(4'-((N-(3-iodophenyl)pentaneamido)methyl)biphenyl-4-yloxy)acetic acid (94% yield).

$^1$H-NMR (CDCl$_3$, 400 MHz) δ 7.65 (d, J=7.6 Hz, 1H); 7.51 (d, J=8.8 Hz, 2H); 7.43 (t, J=8.8 Hz, 3H); 7.21 (d, J=8.0 Hz, 2H); 7.06 (t, J=7.8 Hz, 1H); 6.98 (d, J=8.4 Hz, 2H); 6.94 (d, J=8.0 Hz, 1H); 4.87 (s, 2H); 4.71 (s, 2H); 2.1 (t, 2H); 1.63-1.55 (m, 2H); 1.26-1.19 (m, 2H); 0.83 (t, J=7.2 Hz, 3H).

Example 51. Preparation of N-(3-fluorophenyl)-N-((4'-methoxybiphenyl-4-yl)methyl) pentaneamide (AC-1646)

Step 1: Preparation of 4'-methoxybiphenyl-4-carbaldehyde 1-Bromo-4-methoxybenzene) (1.0 equiv) and 4-formylphenylboronic acid (4-Formylphenylboronic acid) (1.1 equiv) were thoroughly mixed in RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing was further performed for 15 minutes, the mixed solution was heated and refluxed for 4 hours. After the reaction, the mixture was filtered with ethyl acetate (EA), extracted, dehydrated with anhydrous MgSO$_4$, concentrated by evaporation, and purified by MPLC, thereby obtaining 4'-methoxybiphenyl-4-carbaldehyde (73% yield).

Step 2: Preparation of 3-fluoro-N-((4'-methoxybiphenyl-4-yl)methyl)aniline

The 4'-methoxybiphenyl-4-carbaldehyde (1.0 equiv.) obtained in Step 1 and 3-fluoroaniline (2.0 equiv.) were dissolved in methanol, and stirred at room temperature for 4 hours. The reaction performed until an imine was formed was observed by TLC, and after the imine was formed, the methanol solution in which 1M NaCNBH$_3$ (1.0 equiv) and 0.5M ZnCl$_2$ (1.0 equiv) were mixed was added to the solution and stirred at room temperature overnight. After the reaction, the methanol was removed under a vacuum, a remaining solution was diluted with ethyl acetate (EA), and the organic solvent layer was washed with brine, dehydrated with anhydrous magnesium sulfate (MgSO$_4$) and concentrated by evaporation. The concentrate was purified by MPLC, thereby obtaining 3-fluoro-N-((4'-methoxybiphenyl-4-yl)methyl)aniline (63% yield).

Step 3: Preparation of N-(3-fluorophenyl)-N-((4'-methoxybiphenyl-4-yl)methyl)pentaneamide The 3-fluoro-N-((4'-methoxybiphenyl-4-yl)methyl)aniline obtained in Step 2 was dissolved in dichloromethane (DCM), mixed with triethanolamine (TEA), and cooled on ice.

Valeroyl chloride (2.0 equiv) was added to the mixed solution, and then stirred at room temperature for 4 hours. After the reaction, RBF was added, and the organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining a final compound, N-(3-fluorophenyl)-N-((4'-methoxybiphenyl-4-yl)methyl)pentaneamide (81% yield).

$^1$H-NMR (CDCl$_3$, 400 MHz) δ 7.51 (d, J=8.8 Hz, 2H); 7.46 (d, J=8.0 Hz, 2H); 7.31 (q, J=7.6 Hz, 1H); 7.25 (d, J=8.4 Hz, 2H); 7.03 (t, J=7.6 Hz, 1H); 6.97 (d, J=8.8 Hz, 2H); 6.81 (dd, J=8.4, 20.0 Hz, 2H); 4.90 (s, 2H); 3.85 (s, 3H); 1.93 (s, 3H).

Example 52. Preparation of N-(3-fluorophenyl)-N-((4'-hydroxy-[1,1'-biphenyl]-4-yl)methyl)acetamide (AC-1647)

The N-((4'-hydroxybiphenyl-4-yl)methyl)-N-(3-iodophenyl)pentaneamide (1.0 equiv) obtained in Example 51 was dissolved in a dichloromethane (DCM) solution, and cooled on ice. At 0° C., BBr$_3$ was slowly added, and the mixed solution was stirred at room temperature for 3 hours. The reaction was observed by TLC. After the reaction, ice was added to RBF, and extraction was performed with DCM. The organic solvent layer was separated, dehydrated with anhydrous magnesium sulfate (MgSO$_4$), filtered and then concentrated by evaporation. The concentrate was purified by MPLC, thereby obtaining the final product, N-(3-fluorophenyl)-N-((4'-hydroxy-[1,1'-biphenyl]-4-yl)methyl)acetamide (69% yield).

$^1$H NMR (400 MHz, CDCl$_3$) δ 7.45 (d, J=8.8 Hz, 4H); 7.32 (q, J=7.3 Hz, 1H); 7.24 (d, J=8.0 Hz, 2H); 7.04 (t, J=8.2 Hz, 1H); 6.89 (d, J=7.2 Hz, 2H); 6.84 (d, J=7.2 Hz, 1H); 6.79 (d, J=8.8 Hz, 1H); 5.013 (s, 1H); 4.90 (s, 2H); 1.93 (s, 3H)

Example 53. Preparation of 2-((4'-((N-(3-fluorophenyl)acetamido)methyl)-[1,1'-biphenyl]-4-yl)oxy)acetic acid (AC-1648)

Step 1: Preparation of ethyl 2-(4'-((N-(3-fluorophenyl)acetamido)methyl)biphenyl-4-yloxy)acetate The N-(3-fluorophenyl)-N-((4'-hydroxy-[1,1'-biphenyl]-4-yl)methyl)acetamide (1.0 equiv) obtained in Example 52 and K$_2$CO$_3$ (3.0 equiv) were dissolved in an N,N-dimethylformamide (DMF) solution, and cooled on ice. After adding ethyl chloroacetate (3.0 equiv), a mixed solution was stirred at room temperature under an N$_2$-supplying condition overnight. After the reaction, water was added, and the water-soluble layer was extracted with ethyl acetate (EA). The organic solvent layer was washed with brine, dehydrated with anhydrous magnesium sulfate (MgSO$_4$) and concentrated by evaporation. The concentrate was purified by MPLC, thereby obtaining ethyl 2-(4'-((N-(3-fluorophenyl)acetamido)methyl)biphenyl-4-yloxy)acetate (91% yield).

Step 2: Preparation of 2-((4'-((N-(3-fluorophenyl)acetamido)methyl)-[1,1'-biphenyl]-4-yl)oxy)acetic acid The ethyl 2-(4'-((N-(3-fluorophenyl)acetoamido)methyl)biphenyl-4-yloxy)acetate (1.0 equiv) obtained in Step 1 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, thereby obtaining the final product, 2-((4'-((N-(3-fluorophenyl)acetamido)methyl)-[1,1'-biphenyl]-4-yl)oxy)acetic acid (67% yield).

$^1$H-NMR (CDCl$_3$, 400 MHz) δ 7.54 (d, J=8.0 Hz, 2H); 7.50 (d, J=8.4 Hz, 2H); 7.39 (q, J=7.3 Hz, 1H); 7.24 (d, J=8.0 Hz, 2H); 7.11 (t, J=9.2 Hz, 1H); 7.00 (d, J=8.4 Hz, 2H); 6.96 (d, J=7.6 Hz, 2H); 4.93 (s, 2H); 4.69 (s, 2H); 1.93 (s, 3H)

Example 54. Preparation of N-((4'-(4-isopropylpiperazine-1-carbonyl)biphenyl-4-yl)methyl)-N-phenyl-pentaneamide (AC-1649)

Step 1: Preparation of methyl 4'-formyl biphenyl-4-carboxylate

1-Bromo-4-methoxybenzene (1.0 equiv) and methyl 4-bromobenzoate (1.1 equiv) were thoroughly mixed in RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing was further performed for 15 minutes, the mixed solution was heated and refluxed for 4 hours. After the reaction, the mixture was filtered with ethyl acetate (EA), extracted, dehydrated with anhydrous MgSO$_4$, concentrated by evaporation, and purified by MPLC, thereby obtaining methyl 4'-formylbiphenyl-4-carboxylate (73% yield).

Step 2: Preparation of methyl 4'-((phenylamino)methyl)biphenyl-4-carboxylate(methyl 4'-((phenylamino)methyl)biphenyl-4-carboxylate The methyl 4'-formylbiphenyl-4-carboxylate (1.0 equiv) obtained in Step 1 and aniline (3.0 equiv) were dissolved in methanol, and stirred at room temperature for 4 hours. A reaction performed until an imine was formed was observed by TLC, and after the imine was formed, the methanol solution in which 1M NaCNBH$_3$ (1.0 equiv) and 0.5M ZnCl$_2$ (1.0 equiv) were mixed was added to the solution and stirred at room temperature overnight. After the reaction, the methanol was removed under a vacuum, the remaining solution was diluted with ethyl acetate (EA), and the organic solvent layer was washed with brine, dehydrated with anhydrous magnesium sulfate (MgSO$_4$) and concentrated by evaporation. The concentrate was purified by MPLC, thereby obtaining methyl 4'-((phenylamino)methyl)biphenyl-4-carboxylate (51% yield).

Step 3: Preparation of methyl 4'-((N-phenylpentanamido)methyl)biphenyl-4-carboxylate The methyl 4'-((phenylamino)methyl)biphenyl-4-carboxylate obtained in Step 2 was dissolved in dichloromethane (DCM), mixed with triethanolamine (TEA), and cooled on ice. Valeroyl chloride (2.0 equiv) was added to the mixed solution, and then stirred at room temperature for 4 hours. After the reaction, RBF was added, and the organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining methyl 4'-((N-phenylpentanamido)methyl)biphenyl-4-carboxylate (57% yield).

Step 4: Preparation of 4'-((N-phenylpentaneamido)methyl)biphenyl-4-carboxylic acid The methyl 4'-((N-phenylpentaneamido)methyl)biphenyl-4-carboxylate (1.0 equiv) obtained in Step 3 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed and recrystallized, thereby obtaining 4'-((N-phenylpentaneamido)methyl)biphenyl-4-carboxylic acid (97% yield).

Step 5: Preparation of 4'-((N-phenylpentaneamido)methyl)biphenyl-4-carboxylic acid The 4'-((N-phenylpentaneamido)methyl)biphenyl-4-carboxylic acid (1.0 equiv) obtained in Step 4, 1-isopropylpiperazine (0.9 equiv), HATU (1.2 equiv) and N,N-diisopropylethylamine (DIPEA) (2.5 equiv) were dissolved in N,N-dimethylformamide (DMF), and the mixed solution was stirred at room temperature overnight. After the reaction, water was added, and the water-soluble layer was extracted with ethyl acetate (EA). The organic solvent layer was filtered and then concentrated by evaporation. The concentrate was purified by column chromatography, thereby obtaining the final product, 4'-((N-phenylpentaneamido)methyl)biphenyl-4-carboxylic acid (50% yield).

$^1$H-NMR (CDCl$_3$, 400 MHz) δ 7.60 (d, J=8.0 Hz, 2H), 7.49 (m, J=4.8 Hz, 4H), 7.36 (d, J=6.4 Hz, 3H), 7.29 (d, J=8.4 Hz, 2H), 7.02 (d, J=6.8 Hz, 2H), 4.92 (s, 2H), 3.65 (d, 4H), 2.74 (m, 1H), 2.55 (d, 4H), 2.09 (t, J=7.6 Hz, 2H), 1.60 (m, 2H), 1.22 (m, 2H), 1.06 (d, J=6.8 Hz, 6H), 0.82 (t, J=7.4 Hz, 3H).

Example 55. Preparation of N-(4-fluorophenyl)-N-((4'-(4-isopropylpiperazine-1-carbonyl)biphenyl-4-yl)methyl)pentaneamide (AC-1650)

Step 1: Preparation of methyl 4'-formylbiphenyl-4-carboxylate

1-Bromo-4-methoxybenzene (1.0 equiv) and methyl 4-bromobenzoate (1.1 equiv) were thoroughly mixed with RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing again for 15 minutes, the resulting solution was heated and refluxed for 4 hours. After the reaction, the mixture was filtered with ethyl acetate (EA), extracted, dehydrated with anhydrous MgSO$_4$, concentrated by evaporation, and purified by MPLC, thereby obtaining methyl 4'-formylbiphenyl-4-carboxylate (73% yield).

Step 2: Preparation of methyl 4'-((4-fluorophenylamino)methyl)biphenyl-4-carboxylate The 4'-formylbiphenyl-4-carboxylate (1.0 equiv) obtained in Step 1 and 3-bromoaniline (3.0 equiv) were dissolved in methanol, and stirred at room temperature for 4 hours. A reaction until an imine was produced was observed by TLC, after imine was produced, the methanol solution, in which 1M NaCNBH$_3$ (1.0 equiv) was mixed with 0.5M ZnCl$_2$ (1.0 equiv), was added to the solution, and then the solution was stirred at room temperature overnight. After the reaction, the methanol was removed under a vacuum, the remaining solution was diluted with ethyl acetate (EA), and the organic solvent layer was washed with brine, dehydrated with anhydrous magnesium sulfate (MgSO$_4$) and concentrated by evaporation. The concentrate was purified by MPLC, thereby obtaining methyl 4'-((4-fluorophenylamino)methyl)biphenyl-4-carboxylate (51% yield).

Step 3: Preparation of methyl 4'-((N-(4-fluorophenyl)pentaneamido)methyl)biphenyl-4-carboxylate The 4'-((4-fluorophenylamino)methyl)biphenyl-4-carboxylate obtained in Step 2 was dissolved in dichloromethane (DCM), mixed with triethanolamine (TEA), and cooled on ice. Valeroyl chloride (2.0 equiv) was added to the mixed solution, and stirred at room temperature for 12 hours. After the reaction, RBF was added, and the organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining methyl 4'-((N-(4-fluorophenyl)pentaneamido)methyl)biphenyl-4-carboxylate (85% yield).

Step 4: Preparation of 4'-((N-(4-fluorophenyl)pentaneamido)methyl)biphenyl-4-carboxylic acid The methyl 4'-((N-(4-fluorophenyl)pentaneamido)methyl)biphenyl-4-carboxylate (1.0 equiv) obtained in Step 3 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed, thereby obtaining 4'-((N-(4-fluorophenyl)pentaneamido)methyl)biphenyl-4-carboxylic acid (90% yield).

Step 5: Preparation of N-(4-fluorophenyl)-N-((4'-(4-isopropylpiperazine-1-carbonyl)biphenyl-4-yl)methyl)pentaneamide The 4'-((N-(4-fluorophenyl)pentaneamido)methyl)biphenyl-4-carboxylic acid (1.0 equiv) obtained in Step 4 and 1-isopropylpiperazine (0.9 equiv), EDC (1.2 equiv), HoBt (1.2 equiv) and N,N-diisopropylethylamine (DIPEA) (2.5 equiv) were dissolved in N,N-dimethylformamide (DMF), and the mixed solution was stirred at room temperature overnight. After the reaction, water was added, and the water-soluble layer was extracted with ethyl acetate (EA). The organic solvent layer was filtered and then concentrated by evaporation. The concentrate was purified by column chromatography, thereby obtaining a final product, N-(4-fluorophenyl)-N-((4'-(4-isopropylpiperazine-1-carbonyl)biphenyl-4-yl)methyl)pentaneamide (41% yield).

$^1$H-NMR (400 MHz, CDCl$_3$) δ 7.60 (d, J=8.4 Hz, 2H), 7.49 (m, J=6.0 Hz, 4H), 7.27 (d, J=8.0 Hz, 2H), 7.00 (m, J=6.7 Hz, 4H), 4.89 (s, 2H), 3.67 (d, 4H), 2.77 (m, 1H), 2.57 (d, 4H), 2.07 (t, J=7.2 Hz, 2H), 1.59 (m, 2H), 1.23 (m, 2H), 1.07 (d, J=6.0 Hz, 6H); 0.83 (t, J=7.4 Hz, 3H).

Example 56. Preparation of N-((3'-(4-isopropylpiperazine-1-carbonyl)biphenyl-4-yl)methyl)-N-phenylpentaneamide (AC-1651)

Step 1: Preparation of methyl 4'-formylbiphenyl-3-carboxylate

Methyl 3-bromobenzoate (1.0 equiv) and 4-formylphenylboronic acid (1.1 equiv) were thoroughly mixed in RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing was further performed for 15 minutes, the mixed solution was heated and refluxed for 4 hours. After the reaction, the mixture was filtered with ethyl acetate (EA), extracted, dehydrated with anhydrous MgSO$_4$, concentrated by evaporation, and purified by MPLC, thereby obtaining methyl 4'-formylbiphenyl-3-carboxylate (91% yield).

Step 2: Preparation of methyl 4'-((phenylamino)methyl)biphenyl-3-carboxylate The methyl 4'-formylbiphenyl-3-carboxylate (1.0 equiv) obtained in Step 1 and aniline (3.0 equiv) were dissolved in methanol, and stirred at room temperature for 4 hours. A reaction performed until an imine was formed was observed by TLC, and after the imine was formed, a methanol solution, in which 1M NaCNBH$_3$ (1.0 equiv) and 0.5M ZnCl$_2$ (1.0 equiv) were mixed, was added to the solution and stirred at room temperature overnight. After the reaction, the methanol was removed under a vacuum, the remaining solution was diluted with ethyl acetate (EA), and the organic solvent layer was washed with brine, dehydrated with anhydrous magnesium sulfate (MgSO$_4$) and concentrated by evaporation. The concentrate was purified by MPLC, thereby obtaining methyl 4'-((phenylamino)methyl)biphenyl-3-carboxylate (95% yield).

Step 3: Preparation of methyl 4'-((N-phenylpentaneamido)methyl)biphenyl-3-carboxylate The methyl 4'-((phenylamino)methyl)biphenyl-3-carboxylate obtained in Step 2 was dissolved in dichloromethane (DCM), mixed with triethanolamine (TEA), and cooled on ice. Valeroyl chloride (2.0 equiv) was added to the mixed solution, and then stirred at room temperature for 4 hours. After the reaction, RBF was added, and the organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining methyl 4'-((N-phenylpentaneamido)methyl)biphenyl-3-carboxylate (96% yield).

Step 4: Preparation of 4'-((N-phenylpentaneamido)methyl)biphenyl-3-carboxylic acid The methyl 4'-((N-phenylpentanamido)methyl)biphenyl-3-carboxylate (1.0 equiv) obtained in Step 3 was thoroughly mixed in a tetrahydrofuran (THF) solution, mixed with an LiOH solution, and stirred for 4 hours. After the reaction, the mixed solution was concentrated, mixed with 2N HCl until becoming an acidic state, and extracted with ethyl acetate (EA). Under a vacuum, the organic solvent layer was removed and recrystallized, thereby obtaining 4'-((N-phenylpentanamido)methyl)biphenyl-3-carboxylic acid (95% yield).

Step 5: Preparation of N-((3'-(4-isopropylpiperazine-1-carbonyl)biphenyl-4-yl)methyl)-N-phenylpentaneamide The 4'-((N-phenylpentaneamido)methyl)biphenyl-3-carboxylic acid (1.0 equiv) obtained in Step 4 and 1-isopropylpiperazine (0.9 equiv), EDC (1.2 equiv), HoBt (1.2 equiv) and N,N-diisopropylethylamine (DIPEA) (2.5 equiv) were dissolved in N,N-dimethylformamide (DMF), and the mixed solution was stirred at room temperature overnight. After the reaction, water was added, and the water-soluble layer was extracted with ethyl acetate (EA). The organic solvent layer was filtered and then concentrated by evaporation. The concentrate was purified by column chromatography, thereby obtaining the final product, N-((3'-(4-isopropylpiperazine-1-carbonyl)biphenyl-4-yl)methyl)-N-phenylpentaneamide (70% yield).

$^1$H-NMR (CDCl$_3$, 400 MHz) δ 7.61 (d, J=6.8 Hz, 2H), 7.49 (d, J=7.6 Hz, 2H), 7.45 (d, 1H), 7.354 (m, 4H), 7.28 (s, 2H), 7.01 (d, J=7.2 Hz, 2H), 4.92 (s, 2H), 3.64 (d, 4H), 2.72 (m, 1H), 2.53 (d, 4H), 2.09 (t, J=7.4 Hz, 2H), 1.59 (m, 2H), 1.23 (m, 2H), 1.05 (d, J=6.8 Hz, 6H), 0.82 (t, J=7.2 Hz, 3H).

Example 57. Preparation of N-(4-fluorophenyl)-N-((3'-(4-isopropylpiperazine-1-carbonyl)biphenyl-4-yl)methyl)pentaneamide (AC-1652)

Step 1: Preparation of methyl 4'-formylbiphenyl-3-carboxylate

Methyl 3-bromobenzoate (1.0 equiv) and 4-formylphenylboronic acid (1.1 equiv) were thoroughly mixed with RBF, and dissolved in a 1,4-dioxane:H$_2$O (10:1) mixed solution. Degassing was performed for 20 minutes by adding Pd(dppf)Cl$_2$.DCM (0.05 equiv) to the mixed solution, and performed again for 20 minutes by adding Na$_2$CO$_3$. After degassing again for 15 minutes, the resulting solution was refluxed for 4 hours. After the reaction, the mixture was filtered with ethyl acetate (EA), extracted, dehydrated with anhydrous MgSO$_4$, concentrated by evaporation, and purified by MPLC, thereby obtaining methyl 4'-formylbiphenyl-3-carboxylate (91% yield).

Step 2: Preparation of methyl 4'-((4-fluorophenylamino)methyl)biphenyl-3-carboxylate The methyl 4'-formylbiphenyl-3-carboxylate (1.0 equiv) obtained in Step 1 and 4-fluoroaniline (3.0 equiv) were dissolved in methanol, and then stirred at room temperature for 4 hours. A reaction until an imine was formed was observed by TLC, and after the imine was formed, a methanol solution, in which 1M NaCNBH$_3$ (1.0 equiv) and 0.5M ZnCl$_2$ (1.0 equiv) were mixed, was added to the solution, and then stirred at room temperature overnight. After the reaction, under a vacuum, the methanol was removed, and the remaining solution was diluted with ethyl acetate (EA), and the organic solvent layer was washed with brine, dehydrated with anhydrous magnesium sulfate (MgSO$_4$) and concentrated by evaporation. The concentrate was purified by MPLC, thereby obtaining methyl 4'-((4-fluorophenylamino)methyl)biphenyl-3-carboxylate (97% yield).

Step 3: Preparation of methyl 4'-((N-(4-fluorophenyl)pentaneamido)methyl)biphenyl-3-carboxylate The methyl 4'-((4-fluorophenylamino)methyl)biphenyl-3-carboxylate obtained in Step 2 was dissolved in dichloromethane (DCM), added with triethanolamine (TEA), and cooled on ice. Valeroyl chloride (2.0 equiv) was added to the mixed solution, and then stirred at room temperature for 4 hours. After the reaction, RBF was added, and the organic solvent layer was washed with brine and separated. Afterward, the organic solvent layer was collected, dehydrated with anhydrous magnesium sulfate (MgSO$_4$), filtered, and concentrated by evaporation. The concentrate was purified by MPLC, thereby obtaining methyl 4'-((N-(4-fluorophenyl)pentaneamido)methyl)biphenyl-3-carboxylate (96% yield).

Step 4: Preparation of 4'-((N-(4-fluorophenyl)pentaneamido)methyl)biphenyl-3-carboxylic acid The methyl 4'-((N-(4-fluorophenyl)pentaneamido)methyl)biphenyl-3-carboxylate (1.0 equiv) obtained in Step 3 was thoroughly mixed with tetrahydrofuran (THF), mixed with an LiOH solution, and stirred for 4 hours. After the reaction, the mixed solution was concentrated, mixed with 2N HCl until the mixed solution became an acidic state, and extracted with ethyl acetate (EA). Under a vacuum, the organic solvent layer was removed and recrystallization was performed, thereby obtaining 4'-((N-(4-fluorophenyl)pentaneamido)methyl)biphenyl-3-carboxylic acid (95% yield).

Step 5: Preparation of N-(4-fluorophenyl)-N-((3'-(4-isopropylpiperazine-1-carbonyl)biphenyl-4-yl)methyl)pentaneamide The 4'-((N-(4-fluorophenyl)pentaneamido)methyl)biphenyl-3-carboxylic acid (1.0 equiv) obtained in Step 4 and 1-isopropylpiperazine (0.9 equiv), HATU (1.2 equiv) and N,N-diisopropylethylamine (DIPEA) (2.5 equiv) were dissolved in N,N-dimethylformamide (DMF), and the mixed solution was stirred at room temperature overnight. After the reaction, water was added, and the water-soluble layer was extracted with ethyl acetate (EA). The organic solvent layer was filtered and then concentrated by evaporation. The concentrate was purified by column chromatography, thereby obtaining the final product, (N-(4-fluorophenyl)-N-((3'-(4-isopropylpiperazine-1-carbonyl)biphenyl-4-yl)methyl)pentaneamide (70% yield).

$^1$H-NMR (CDCl$_3$, 400 MHz) δ 7.61 (q, 2H), 7.47 (m, J=6.0 Hz, 3H), 7.34 (d, J=7.2 Hz, 1H), 7.26 (d, J=7.6 Hz, 2H), 7.03 (m, 2H), 6.96 (m, 2H), 4.88 (s, 2H), 3.65 (d, 4H), 2.74 (m, 1H), 2.54 (d, 4H), 2.06 (t, J=7.6 Hz, 2H), 1.58 (m, 2H), 1.25 (m, 2H), 1.06 (d, J=6.8 Hz, 6H), 0.83 (t, J=7.4 Hz, 3H)

EXPERIMENTAL EXAMPLES

Experimental Example 1. Preparation of BLT2-Expressing Cells or BLT2-Nonexpressing Cells For this experiment, BLT2-nonexpressing cells and BLT2-expressing cells (CHO-BLT2 cells) were prepared by the following method.

CHO cells were obtained from Korean Cell Line Bank (KCLB, 10061), and cultured in an RPMI 1640 medium (Invitrogen) containing 10% fetal bovine serum (FBS; Life Technologies, Inc.), penicillin (50 units/mL) and an antibiotic antimycotic solution (Life Technologies, Inc.) at 37° C. under 5% CO$_2$ condition. The cells were split for 3 days using Trypsin-EDTA, maintained in a growth phase, washed with phosphate-buffered saline (PBS; 137 mM NaCl, 2.7 mM KCl, 10 mM Na$_2$HPO$_4$, 2 mM KH$_2$PO$_4$), and then added to a new medium, thereby preparing BLT2-nonexpressing cells.

In addition, in order to prepare stable CHO/BLT2 clones, CHO-K1 cells were transformed with pcDNA3-long form BLT2 encoding HA-tagged human BLT2, and selected with 0.4 mg/ml of G418 (Invitrogen, Carlsbad, Calif., USA). To screen BLT2 expression, the selected clones were analyzed by RT-PCR using a human-specific BLT2 primer, and representative clones used for the experiment were BLT2-expressing cells (CHO-BLT2 cells).

Experimental Example 2. Confirmation of Inhibitory Effect on Growth of BLT2-Expressing Cells Cell viability according to treatment of the compounds prepared in the examples were measured by a 3-(4,5-dimethylthiazol-2-yl)-2,5-diphenyltetrazolium bromide (MTT) method.

More specifically, 1×10$^4$ each of the BLT2-nonexpressing cells (CHO-pcDNA3.1 cells) and BLT2-expressing cells (CHO-BLT2 cells), which were prepared in Experimental Example 1, were dispensed in a 96-mm culture dish, and cultured for 24 hours. Afterward, the culture medium was removed, a serum-free RPMI medium was added, and after two hours, the cells were pre-treated with each of the compound prepared in one of the examples (10 μM), 10 μM DMSO (compound solvent) as a control, and 10 μM of 1-[5-ethyl-2-hydroxy-4-[[6-methyl-6-(1H-tetrazol-5-yl)heptyl]oxy]phenyl]-ethanone (LY255283; Cayman) as a positive control for 1 hour. Subsequently, after treatment of LTB$_4$ (300 nM), the cells were cultured for 24 hours. 20 μL of an MTT solution (5 mg/mL, Sigma-Aldrich) was added to each well, the cells were cultured in a humid CO$_2$ incubator at 37° C. for 4 hours, and then the supernatant was removed, and 200 μL of DMSO was added to each well to dissolve insoluble violet formazan crystals. Absorbance was measured using a microplate reader (Molecular Devices, Sunnyvale, Calif.) at 550 nm, and the measurement was repeated three times.

As a result, as shown in FIGS. 1A to 1E, when the BLT2-expressing cells (CHO-BLT2 cells) were treated with LTB$_4$ (300 nM), which is a ligand of BLT2 (DMSO+), compared with those treated with ethanol (DMSO−), cell growth increased by 20% to 35%, and when the BLT2-expressing cells (CHO-BLT2 cells) were pre-treated with the positive control LY255283, compared with those treated with the control DMSO, approximately 90% cell growth was exhibited, and therefore, it was confirmed that the inhibitory effect on cell growth was exhibited by the treatment of the compounds of the examples. Specifically, it was confirmed that compounds of the present invention AC-1632 (78.7%), AC-1635 (71.6%), AC-1646 (72.1%) and AC-1650 (82.2%) exhibited growth inhibitory effects.

The experimental result shows that the compounds of the present invention (AC-1632, AC-1635, AC-1646 and AC-1650) can inhibit BLT2-induced cell growth with very excellent efficiency, and the compounds may be used as pharmaceutical components (BLT2-blocking pharmacological molecules) that can be used as therapeutic agents for inhibiting cancer, asthma or different types of BLT2-associated inflammatory diseases.

Experimental Example 3. Confirmation of Effect of Inducing the Death of Cancer Cells by BLT2 Inhibition The inventors have experimentally confirmed that BLT2 expression was proportionally increased according to a degree of anticancer agent resistance, and the anticancer agent resistance was considerably decreased by BLT2 inhibition. Therefore, it was intended to confirm whether the death of cancer cells was induced in ovarian cancer cells (SKOV-3 cells) exhibiting anticancer agent resistance, when a compound of the present invention was co-treated with an anticancer agent, cisplatin, despite the anticancer agent resistance.

The death of cancer cells was detected using a 3-(4,5-dimethylthiazol-2-yl)-2,5-diphenyltetrazolium bromide (MTT) method. More specifically, $1 \times 10^5$ of the ovarian cancer cells (SKOV-3 cells) resistant to the anti-cancer agents were dispensed on a 12-well culture dish, and cultured for 24 hours. A 0.5% serum RPMI medium was pre-treated with each of the compound prepared in one of the examples (10 μM), 10 μM of DMSO (compound solvent) as a control, and 10 μM of LY255283 as a positive control for 30 minutes. Afterward, 50 μM of an anti-cancer agent, cisplatin, was treated, and then the cells were cultured 24 hours. A 20 μL of an MTT solution (5 mg/mL, Sigma-Aldrich) was added to each well, and the cells were cultured in a humid $CO_2$ incubator at 37° C. for 4 hours. Afterward, the supernatant was removed, and 500 L of DMSO was added to each well to dissolve insoluble violet formazan crystals. Absorbance was measured using a microplate reader (Molecular Devices, Sunnyvale, Calif.) at 550 nm, and the measurement was repeated three times.

Figure 2A:
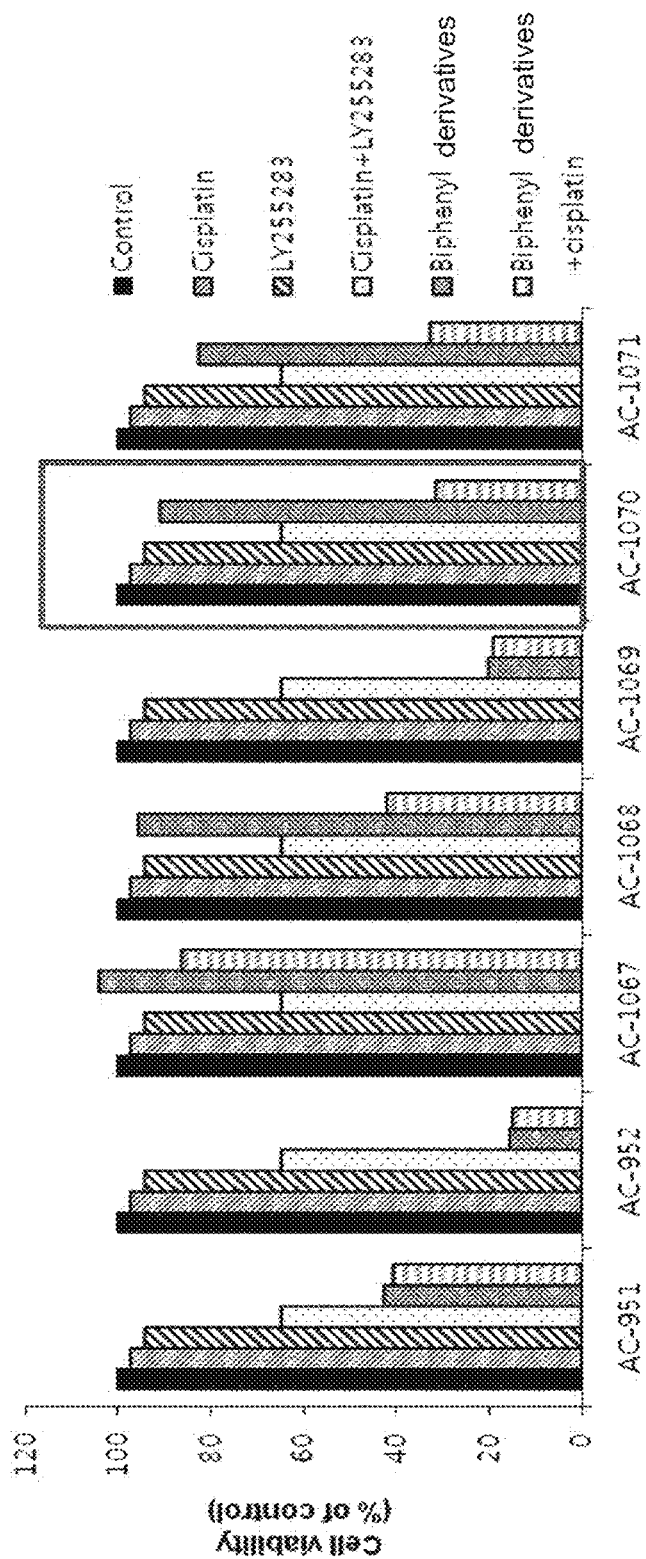
FIGS. 2A to 2C show the confirming results of the increased effect on the death of the ovarian cancer cells (SKOV-3 cells), which are known to be resistant to various anti-cancer agents, by co-treatment of the present novel compound and an anticancer agent, cisplatin.
Figure 2B:
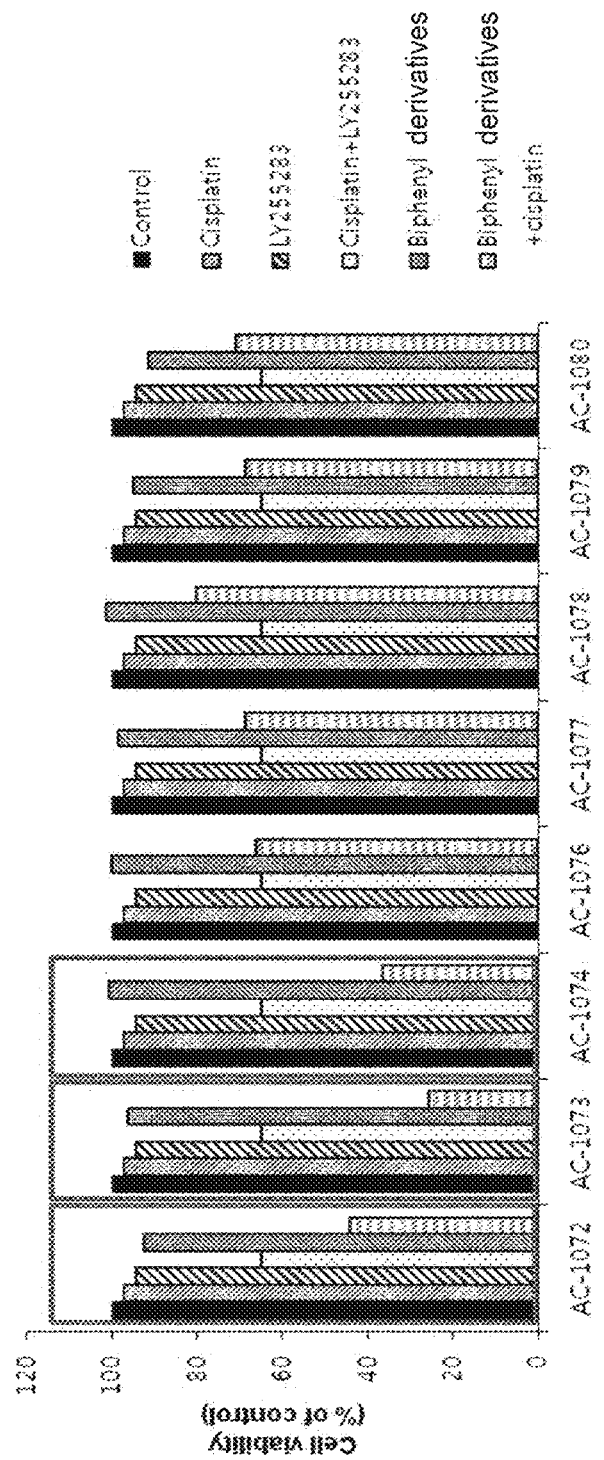
Figure 2C:
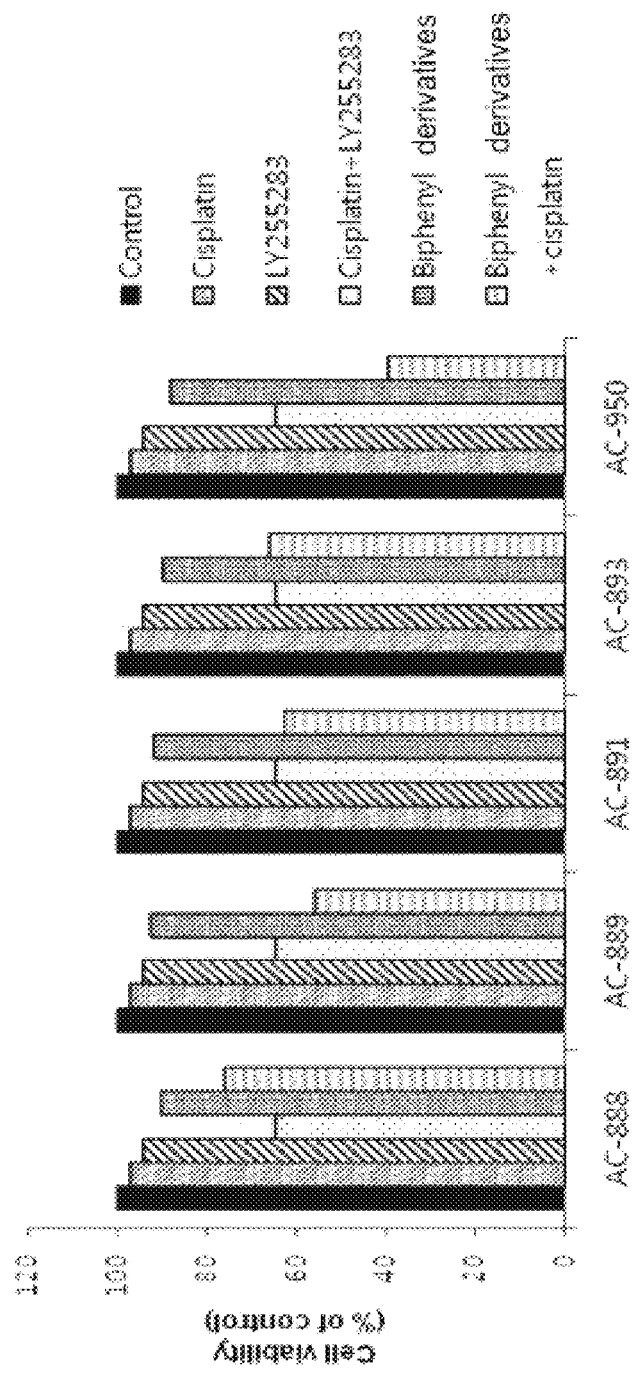
Figure 3A:
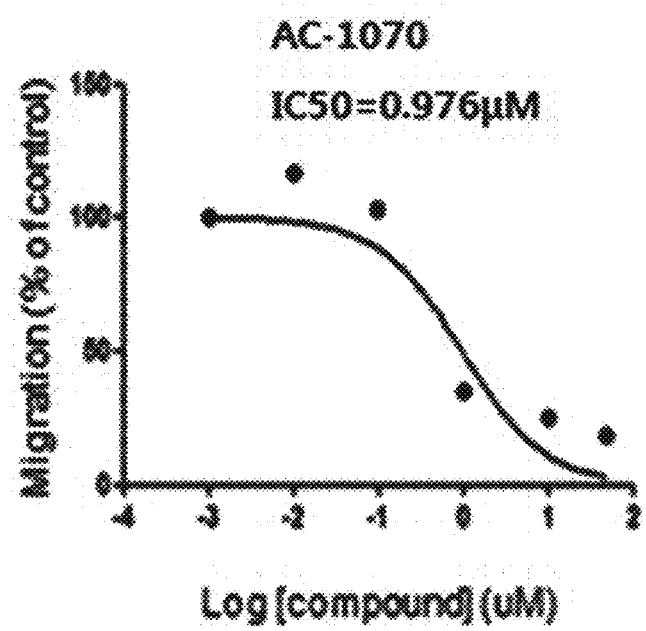
FIGS. 3A to 3D show the confirming results of the inhibitory effect of the present novel compound on the cell chemotactic motility and the 50% inhibition concentration ($IC_{50}$) in BLT2-expressing cells (CHO-BLT2 cells).
Figure 3B:
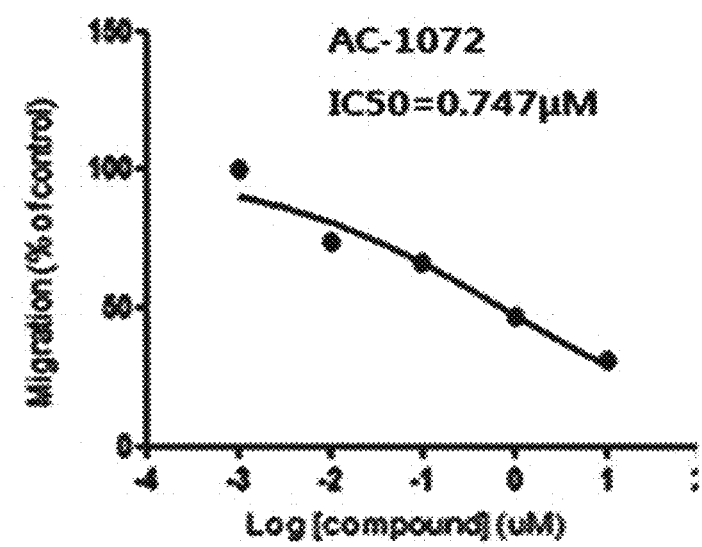
Figure 3C:
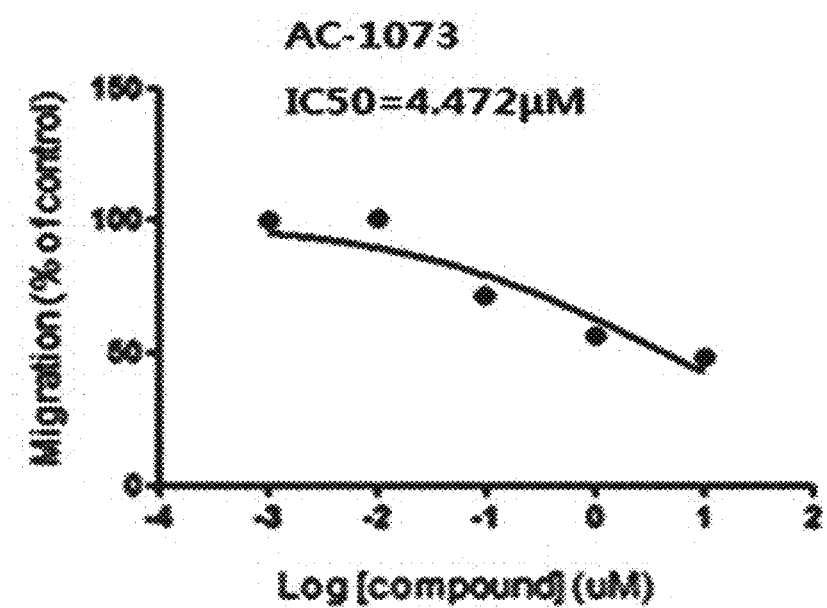
Figure 3D:
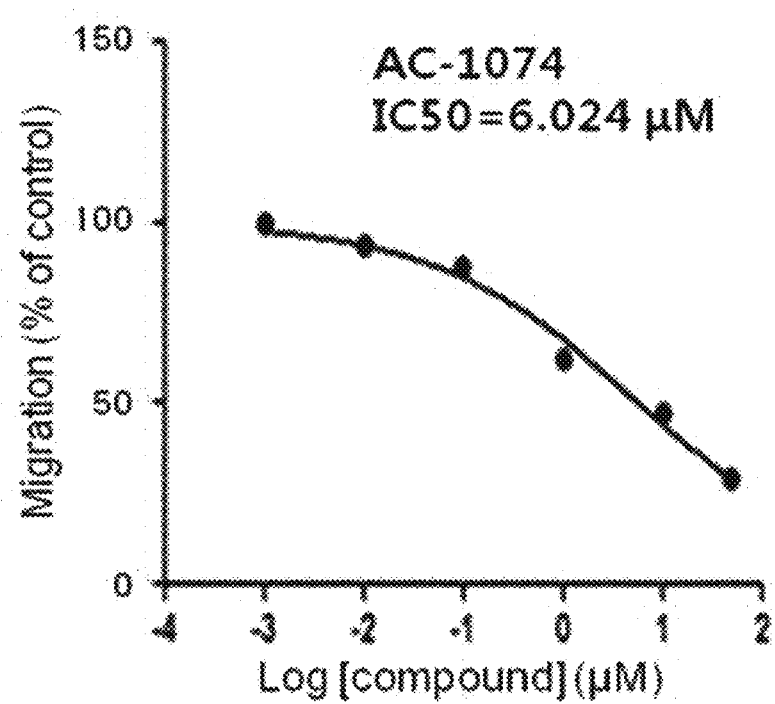

As shown in FIGS. 2A to 2C, The death of the ovarian cancer cells (SKOV-3 cells) resistant to various anti-cancer agents was increased when the positive control LY255283 and cisplatin were co-treated, compared to when the anti-cancer agent cisplatin was treated alone. In addition, when the cells were treated with AC-1070, AC-1072, AC-1073 or AC-1074 compound in the presence of cisplatin, the cell death rate was highly increase, compared with when co-treated with the positive control LY255283. The results show that the compounds of the present invention (AAC-1070, AC-1072, AC-1073 and AC-1074) can reduce anti-cancer agent resistance, thereby inducing the death of the cancer cells by the anticancer agent, cisplatin, with excellent efficiency, and therefore can be used as a pharmaceutical component for enhancing an anticancer effect.

Experimental Example 4. Confirmation of $LTB_4$-Induced Effect of Inhibiting BLT2-Dependent Chemotactic Motility Chemotactic motility was analyzed using a Transwell chamber including a polycarbonate filter (8-μm pore size, Corning Costar) with a 6.5-mm diameter. Specifically, the lower surface of the filter was coated with 10 μg/mL fibronectin in a serum-free RPMI 1640 medium at 37° C. for 1 hour. The experiment was performed by placing the filter dried and coated with RPMI 1640 media containing various amounts of $LTB_4$ in the lower wells of the Transwell chamber, and loading CHO cells, which stably express both BLT1 and BLT2, into the upper wells containing serum-free RPMI 1640 media finally at $2 \times 10^4$ cells/100 μL. To evaluate the effect of inhibitors, the cells were pre-treated with each inhibitor for 30 minutes before dispensing. After the cells were cultured at 37° C. in 5% $CO_2$ for 3 hours, the filters were fixed with methanol for 3 minutes, and stained with hematoxylin and eosin for 10 minutes. In the experiment, the cells were BLT2-expressing cells (CHO-BLT2 cells) and BLT1-expressing cells (CHO-BLT1 cells), LY255283 and U75302 were used as positive controls, and BLT2 ligand $LTB_4$, (300 nM), BLT1 ligand $LTB_4$ (10 nM), and lysophosphatidic acid (LPA; 100 nM) were used as comparative controls. The chemotactic motility was quantitatively analyzed by counting the cells on the lower side of the filter under an optical microscope (magnification, 200×). For each analysis, 6 fields were subjected to counting, each sample was analyzed twice, and the analysis was repeated three times.

As a result, as shown in FIGS. 3A to 3D and Table 1 below, in the BLT2-expressing cells (CHO-BLT2 cells), as the concentrations of the compound of the present invention (AC-1074) was increased ($10^{-4}$, $10^{-3}$, $10^{-2}$, $10^{-1}$, 1, 10 and $10^2$), the chemotactic motility of the CHO-BLT2 cells was inhibited under a serum-free condition, and the 50% inhibitory concentration ($IC_{50}$) of the AC-1074 compound was 6.024 μM.

TABLE 1

| receptor | $LTB_4$, nM | IC50, μM AC-1074 |
|---|---|---|
| BLT2 | 300 | 6.024 |

Figure 4A:
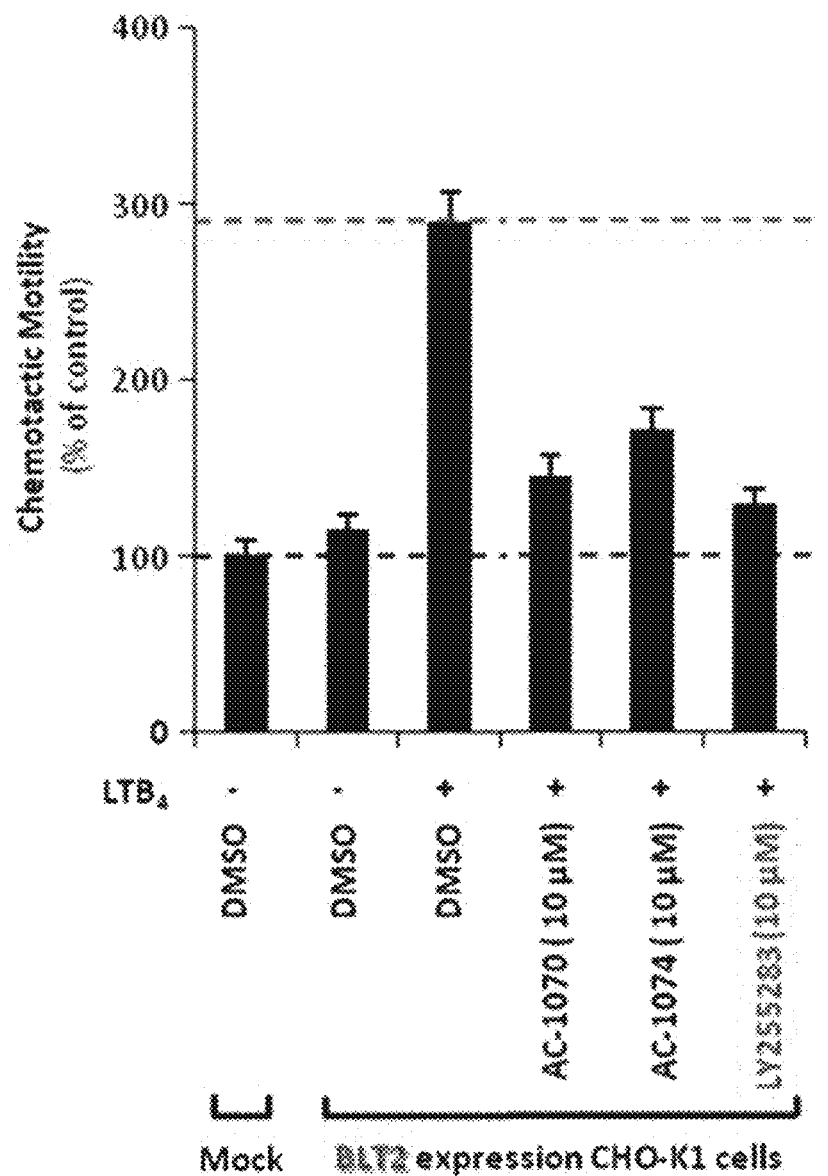
FIGS. 4A and 4C show the confirming results of the inhibitory effect of the present novel compound on the chemotactic motility in BLT2-expressing cells (CHO-BLT2 cells) or BLT1-expressing cells (CHO-BLT1 cells).

In addition, as shown in FIG. 4A, it was confirmed that, when the BLT2-expressing cells (CHO-BLT2 cells) were treated with a BLT2 ligand $LTB_4$ (300 nM) (DMSO+), compared with those treated with ethanol (DMSO−), cell chemotactic motility was increased 2.9 times, and when the BLT2-expressing cells (CHO-BLT2 cells) were pre-treated with 10 μM of LY255283 used as a positive control, compared with those treated with the ligand $LTB_4$, the chemotactic motility was 90%, and when the BLT2-expressing cells were pre-treated with the compound of the present invention (AC-1074) at 10 μM, compared with those treated with the ligand $LTB_4$ (DMSO+), the chemotactic motility was inhibited by 53%.

Figure 4B:
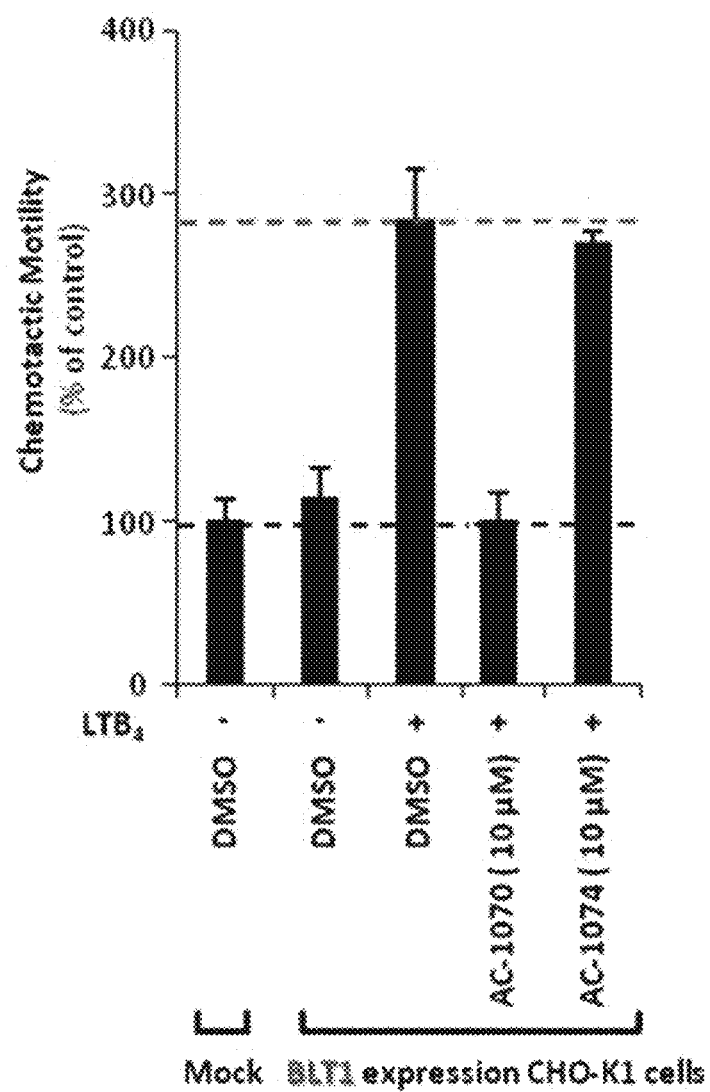

In addition, as shown in FIG. 4B, it was confirmed that, when the BLT1-expressing cells (CHO-BLT1 cells) were treated with the BLT1 ligand $LTB_4$ (10 nM) (DMSO+), compared with those treated with ethanol (DMSO−), the chemotactic motility was increased 2.8 times, and when the BLT2-expressing cells were pre-treated with the compound of the present invention (AC-1074) at 10 μM, compared with those treated with the ligand $LTB_4$ (DMSO+), there was no change in chemotactic motility.

Figure 4C:
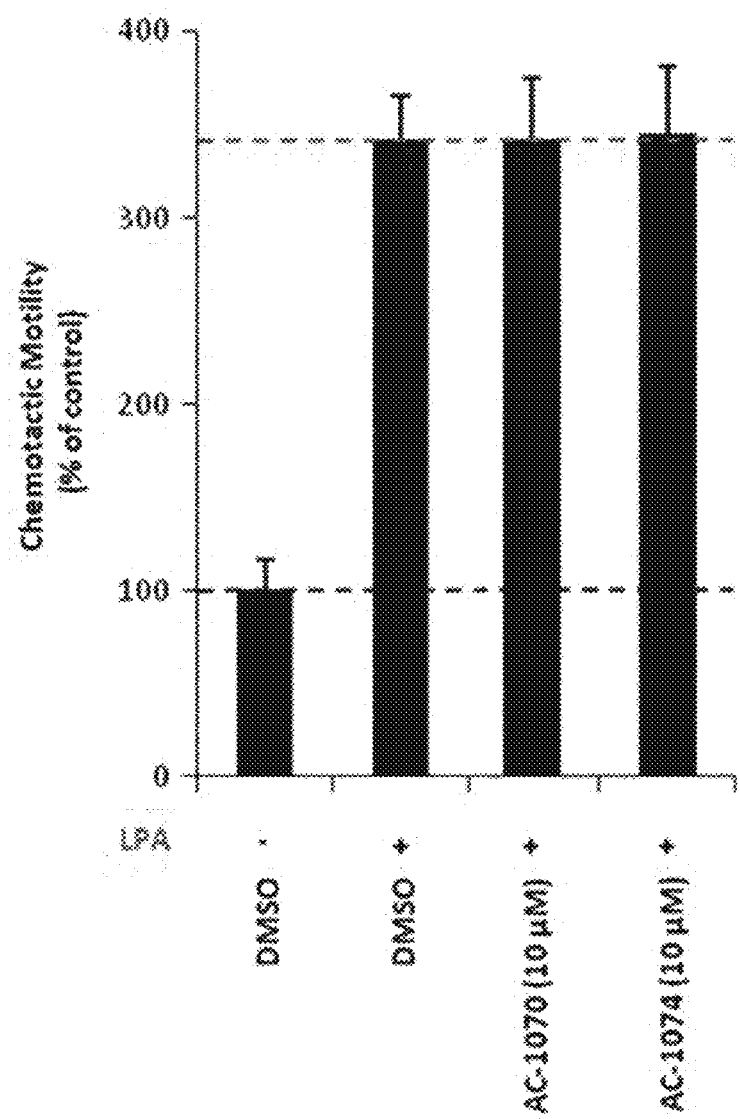

In addition, as shown in FIG. 4C, it was confirmed that, when the BLT2-expressing cells (CHO-BLT2 cells) were treated with LPA (100 nM) (DMSO+), compared with when treated with ethanol (DMSO−), chemotactic motility was increased 3.4 times, and when the BLT2-expressing cells were pre-treated with 10 μM of the compound of the present invention (AC-1074), compared with those treated with the ligand LPA (DMSO+), there was no change in chemotactic motility.

The results show that, in the cells in which BLT2 was stably expressed (CHO-BLT2 cells), the chemotactic motility was increased by the $LTB_4$ stimulus, the compound of the present invention (AC-1074) may considerably inhibit the chemotactic motility, and thus can be used as a pharmaceutical component to inhibit $LTB_4$-induced BLT2-dependent chemotactic motility.

Experimental Example 5. Confirmation of Effect of Inhibiting $LTB_4$ and BLT2 Binding The inhibition of $LTB_4$ and BLT2 binding (ligand binding affinity) was analyzed using radioactive tritium (H3)-labeled $LTB_4$ ([3H]$LTB_4$, ARC; specific activity 160.0 Ci/mmol). After $2\times10^6$ of CHO-BLT2 cells were plated into a 100-mm culture dish and cultured for 48 hours, an experimental method was carried out as follows: Collected cells were treated using a homogenizer a total of five times for 1 minute each to separate proteins of the cell membrane. Afterward, the cells were subjected to centrifugation at 4° C. and 45,000 rpm for 40 minutes to only collect the proteins of the cell membrane, thereby quantifying a protein concentration at 40 μg/45 μL. When a BLT2-containing cell membrane protein which was quantified in the same manner was treated with the same amount of [3H]$LTB_4$ (5 nM), and then a different concentration ($10^{-9}$, $10^{-8}$, $10^{-7}$, $10^{-6}$ or $10^{-5}$ M) of a compound, a degree of inhibiting the tritium-labeled $LTB_4$ and BLT2 binding was measured using a Hidex 300sL liquid scintillation counter.

Figure 5:
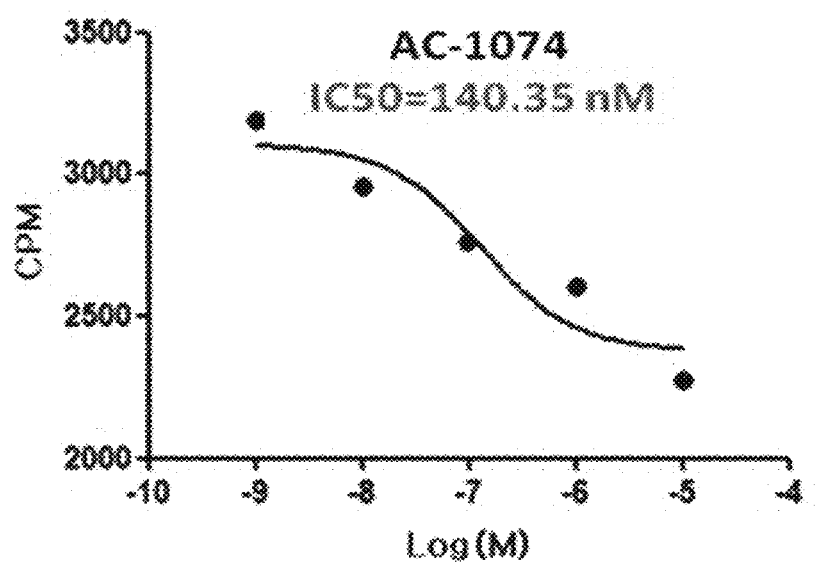
FIG. 5 shows the confirming result of the inhibitory effect of the present novel compound on the binding affinity of LTB$_4$ to BLT2 in the BLT2-expressing cells (CHO-BLT2 cells).

As a result, as shown in FIG. 5, it was confirmed that, in the BLT2-expressing cells (CHO-BLT2 cells), as the concentration of the compound of the present invention (AC-1074) was increased (10–9, $10^{-8}$, $10^{-7}$, $10^{-6}$ and $10^{-5}$), LTB4 and BLT2 binding was inhibited, and the $IC_{50}$ of the AC-1074 compound was 140.35 nM.

Experimental Example 6. Confirmation of Anti-Asthma Effect by LBT2 Inhibition

Mast cells play a pivotal role in the initial reaction to asthma, and when an allergen enters the body from the outside through an airway, the mast cells are activated, thereby secreting various cytokines (interleukin-4 and interleukin-13). Due to the cytokines, the influx of inflammatory cells, and the generation of mucus and the airway contraction occur. The inventors used 7-week-old (18 to 20 g) female BALB/c mice provided by Orient (Seoungnam, Korea) for the experiment to confirm the anti-asthma effect, and asthma was induced in the mice. On day 1 and day 14, 2.5 mg of an adjuvant aluminum hydroxide gel (alum; Pierce, Rockford, Ill.) containing a 20 mg of ovalbumin (OVA) was injected intraperitoneally to sensitize the female C57BL/6 mice. After the two initial sensitizations, on day 21, day 22 and day 23, 1% OVA was sprayed into the mice using an ultrasonic nebulizer. The compound of the present invention such as AC-1074 (5 mg/kg), LY255283 (5 mg/kg, Cayman) or DMSO was intraperitoneally injected one hour before the 1% OVA was sprayed. After the initial sensitizations, on day 24, AHR was detected, and on day 25, the mice were dissected to observe asthma phenotypes such as the expression of an inflammatory cytokine IL-4, and the influx of the inflammatory cells (neutrophils). In addition, the AHR detection was performed after an airway constrictor methacholine (6.25 to 50 mg/ml depending on conditions) was administered to the mice. The administration of the airway constrictor was performed by spraying through an inlet of the chamber using an ultrasonic nebulizer for 3 minutes. The AHR was analyzed using an enhanced pause as the indicator of the asthma phenomenon.

Figure 6:
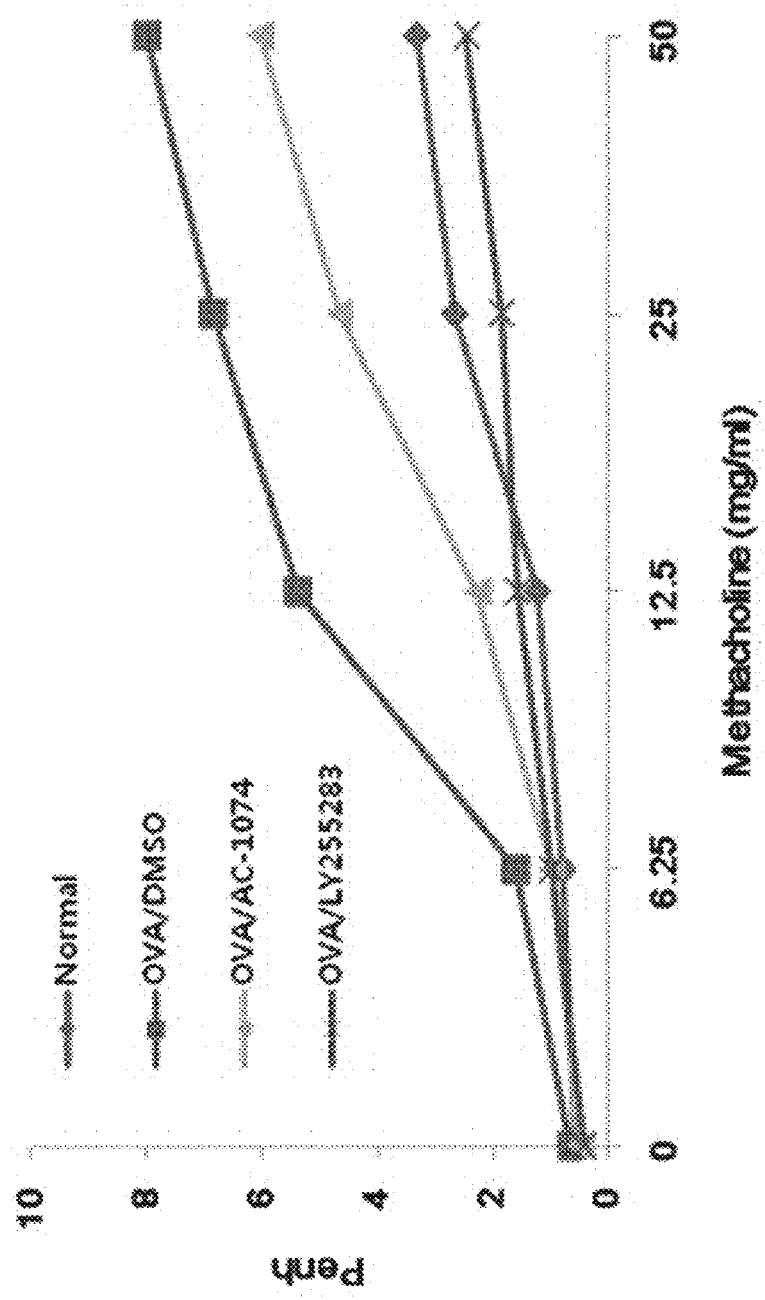
FIG. 6 shows the confirming result of the reducing effect of the present novel compound on the airway hyperresponsiveness (AHR) in the asthma-induced mice.

As a result, as shown in FIG. 6, it was confirmed that, in the asthma-induced mice (OVA/DMSO), compared with mice in which asthma was not induced (normal), AHR was increased approximately 12 times, and when mice were pre-treated with the compound of the present invention (AC-1074) at 10 μM, compared with the mice to which 50 mg/ml of the airway constrictor was administered, AHR was reduced by 42%.

Figure 7:
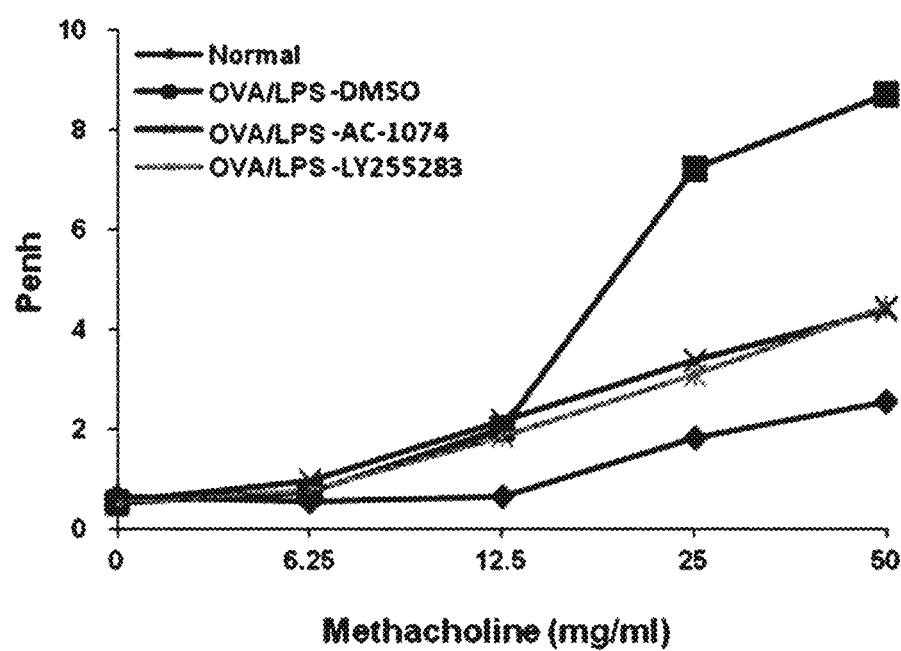
FIG. 7 shows the confirming result of the reducing effect of the present novel compound on the airway hyperresponsiveness (AHR) in the severely asthma-induced mice.
Figure 8:
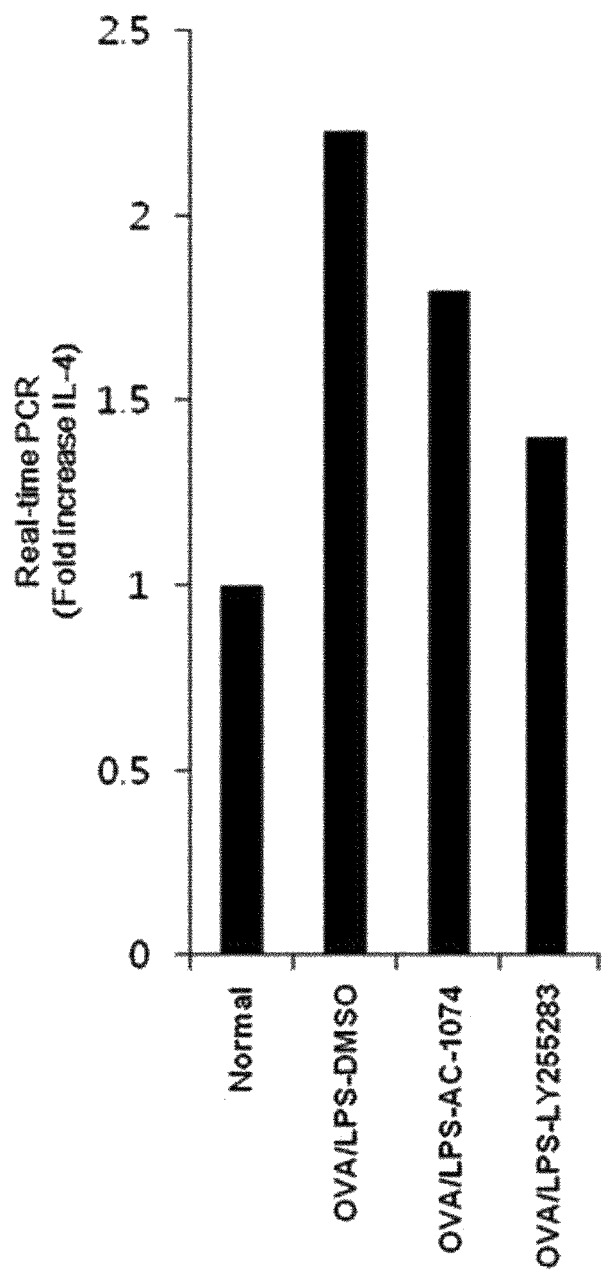
FIG. 8 shows a reducing effect of the present novel compound on the interleukin-4 (IL-4) production in the severely asthma-induced mice.

In addition, as shown in FIGS. 7 and 8, it was confirmed that, when pre-treated with 10 μM of the positive control LY255283, in the severely asthma-induced mice to which 50 mg/ml of the airway constrictor was administered, AHR was reduced by 69.2%, and the production of IL-4 in cells separated from the abdominal cavity of the mice was reduced by 67.2%. Furthermore, it was confirmed that, when pre-treated with the compound of the present invention (AC-1074) at M, in the severely asthma-induced mice to which the airway constrictor was administered at 50 mg/ml, AHR was reduced by 59%, and the production of IL-4 in the cells separated from the abdominal cavity of the mice was reduced by 35.5%.

The results show that the compound of the present invention (AC-1074) can inhibit AHR in asthma animal models, and inhibit the production of the inflammatory cytokine IL-4 to alleviate the symptoms of asthma, and therefore can be used as a pharmaceutical ingredient having an antiasthma effect.

INDUSTRIAL AVAILABILITY

The present invention relates to a novel compound having BLT2 inhibitory activity and a pharmaceutical composition for preventing or treating an inflammatory disease, which includes the compound. The inventors identified a novel compound containing BTL2 inhibitory activity to solve the problems of the conventional compounds that had been designed to treat an inflammatory disease; for example, the instability in living organism and the difficulty on the mass production. In addition, it was experimentally confirmed that the present novel compound had an excellent effect on the enhancement of the cancer cell death, on the inhibition of the metastasis and chemotactic mobility, and on the anti-asthma activity. Therefore, the present novel compound can be used as a very effective pharmaceutical component for treating the inflammatory-related diseases.

The invention claimed is:

1. A compound represented by Formula 1 or a pharmaceutically acceptable salt thereof:

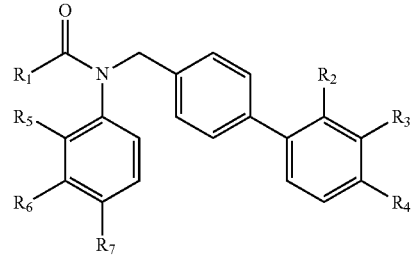

[Formula 1]

wherein,
$R_1$ is $C_1$ to $C_{10}$ alkyl,

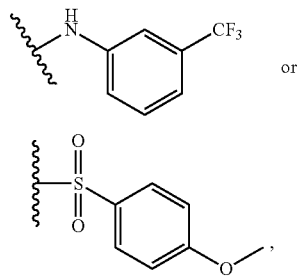 or

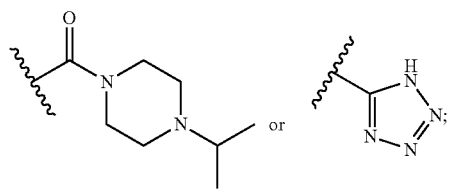 [SMILES: *C(=O)N1CCN(C(C)C)CC1 ; *c1nnn[nH]1]

$R_2$ is hydrogen,

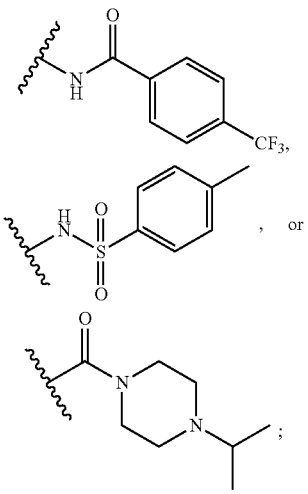

$R_3$ is hydrogen,

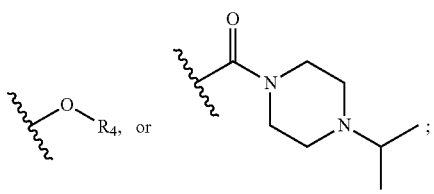

$R_4$ is hydrogen,

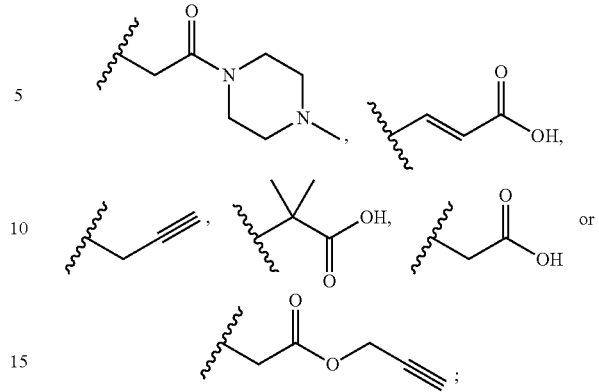

and $R_5$, $R_6$, and $R_7$ are each independently hydrogen, halogen, nitro, methyl, trifluoromethyl or methoxy.

2. The compound of claim 1, wherein
$R_1$ is methyl, n-butyl, or
$R_2$ is hydrogen;

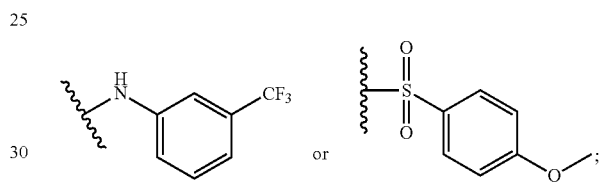

$R_3$ is hydrogen,

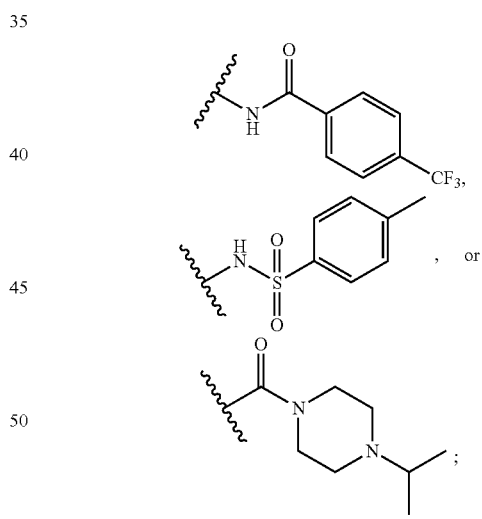

$R_4$ is hydrogen,

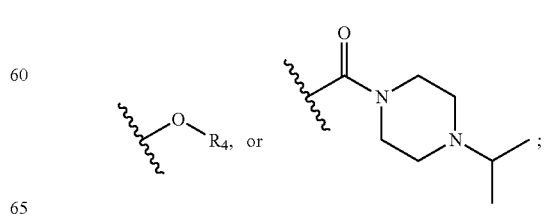

wherein $R_a$ is hydrogen, $C_1$ to $C_{10}$ alkyl, $C_1$ to $C_5$ carboxyl, where $R_a$ is hydrogen, methyl, $C_2$ to $C_3$ carboxyl,

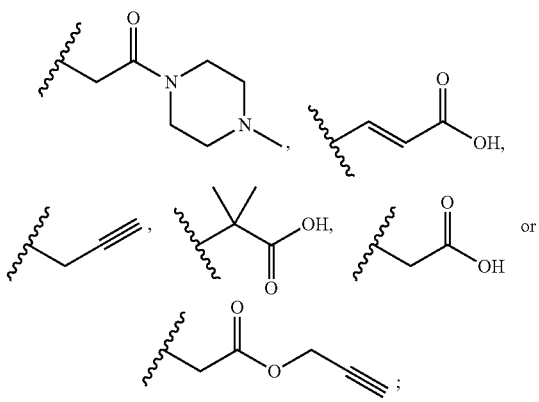

and

R$_5$, R$_6$, and R$_7$ are each independently hydrogen, halogen, nitro, methyl, trifluoromethyl or methoxy.

3. The compound of claim 1 wherein
R1 is methyl, n-butyl,

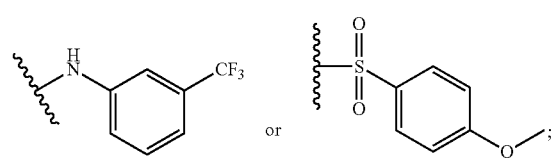 [SMILES: *Nc1cccc(C(F)(F)F)c1 ; *S(=O)(=O)c1ccc(OC)cc1]

R2 is hydrogen;
R3 is hydrogen,

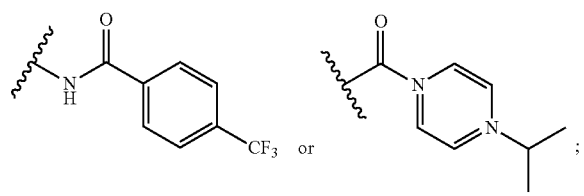

R$_4$ is hydrogen or

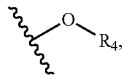

where R$_a$ is hydrogen, methyl, C$_2$ to C$_3$ carboxyl,

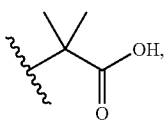 [SMILES: *C(C)(C)C(=O)O]

or

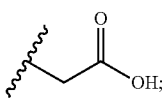 [SMILES: *CC(=O)O]

and

R$_5$, R$_6$, and R$_7$ are each independently hydrogen, halogen, methyl, or trifluoromethyl.

4. The compound of claim 1, wherein the compound is selected from the group consisting of:
- N-((3'-(4-methylphenylsulfonamido)biphenyl-4-yl) methyl)-N-phenylpentaneamide;
- N-(4'-((N-phenylpentaneamido)methyl)biphenyl-3-yl)-4-(trifluoromethyl)benzamide;
- N-(3-fluorophenyl)-N-((3'-(4-methylphenylsulfonamido) biphenyl-4-yl)methyl)pentaneamide;
- N-(4'-((N-3-fluorophenyl)pentaneamido)methyl)biphenyl-3-yl)-4-(trifluoromethyl)benzamide;
- 1-(3-fluorophenyl)-1-((4'-methoxybiphenyl-4-yl) methyl)-3-(3-(trifluoromethyl)phenyl)urea;
- N-(3-fluorophenyl)-N-((4'-methoxybiphenyl-4-yl) methyl)-1-(4-methoxyphenylsulfonyl)methaneamide;
- 1-(3-fluorophenyl)-1-((4'-hydroxybiphenyl-4-yl)methyl)-3-(3-(trifluoromethyl)phenyl)urea;
- 2-(4'-((1-(3-fluorophenyl)-3-(3-(trifluoromethyl)phenyl) ureido)methyl)biphenyl-4-yloxy)acetic acid;
- 4-(4'-((N-(3-fluorophenyl)pentaneamido)methyl)biphenyl-4-yloxy)butanoic acid;
- 2-(4'-((N-(3-fluorophenyl)pentaneamido)methyl)biphenyl-4-yloxy)-2-methylpropanoic acid;
- (E)-3-(4'-((N-(3-fluorophenyl)pentaneamido)methyl)biphenyl-4-yloxy)acrylic acid;
- 3-(4'-((N-(3-fluorophenyl)pentaneamido)methyl)biphenyl-4-yloxy)propanoic acid;
- N-(3-fluorophenyl)-N-((4'-(2-(4-methylpiperazine-1-yl)-2-oxoethoxy)biphenyl-4-yl)methyl)pentaneamide;
- prop-2-ynyl 2-(4'-((N-(3-fluorophenyl)pentaneamido) methyl)biphenyl-4-yloxy)acetate;
- N-(3-fluorophenyl)-N-((4'-(prop-2-ynyloxy)biphenyl-4-yl)methyl)pentaneamide;
- 4'-((N-(2-fluorophenyl)pentaneamido)methyl)biphenyl-4-carboxylic acid;
- 4'-((N-(4-fluorophenyl)pentaneamido)methyl)biphenyl-4-carboxylic acid;
- 4'-((N-(2-methoxyphenyl)pentaneamido)methyl)biphenyl-3-carboxylic acid;
- 4'-((N-(3-methoxyphenyl)pentaneamido)methyl)biphenyl-3-carboxylic acid;
- 4'-((N-(4-methoxyphenyl)pentaneamido)methyl)biphenyl-3-carboxylic acid;
- N-((2'-(1H-tetrazol-5-yl)biphenyl-4-yl)methyl)-N-phenylpentaneamide;
- N-((4'-methoxybiphenyl-4-yl)methyl)-N-phenylpentaneamide;
- N-((4'-hydroxybiphenyl-4-yl)methyl)-N-phenylpentaneamide;
- 2-(4'-((N-phenylpentaneamido)methyl)biphenyl-4-yloxy) acetic acid;
- N-(3-fluorophenyl)-N-((4'-methoxybiphenyl-4-yl) methyl)pentaneamide;
- N-(3-fluorophenyl)-N-((4'-hydroxy-[1,1'-biphenyl]-4-yl) methyl)acetamide;
- 2-((4'-((N-(3-fluorophenyl)acetamido)methyl)-[1,1'-biphenyl]-4-yl)oxy)acetic acid;
- N-(3-chlorophenyl)-N-((4'-methoxybiphenyl-4-yl) methyl)pentaneamide;
- N-(3-chlorophenyl)-N-((4'-hydroxybiphenyl-4-yl) methyl)pentaneamide;
- 2-(4'-((N-(3-chlorophenyl)pentaneamido)methyl)biphenyl-4-yloxy)acetic acid;
- N-(3-bromophenyl)-N-((4'-methoxybiphenyl-4-yl) methyl)pentaneamide;

N-((4'-(hydroxybiphenyl-4-yl)methyl)-N-(3-(trifluoromethyl)phenyl)pentaneamide;
2-(4'-((N-(3-bromophenyl)pentaneamido)methyl)biphenyl-4-yloxy)acetic acid;
N-((4'-methoxybiphenyl-4-yl)methyl)-N-(3-(trifluoromethyl)phenyl)pentaneamide;
N-((4'-hydroxybiphenyl-4-yl)methyl)-N-(3-nitrophenyl)pentaneamide;
2-(4'-((N-(3-(trifluoromethyl)phenyl)pentaneamido)methyl)biphenyl-4-yloxy)acetic acid;
N-((4' methoxybiphenyl-4-yl)methyl)-N-m-tolylpentaneamide;
N-((4'-hydroxydiphenyl-4-yl)methyl)-N-m-tolylpentaneamide
2-(4'-((N-m-tolylpentaneamido)methyl)biphenyl-4-yloxy)acetic acid;
2-(4'-((N-(3-nitrophenyl)pentaneamido)methyl)biphenyl-4-yloxy)acetic acid;
N-(3-iodophenyl)-N-((4'-methoxybiphenyl-4-yl)methyl)pentaneamide;
N-((4'-hydroxybiphenyl-4-yl)methyl)-N-(3-iodophenyl)pentaneamide;
2-(4'-((N-(3-iodophenyl)pentaneamido)methyl)biphenyl-4-yloxy)acetic acid;
N-(3-fluorophenyl)-N-((4'-methoxybiphenyl-4-yl)methyl)pentaneamide
N-(3-fluorophenyl)-N-((4'-hydroxybiphenyl-4-yl)methyl)pentaneamide;
2-(4'-((N-(3-fluorophenyl)pentaneamido)methyl)biphenyl-4-yloxy)acetic acid;
N-((4'-(4-isopropylpiperazine-1-carbonyl)biphenyl-4-yl)methyl)-N-phenylpentaneamide;
N-(4-fluorophenyl)-N-((4'-(4-isopropylpiperazine-1-carbonyl)-biphenyl-4-yl)methyl)pentaneamide;
N-((3'-(4-isopropylpiperazine-1-carbonyl)biphenyl-4-yl)methyl)-N-phenylpentaneamide;
N-(4-fluorophenyl)-N-((3'-(4-isopropylpiperazine-1-carbonyl)biphenyl-4-yl)methyl)pentaneamide; and
N-(3-bromophenyl)-N-((4'-hydroxybiphenyl-4-yl)methyl)pentaneamide.

5. The compound of claim 4, wherein the compound is selected from the group consisting of:
N-(4'-((N-phenylpentaneamido)methyl)biphenyl-3-yl)-4-(trifluoromethyl)benzamide;
N-(4'-((N-3-fluorophenyl)pentaneamido)methyl)biphenyl-3-yl)-4-(trifluoromethyl)benzamide;
N-(3-fluorophenyl)-N-((4'-methoxybiphenyl-4-yl)methyl)-1-(4-methoxyphenylsulfonyl)methaneamide;
N-(3-fluorophenyl)-N-((4'-methoxybiphenyl-4-yl)methyl)-1-(4-methoxyphenylsulfonyl)methaneamide;
2-(4'-((1-(3-fluorophenyl)-3-(3-(trifluoromethyl)phenyl)ureido)methyl)biphenyl-4-yloxy)acetic acid;
2-(4'-((N-(3-fluorophenyl)pentaneamido)methyl)biphenyl-4-yloxy)-2-methylpropanoic acid;
N-(3-fluorophenyl)-N-((4'-(2-(4-methylpiperazine-1-yl)-2-oxoethoxy)biphenyl-4-yl)methyl)pentaneamide;
2-(4'-((N-phenylpentaneamido)methyl)biphenyl-4-yloxy)acetic acid;
N-((4'-(hydroxybiphenyl-4-yl)methyl)-N-(3-(trifluoromethyl)phenyl)pentaneamide;
N-((4'-hydroxydiphenyl-4-yl)methyl)-N-m-tolylpentaneamide
N-(3-fluorophenyl)-N-((4'-methoxybiphenyl-4-yl)methyl)pentaneamide
N-(3-fluorophenyl)-N-((4'-hydroxybiphenyl-4-yl)methyl)pentaneamide;
2-(4'-((N-(3-fluorophenyl)pentaneamido)methyl)biphenyl-4-yloxy)acetic acid;
N-(4-fluorophenyl)-N-((4'-(4-isopropylpiperazine-1-carbonyl)-biphenyl-4-yl)methyl)pentaneamide;
N-(4-fluorophenyl)-N-((3'-(4-isopropylpiperazine-1-carbonyl)biphenyl-4-yl)methyl)pentaneamide; and
N-(3-bromophenyl)-N-((4'-hydroxybiphenyl-4-yl)methyl)pentaneamide.

6. A pharmaceutical composition comprising the compound of claim 1, or a pharmaceutically acceptable salt thereof.

7. A method for treating an inflammatory disease, comprising:
administering a composition comprising the compound of claim 1, or a pharmaceutically acceptable salt thereof as an active ingredient to a subject, thereby inhibiting leukotriene B4 receptor 2 (BLT2) activity,
wherein the inflammatory disease is asthma.

8. A method of enhancing an anticancer effect of an anti-cancer agent, comprising:
administering a composition comprising the compound of claim f, or a pharmaceutically acceptable salt thereof, and the anti-cancer agent to a subject,
wherein the compound of claim 1, or a pharmaceutically acceptable salt thereof, inhibits BLT2 activity, thereby reducing anti-cancer agent resistance and enhancing the anticancer effect of the anti-cancer agent.

9. A method of inhibiting chemotactic motility of a cell, comprising:
administering a composition comprising the compound of claim 1, or a pharmaceutically acceptable salt thereof to a subject,
wherein the compound of claim 1, or a pharmaceutically acceptable salt thereof, inhibits BLT2 activity, thereby inhibiting BLT2-dependent chemotactic motility of the cell.

* * * * *